(12) United States Patent
McElroy et al.

(10) Patent No.: US 8,716,265 B2
(45) Date of Patent: May 6, 2014

(54) 4-QUINOLINEMETHANOLS AS ANTI-MALARIAL AGENTS

(75) Inventors: John F. McElroy, Wilmington, DE (US); Robert J. Chorvat, West Chester, PA (US); David Nugiel, Cherry Hill, NJ (US)

(73) Assignee: Jenrin Discovery, Inc., Wilmington, DE (US)

( * ) Notice: Subject to any disclaimer, the term of this patent is extended or adjusted under 35 U.S.C. 154(b) by 0 days.

(21) Appl. No.: 13/300,511

(22) Filed: Nov. 18, 2011

(65) Prior Publication Data

US 2012/0178717 A1    Jul. 12, 2012

Related U.S. Application Data

(60) Provisional application No. 61/415,071, filed on Nov. 18, 2010.

(51) Int. Cl.
*A61K 31/47* (2006.01)
*A61K 31/4709* (2006.01)
*C07D 401/06* (2006.01)
*C07D 401/14* (2006.01)
*A61P 31/06* (2006.01)
*C07F 9/60* (2006.01)
*A61K 31/675* (2006.01)
*C07D 215/14* (2006.01)
*A61P 33/06* (2006.01)

(52) U.S. Cl.
USPC ............... 514/82; 514/311; 514/314; 546/22; 546/167; 546/174; 546/175; 546/176

(58) Field of Classification Search
None
See application file for complete search history.

(56) References Cited

U.S. PATENT DOCUMENTS 6,664,397 B1    12/2003   Fletcher et al.

FOREIGN PATENT DOCUMENTS

| WO | 2008/060269 A2 | 5/2008 |
| WO | 2009/106599 A2 | 9/2009 |
| WO | WO 2010144101 A1 * | 12/2010 |

OTHER PUBLICATIONS

Milner, Erin et al., Structure Activity Relationships of 4-Position Diamine Quinoline Methanols as Intermittent Preventative Treatment (IPT) against *Plasmodium falciparum*, J. Med. Chem. 2011, 54(18), 6277-85. Epub Aug. 22, 2011.
Boykin, Jr, David W. et al., Antimalarials. IV. New synthesis of alpha-(2-pyridyl)- and alpha-(2-piperidyl-2-aryl-4-quinolinemethanols, J. Med. Chem. 1968, 11 (2), 273-277.
PCT/US11/61550 International Search Report and Written Opinion, mailed Jun. 13, 2013.

* cited by examiner

*Primary Examiner* — Janet L Andres
*Assistant Examiner* — Timothy R Rozof
(74) *Attorney, Agent, or Firm* — Vance Intellectual Property, PC

(57) ABSTRACT

The present invention relates to substituted 4-qinolinemethanols and pharmaceutical compositions thereof and methods of using the same for treating of malaria, tuberculosis, and other infectious diseases.

18 Claims, No Drawings

4-QUINOLINEMETHANOLS AS ANTI-MALARIAL AGENTS

CROSS-REFERENCE TO RELATED APPLICATIONS

The present application claims priority benefit under 35 U.S.C. §119(e) of U.S. Provisional Patent Application Ser. No. 61/415,071 filed 18 Nov. 2010. The disclosure this application is incorporated herein by reference.

FIELD OF THE INVENTION

The present invention provides substituted-quinoline based anti-malarial agents and pharmaceutical compositions thereof and methods of using the same for treating malaria, tuberculosis, or other infectious diseases, and a combination thereof.

BACKGROUND OF THE INVENTION

Malaria, a vector-borne infectious disease caused by protozoan parasites, is widespread in tropical and subtropical regions of the world. Each year, there are estimated to be over 500 million cases of malaria, causing the death of between one and three million people. Ninety percent of malaria-related deaths occur in Sub-Saharan Africa, the majority of which are young children. While malaria predominantly effects populations located in Africa and Indonesia, the United States reported 1,337 cases of malaria acquired in malaria-endemic countries, including 8 deaths, in 2001. Even though malaria has been eradicated in the United States since the early 1950's, the two species that were responsible for malaria transmission prior to eradication, Anopheles quadrimaculatus in the east and Anopheles freeborni in the west, are still widely prevalent and present a constant risk that malaria could be reintroduced in the United States. Malaria is contracted when one is bitten by an infective female Anopheles mosquito. Infection occurs when saliva, containing the plasmodium parasite, is transferred during mosquito feeding. Once inside the blood, parasites travel to the liver and multiply. The parasites are released from the liver and back into the bloodstream where they invade the red blood cells and multiply again eventually causing symptoms that include lightheadedness, shortness of breath, tachycardia, fever, chills, nausea, flu-like illness, and, in severe cases, coma, and death.

U.S. Pat. No. 4,327,215, J Med Chem 14, 926 (1971) and J Med Chem 17, 210 (1974) describes the synthesis of quinoline derivatives of the following structure:

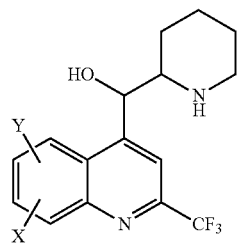

A wherein X and Y can be halogen, methoxy or trifluoromethyl. These compounds are described as anti-malarials and antibacterials being potentially useful for treating a variety of infections including malaria and tuberculosis.

WO 2008/060269 describes quinoline derivatives of the following structure:

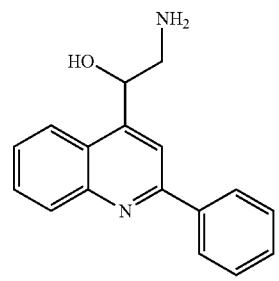

B wherein the phenyl ring can be substituted by alkyl, Cl, or F and the amino group can be substituted by an alkyl. These compounds are described as anti-malarials.

Mefloquine is an orally-administered and widely used anti-malarial drug for prophylaxis against and treatment of malaria. Mefloquine prevents the development of malaria by attacking parasites once they have entered the red blood cells and prevents them from multiplying further. While the exact mechanism of action is unknown, mefloquine is thought to work by blocking the action of a chemical that the parasites produce to protect themselves once inside the red blood cells. The parasites inside the red blood cells digest hemeoglobin. To prevent themselves from being damaged by toxic levels of heme, the malaria parasites produce a chemical that converts heme into a compound that is nontoxic. Mefloquine is believed to blocks this process.

In addition to its efficacy against *plasmodium falciparum*, mefloquine has also been reported to have activity against mycobacterium tuberculosos (TB) [Antimicrob. Agents Chemother., 2000, 44, 848; Antimicrob, Agents Chemother., 1999, 43, 1870; Antimicrob, Agents Chemother., 2004, 48, 3556] as well as, antimicrobial, antiprotozoan, antibacterial and anti fungal activity.

In addition to acting in the periphery to treat malaria, mefloquine also crosses the blood-brain barrier (BBB), producing a spectrum of psychiatric and neurological disorders, including hallucinations, delusional thinking, convulsions, depression, anxiety, paranoia, aggression, nightmares, insomnia, peripheral motor-sensory neuropathy, vestibular (balance) damage, suicidal ideation and symptoms of traumatic brain injury. The incidence and severity of adverse psychiatric side effects has limited the use of this otherwise best in class antimalarial agent.

It is well known that binding to non-targeted receptors in brain can often lead to unwanted psychiatric and neurological side effects of non-Central Nervous System (CNS) drugs [*Endocrine Reviews* 2006, 27: 73]. Access to the CNS is neither associated with nor necessary for mefloqine efficacy against parasites and/or other infections. Reducing or eliminating the ability of mefloquine to cross the BBB, or otherwise reducing brain levels sufficient to prevent psychiatric and neurological side effects, while retaining antimalarial and other therapeutic efficacy, would result in a safer therapy. The need for new agents with greater safety and high therapeutic effectiveness, coupled with the emerging resistance strains to current treatments has created an urgent unmet medical need. There is, therefore, a real and continuing necessity for the development of improved medications that treat or prevent malaria.

In view of the above, it is highly desirable to find effective and highly selective anti-malarials with limited or no CNS adverse side effects, including hallucinations, delusional thinking, convulsions, depression, anxiety, paranoia, aggression, nightmares, insomnia, peripheral motor-sensory neuropathy, vestibular (balance) damage, suicidal ideation and symptoms of traumatic brain injury. In particular, it is desirable to find compounds that exert their antimalarial action in peripheral tissues (e.g., blood and liver), while not entering in brain. In this way, peripherally-mediated beneficial effects of anti-malarial agents should be maintained, whereas CNS side effects should be reduced or eliminated. This should provide a novel opportunity to develop safer alternatives to highly brain penetrant anti-malarial agents for the prevention or treatment of malaria and other infectious diseases (e.g., tuberculosis).

SUMMARY OF THE INVENTION

Accordingly, in an aspect, the present invention provides novel quinoline derivatives or pharmaceutically acceptable salts thereof.

In another aspect, the present invention provides novel pharmaceutical compositions, comprising: a pharmaceutically acceptable carrier and a therapeutically effective amount of at least one of the compounds of the present invention or a pharmaceutically acceptable salt form thereof.

In another aspect, the present invention provides novel methods for treating malaria, tuberculosis, or other infectious diseases, and a combination thereof, comprising: administering to a mammal in need of such treatment a therapeutically effective amount of at least one of the compounds of the present invention or a pharmaceutically acceptable salt form thereof.

In another aspect, the present invention provides processes for preparing novel compounds.

In another aspect, the present invention provides novel compounds or pharmaceutically acceptable salts for use in therapy.

In another aspect, the present invention provides the use of novel compounds for the manufacture of a medicament for the treatment of malaria, tuberculosis, or other infectious diseases, and a combination thereof.

These and other objects, which will become apparent during the following detailed description, have been achieved by the inventors' discovery that the presently claimed compounds or pharmaceutically acceptable salt forms thereof are expected to be effective for the treatment of malaria, tuberculosis, and other infectious diseases.

DETAILED DESCRIPTION OF THE INVENTION

All references cited herein are hereby incorporated in their entirety herein by reference.

The present invention is based on the expectation that a quinolinylmethanols have beneficial effects on malaria and other infectious diseases and do not require penetration into the brain. To this end, the present invention provides compounds that are designed to preferentially target parasites and bacteria in peripheral tissues (e.g., blood and liver), while remaining outside the brain. Peripherally-mediated beneficial effects of anti-malarial/anti-infective agents should be maintained, whereas CNS side effects should be reduced or eliminated.

The compounds of the present invention have been designed to have reduced CNS exposure by virtue of their inability or limited ability to penetrate the blood-brain barrier (BBB), or by their participation in active transport efflux systems, thus reducing centrally mediated side-effects, a potential problem with anti-malarial agents such as mefloquine (mefloquine Structure AA, $X=2\text{-}CF_3$, $X'=8\text{-}CF_3$, $Y=H$, and $D=2\text{-}piperidinyl$).

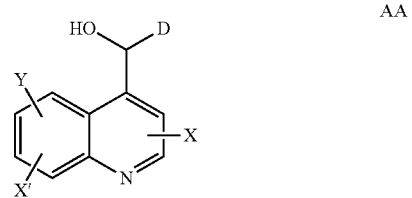

AA

It is expected that the peripherally restricted compounds of the present invention will have no or very limited CNS effects, including hallucinations, delusional thinking, convulsions, depression, anxiety, paranoia, aggression, nightmares, insomnia, peripheral motor-sensory neuropathy, vestibular (balance) damage, suicidal ideation, and symptoms of traumatic brain injury. Thus, their peripherally mediated anti-malarial/anti-infective effects should provide therapeutic agents with greater safety.

Moreover, if the maximum dosage of a drug used in the treatment of malaria or other systemic infections is limited as a result of CNS side effects, incorporation of a peripherally restricting group in such a drug should lower the brain concentration of the drug relative to the concentration in the systemic circulation, thereby affording the opportunity to increase the dosage employed to treat the peripheral disorder. The increased dosage may provide greater therapeutic efficacy, as well as a more rapid onset of therapeutic action.

Thus, in an aspect, the present invention provides novel compounds of formula AA or a stereoisomer or pharmaceutically acceptable salt thereof:

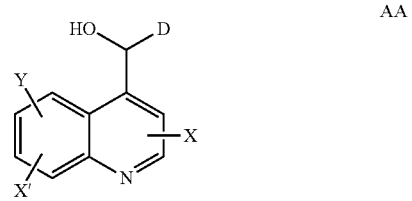

AA wherein:
D is selected from

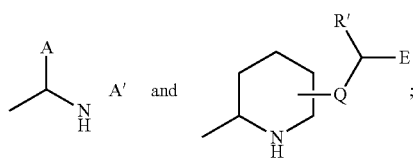

A is selected from H, $C_{1-4}$ alkyl, $(CH_2)_n CONHOH$, $(CH_2)_n CH_2 CONHA'$, and $(CH_2)_n CO_2 R$;
n is selected from 0, 1, 2, 3, and 4;
A' is selected from H and CR'R"Z;
Q is selected from O, NR, and $CH_2 NR$;
R at each occurrence is independently selected from H and $C_{1-4}$ alkyl;

R' is selected from H, $C_{1-4}$ alkyl, $C_{3-6}$-cycloalkyl, $C_{1-4}$ hydroxyalkyl, phenyl, benzyl, —$C_{0-4}$ alkyl-$CO_2R$, —$C_{0-4}$ alkyl-$CONHR^a$, —$C_{0-4}$ alkyl-CONHOH, —$C_{0-4}$ alkyl-C(NH)$NH_2$;

$R^a$ is selected from H and —$C_{1-4}$ alkyl-$CONHR^b$;

$R^b$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$;

R" is selected from H, $C_{1-4}$ alkyl or together with R' forms a $C_3$-$C_6$ cycloalkyl group;

E is selected from —$C_{1-4}$ alkyl-NHA', —$C_{0-4}$ alkyl-CONHA', —$C_{0-4}$ alkyl-CONHOH, —$C_{0-4}$ alkyl-$CO_2R$, —$C_{0-4}$ alkyl-PO(OR)$_2$, —$C_{0-4}$ alkyl-$SO_2OR$, —$C_{0-4}$ alkyl-$SO_2NH_2$, and —$C_{0-4}$ alkyl-(NH)$NH_2$;

X is selected from H, halo, —CN, O—$C_{1-4}$ alkyl, and $CF_3$;
X' is selected from H, halo, —CN, O—$C_{1-4}$ alkyl, and $CF_3$;
Y is selected from H, halo, —CN, O—$C_{1-4}$ alkyl, and $CF_3$;
Z is selected from H, $C_{1-4}$ alkyl, $C_{1-4}$ hydroxyalkyl, $C_{2-4}$ alkenyl, $C_{2-4}$ alkynyl, phenyl, phenyl-$C_{1-6}$ alkyl-, —$C_{0-4}$ alkyl-$CO_2R$, —$C_{0-4}$ alkyl-$CONHR^c$, —$C_{0-4}$ alkyl-CONHOH, —$C_{0-4}$ alkyl-C(NH)$NH_2$, $CHOHCH_2CO_2R$, $CHOHCH_2CONHR^c$, $CHOHCH_2C(NH)NHR^c$, $CH_2CHOHCO_2R$, $CH_2CHOHCONHR^c$, $CH_2CHOHC(NH)NH_2$, CH=$CHCO_2R$, CH=CHCONHQ, CH=CHC(NH)$NH_2$, —$C_{1-4}$ alkyl-$SO_3R$, and —$C_{1-4}$ alkyl-$SO_2NHR^c$;

$R^c$ is selected from H, —$C_{1-4}$ alkyl-$CONHR^d$, $CHOHCH_2CONHR^d$, $CH_2CHOHCONHR^d$, and —$C_{1-4}$ alkyl-$SO_2NHR^d$;

$R^d$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$;

wherein each aryl group is optionally substituted with 1-2 groups selected from $CF_3$, halogen, $C_{1-4}$ alkyl, —CN, $CONR_2$, $NO_2$, $NR_2$, OR, $NHSO_2CH_3$, and $SO_2NHR$; and, wherein at least one of A, A', D, R, R', E, and Z is a functionality that reduces or eliminates the brain penetration of the compound of formula AA.

In another aspect, the present invention provides novel compounds of formula $AA_1$ or a stereoisomer or pharmaceutically acceptable salt thereof:

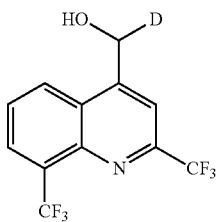

AA$_1$ wherein:
D is selected from

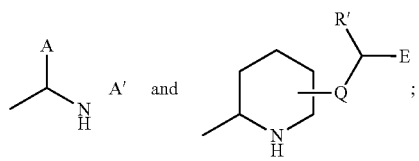

A is selected from H, $C_{1-4}$ alkyl, $(CH_2)_n CONHA'$, $(CH_2)_n CONHOH$, and $(CH_2)_n CO_2R$;
n is selected from 0, 1, 2, 3, and 4;

A' is selected from H and CR'R"Z;
Q is selected from O and $CH_2NR$;
R at each occurrence is independently selected from H and $C_{1-4}$ alkyl;

R' is selected from H, $C_{1-4}$ alkyl, $C_{3-6}$-cycloalkyl, $C_{1-4}$ hydroxyalkyl, phenyl, benzyl, —$C_{0-4}$ alkyl-$CO_2R$, —$C_{0-4}$ alkyl-$CONHR^a$, —$C_{0-4}$ alkyl-CONHOH, and —$C_{0-4}$ alkyl-C(NH)$NH_2$;

$R^a$ is selected from H and —$C_{1-4}$ alkyl-$CONHR^b$;

$R^b$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$;

R" is selected from H and $C_{1-4}$ alkyl;
alternatively, R' and R" together form a $C_{3-6}$ cycloalkyl group;

E is selected from —$C_{1-4}$ alkyl-NHA', —$C_{0-4}$ alkyl-CONHA', —$C_{0-4}$ alkyl-CONHOH, —$C_{0-4}$ alkyl-$CO_2R$, —$C_{0-4}$ alkyl-PO(OR)$_2$, —$C_{0-4}$ alkyl-$SO_2OR$, —$C_{0-4}$ alkyl-$SO_2NH_2$, and —$C_{0-4}$ alkyl-(NH)$NH_2$;

Z is selected from H, $C_{1-4}$ alkyl, $C_{1-4}$ hydroxyalkyl, $C_{2-4}$ alkenyl, $C_{2-4}$ alkynyl, phenyl, phenyl-$C_{1-6}$ alkyl-, —$C_{0-4}$ alkyl-$CO_2R$, —$C_{0-4}$ alkyl-$CONHR^c$, —$C_{0-4}$ alkyl-C(NH)$NH_2$, —$C_{0-4}$ alkyl-CONHOH, $CHOHCH_2CO_2R$, $CHOHCH_2CONHR^c$, $CHOHCH_2C(NH)NH_2$, $CH_2CHOHCO_2R$, $CH_2CHOHCONHR^c$, $CH_2CHOHC(NH)NH_2$, CH=$CHCO_2R$, CH=CHCONHQ, CH=CHC(NH)$NH_2$, —$C_{1-4}$ alkyl-$SO_3R$, and —$C_{1-4}$ alkyl-$SO_2NHR^c$;

$R^c$ is selected from H, —$C_{1-4}$ alkyl-$CONHR^d$, $CHOHCH_2CONHR^d$, $CH_2CHOHCONHR^d$, and —$C_{1-4}$ alkyl-$SO_2NHR^d$;

$R^d$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$; and, each phenyl or benzyl group is independently optionally substituted with 1-2 groups selected from $CF_3$, halogen, $C_{1-4}$ alkyl, —CN, $CONR_2$, $NO_2$, $NR_2$, OR, $NHSO_2CH_3$, and SONHR.

[1] In another aspect, the present invention provides novel compounds of formula A or a stereoisomer or pharmaceutically acceptable salt thereof:

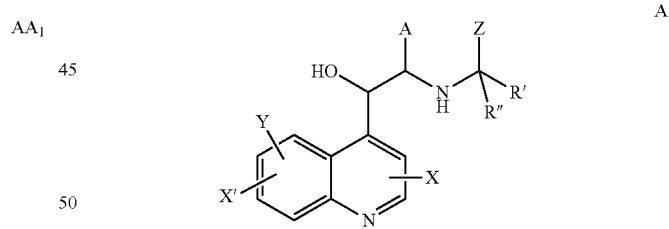

A wherein:
A is selected from H, $(CH_2)_n CONHA'$, $(CH_2)_n CONHOH$, and $(CH_2)_n CO_2R$;
n is selected from 0, 1, 2, 3, and 4;
A' is selected from H and CR'R"Z;
R at each occurrence is independently selected from H and $C_{1-4}$ alkyl;
R' is selected from H, $C_{1-4}$ alkyl, $C_{3-6}$-cycloalkyl, $C_{1-4}$ hydroxyalkyl, phenyl, benzyl, —$C_{0-4}$ alkyl-$CO_2R$, —$C_{0-4}$ alkyl-$CONHR^a$, —$C_{0-4}$ alkyl-CONHOH, and —$C_{0-4}$ alkyl-C(NH)$NH_2$;
$R^a$ is selected from H and —$C_{1-4}$ alkyl-$CONHR^b$;
$R^b$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$;

R" is selected from H and $C_{1-4}$ alkyl;

alternatively, R' and R" together form a $C_{3-6}$ cycloalkyl group;

X is selected from H, halo, —CN, O—$C_{1-4}$ alkyl, $C_{2-4}$ alkenyl, $CF_3$, and phenyl;

X' is selected from H, halo, —CN, O—$C_{1-4}$ alkyl, $C_{2-4}$ alkenyl, and $CF_3$;

Y is selected from H, halo, —CN, O—$C_{1-4}$ alkyl, $C_{2-4}$ alkenyl, and $CF_3$;

Z is selected from H, $C_{1-4}$ alkyl, $C_{1-4}$ hydroxyalkyl, $C_{2-4}$ alkenyl, $C_{2-4}$ alkynyl, phenyl, phenyl-$C_{1-6}$ alkyl-, —$C_{0-4}$ alkyl-$CO_2R$, —$C_{0-4}$ alkyl-$CONHR^c$, —$C_{0-4}$ alkyl-CONHOH, —$C_{0-4}$ alkyl-C(NH)$NH_2$, $CHOHCH_2CO_2R$, $CHOHCH_2CONHR^c$, $CHOHCH_2C(NH)NH_2$, $CH_2CHOHCO_2R$, $CH_2CHOHCONHR^c$, $CH_2CHOHC(NH)NH_2$, CH=CHCO$_2$R, CH=CHCONHQ, CH=CHC(NH)NH$_2$, —$C_{1-4}$ alkyl-$SO_3R$, and —$C_{1-4}$ alkyl-$SO_2NHR^c$;

$R^c$ is selected from H, —$C_{1-4}$ alkyl-CONHR$^d$, $CHOHCH_2CONHR^d$, $CH_2CHOHCONHR^d$, and —$C_{1-4}$ alkyl-$SO_2NHR^d$;

$R^d$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$; and, each phenyl or benzyl group is independently optionally substituted with 1-2 groups selected from $CF_3$, halogen, $C_{1-4}$ alkyl, —CN, $CONR_2$, $NO_2$, $NR_2$, OR, $NHSO_2CH_3$, and SONHR;

provided that when A=H, then one of R' and Z is other than H, $C_{1-4}$ alkyl, $C_{2-4}$ alkenyl, $C_{2-4}$ alkynyl, $C_{3-6}$-cycloalkyl, $C_{1-4}$ hydroxyalkyl, phenyl, and phenyl-$C_{1-6}$ alkyl-.

[2] In another aspect, the present invention provides novel compounds of formula I or a stereoisomer or pharmaceutically acceptable salt thereof:

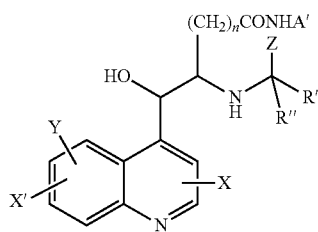

I wherein:

n is selected from 0, 1, 2, 3, and 4;

A' is selected from H and CR'R"Z;

R at each occurrence is independently selected from H and $C_{1-4}$ alkyl;

R' is selected from H, $C_{1-4}$ alkyl, $C_{3-6}$-cycloalkyl, $C_{1-4}$ hydroxyalkyl, phenyl, benzyl, —$C_{0-4}$ alkyl-$CO_2R$, —$C_{0-4}$ alkyl-CONHR$^a$, —$C_{0-4}$ alkyl-CONHOH, and —$C_{0-4}$ alkyl-C(NH)$NH_2$;

$R^a$ is selected from H and —$C_{1-4}$ alkyl-CONHR$^b$;

$R^b$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$;

R" is selected from H and $C_{1-4}$ alkyl;

alternatively, R' and R" together form a $C_{3-6}$ cycloalkyl group;

X is selected from H, halo, —CN, O—$C_{1-4}$ alkyl, $C_{2-4}$ alkenyl, $CF_3$, and phenyl;

X' is selected from H, halo, —CN, O—$C_{1-4}$ alkyl, $C_{2-4}$ alkenyl, and $CF_3$;

Y is selected from H, halo, —CN, O—$C_{1-4}$ alkyl, $C_{2-4}$ alkenyl, and $CF_3$;

Z is selected from H, $C_{1-4}$ alkyl, $C_{1-4}$ hydroxyalkyl, $C_{2-4}$ alkenyl, $C_{2-4}$ alkynyl, phenyl, phenyl-$C_{1-6}$ alkyl-, —$C_{0-4}$ alkyl-$CO_2R$, —$C_{0-4}$ alkyl-$CONHR^c$, —$C_{0-4}$ alkyl-CONHOH, —$C_{0-4}$ alkyl-C(NH)$NH_2$, $CHOHCH_2CO_2R$, $CHOHCH_2CONHR^c$, $CHOHCH_2C(NH)NH_2$, $CH_2CHOHCO_2R$, $CH_2CHOHCONHR^c$, $CH_2CHOHC(NH)NH_2$, CH=CHCO$_2$R, CH=CHCONHQ, CH=CHC(NH)NH$_2$, —$C_{1-4}$ alkyl-$SO_3R$, and —$C_{1-4}$ alkyl-$SO_2NHR^c$;

$R^c$ is selected from H, —$C_{1-4}$ alkyl-CONHR$^d$, $CHOHCH_2CONHR^d$, $CH_2CHOHCONHR^d$, and —$C_{1-4}$ alkyl-$SO_2NHR^d$;

$R^d$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$; and, each phenyl or benzyl group is independently optionally substituted with 1-2 groups selected from $CF_3$, halogen, $C_{1-4}$ alkyl, —CN, $CONR_2$, $NO_2$, $NR_2$, OR, $NHSO_2CH_3$, and SONHR.

In another aspect, the present invention provides novel compounds of formula $I_A$ or a stereoisomer or pharmaceutically acceptable salt thereof:

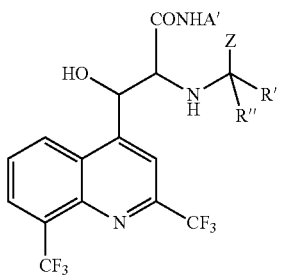

$I_A$ wherein:

A' is selected from H and CR'R"Z;

R at each occurrence is independently selected from H and $C_{1-4}$ alkyl;

R' is selected from H, $C_{1-4}$ alkyl, $C_{3-6}$-cycloalkyl, $C_{1-4}$ hydroxyalkyl, phenyl, benzyl, —$C_{0-4}$ alkyl-$CO_2R$, —$C_{0-4}$ alkyl-CONHR$^a$, —$C_{0-4}$ alkyl-CONHOH, and —$C_{0-4}$ alkyl-C(NH)$NH_2$;

$R^a$ is selected from H and —$C_{1-4}$ alkyl-CONHR$^b$;

$R^b$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$;

R" is selected from H and $C_{1-4}$ alkyl;

alternatively, R' and R" together form a $C_{3-6}$ cycloalkyl group;

Z is selected from H, $C_{1-4}$ alkyl, $C_{1-4}$ hydroxyalkyl, $C_{2-4}$ alkenyl, $C_{2-4}$ alkynyl, phenyl, phenyl-$C_{1-6}$ alkyl-, —$C_{0-4}$ alkyl-$CO_2R$, —$C_{0-4}$ alkyl-$CONHR^c$, —$C_{0-4}$ alkyl-C(NH)$NH_2$, —$C_{0-4}$ alkyl-CONHOH, $CHOHCH_2CO_2R$, $CHOHCH_2CONHR^c$, $CHOHCH_2C(NH)NH_2$, $CH_2CHOHCO_2R$, $CH_2CHOHCONHR^c$, $CH_2CHOHC(NH)NH_2$, CH=CHCO$_2$R, CH=CHCONHQ, CH=CHC(NH)NH$_2$, —$C_{1-4}$ alkyl-$SO_3R$, and —$C_{1-4}$ alkyl-$SO_2NHR^c$;

$R^c$ is selected from H, —$C_{1-4}$ alkyl-CONHR$^d$, $CHOHCH_2CONHR^d$, $CH_2CHOHCONHR^d$, and —$C_{1-4}$ alkyl-$SO_2NHR^d$;

$R^d$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$;

each phenyl or benzyl group is independently optionally substituted with 1-2 groups selected from $CF_3$, halogen, $C_{1-4}$ alkyl, —CN, $CONR_2$, $NO_2$, $NR_2$, OR, $NHSO_2CH_3$, and SONHR.

[4] In another aspect, the present invention provides novel compounds of formula $I_B$ or a stereoisomer or pharmaceutically acceptable salt thereof:

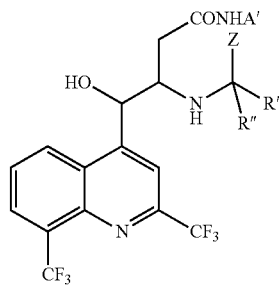

wherein:
A' is selected from H and CR'R"Z;
R at each occurrence is independently selected from H and $C_{1-4}$ alkyl;
R' is selected from H, $C_{1-4}$ alkyl, $C_{3-6}$-cycloalkyl, $C_{1-4}$ hydroxyalkyl, phenyl, benzyl, —$C_{0-4}$ alkyl-$CO_2R$, —$C_{0-4}$ alkyl-$CONHR^a$, —$C_{0-4}$ alkyl-CONHOH, and —$C_{0-4}$ alkyl-C(NH)$NH_2$;
$R^a$ is selected from H and —$C_{1-4}$ alkyl-$CONHR^b$;
$R^b$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$;
R" is selected from H and $C_{1-4}$ alkyl;
alternatively, R' and R" together form a $C_{3-6}$ cycloalkyl group;
Z is selected from H, $C_{1-4}$ alkyl, $C_{1-4}$ hydroxyalkyl, $C_{2-4}$ alkenyl, $C_{2-4}$ alkynyl, phenyl, phenyl-$C_{1-6}$ alkyl-, —$C_{0-4}$ alkyl-$CO_2R$, —$C_{0-4}$ alkyl-$CONHR^c$, —$C_{0-4}$ alkyl-C(NH)$NH_2$, —$C_{0-4}$ alkyl-CONHOH, $CHOHCH_2CO_2R$, $CHOHCH_2CONHR^c$, $CHOHCH_2C(NH)NH_2$, $CH_2CHOHCO_2R$, $CH_2CHOHCONHR^c$, $CH_2CHOHC(NH)NH_2$, CH=$CHCO_2R$, CH=CHCONHQ, CH=CHC(NH)$NH_2$, —$C_{1-4}$ alkyl-$SO_3R$, and —$C_{1-4}$ alkyl-$SO_2NHR^c$;
$R^c$ is selected from H, —$C_{1-4}$ alkyl-$CONHR^d$, $CHOHCH_2CONHR^d$, $CH_2CHOHCONHR^d$, and —$C_{1-4}$ alkyl-$SO_2NHR^d$;
$R^d$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$;
each phenyl or benzyl group is independently optionally substituted with 1-2 groups selected from $CF_3$, halogen, $C_{1-4}$ alkyl, —CN, $CONR_2$, $NO_2$, $NR_2$, OR, $NHSO_2CH_3$, and SONHR.

[5] In another aspect, the present invention provides novel compounds of formula II or a stereoisomer or pharmaceutically acceptable salt thereof:

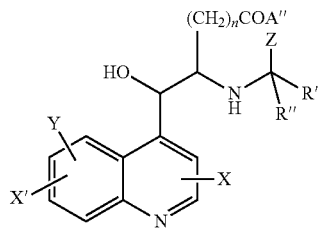

wherein:
n is selected from 0, 1, 2, 3, and 4;
A" is selected from OH, NHOH, and $OC_{1-4}$ alkyl;
R at each occurrence is independently selected from H and $C_{1-4}$ alkyl;
R' is selected from H, $C_{1-4}$ alkyl, $C_{3-6}$-cycloalkyl, $C_{1-4}$ hydroxyalkyl, phenyl, benzyl, —$C_{0-4}$ alkyl-$CO_2R$, —$C_{0-4}$ alkyl-$CONHR^a$, —$C_{0-4}$ alkyl-CONHOH, and —$C_{0-4}$ alkyl-C(NH)$NH_2$;
$R^a$ is selected from H and —$C_{1-4}$ alkyl-$CONHR^b$;
$R^b$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$
R" is selected from H and $C_{1-4}$ alkyl;
alternatively, R' and R" together form a $C_{3-6}$ cycloalkyl group;
X is selected from H, halo, —CN, O—$C_{1-4}$ alkyl, and $CF_3$, and phenyl;
X' is selected from H, halo, —CN, O—$C_{1-4}$ alkyl, and $CF_3$;
Y is selected from H, halo, —CN, O—$C_{1-4}$ alkyl, and $CF_3$;
Z is selected from H, $C_{1-4}$ alkyl, $C_{1-4}$ hydroxyalkyl, $C_{2-4}$ alkenyl, $C_{2-4}$ alkynyl, phenyl, phenyl-$C_{1-6}$ alkyl-, —$C_{0-4}$ alkyl-$CO_2R$, —$C_{0-4}$ alkyl-$CONHR^c$, —$C_{0-4}$ alkyl-C(NH)$NH_2$, —$C_{0-4}$ alkyl-CONHOH, $CHOHCH_2CO_2R$, $CHOHCH_2CONHR^c$, $CHOHCH_2C(NH)NH_2$, $CH_2CHOHCO_2R$, $CH_2CHOHCONHR^c$, $CH_2CHOHC(NH)NH_2$, CH=$CHCO_2R$, CH=CHCONHQ, CH=CHC(NH)$NH_2$, —$C_{1-4}$ alkyl-$SO_3R$, and —$C_{1-4}$ alkyl-$SO_2NHR^c$;
$R^c$ is selected from H, —$C_{1-4}$ alkyl-$CONHR^d$, $CHOHCH_2CONHR^d$, $CH_2CHOHCONHR^d$, and —$C_{1-4}$ alkyl-$SO_2NHR^d$;
$R^d$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$; and,
each phenyl or benzyl group is independently optionally substituted with 1-2 groups selected from $CF_3$, halogen, $C_{1-4}$ alkyl, —CN, $CONR_2$, $NO_2$, $NR_2$, OR, $NHSO_2CH_3$, and SONHR.

[6] In another aspect, the present invention provides novel compounds of formula III or a stereoisomer or pharmaceutically acceptable salt thereof:

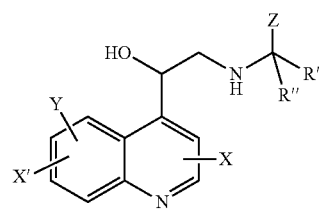

wherein:
R at each occurrence is independently selected from H and $C_{1-4}$ alkyl;
R' is selected from H, $C_{1-4}$ alkyl, $C_{3-6}$-cycloalkyl, $C_{1-4}$ hydroxyalkyl, phenyl, benzyl, —$C_{0-4}$ alkyl-$CO_2R$, —$C_{0-4}$ alkyl-$CONHR^a$, —$C_{0-4}$ alkyl-CONHOH, and —$C_{0-4}$ alkyl-C(NH)$NH_2$;
$R^a$ is selected from H and —$C_{1-4}$ alkyl-$CONHR^b$;
$R^b$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$;
R" is selected from H and $C_{1-4}$ alkyl;
alternatively, R' and R" together form a $C_{3-6}$ cycloalkyl group;
X is selected from H, halo, —CN, O—$C_{1-4}$ alkyl, and $CF_3$, and phenyl;
X' is selected from H, halo, —CN, O—$C_{1-4}$ alkyl, and $CF_3$;
Y is selected from H, halo, —CN, O—$C_{1-4}$ alkyl, and $CF_3$;

Z is selected from H, $C_{1-4}$ alkyl, $C_{1-4}$ hydroxyalkyl, $C_{2-4}$ alkenyl, $C_{2-4}$ alkynyl, phenyl, phenyl-$C_{1-6}$ alkyl-, —$C_{0-4}$ alkyl-$CO_2R$, —$C_{0-4}$ alkyl-$CONHR^c$, —$C_{0-4}$ alkyl-$C(NH)NH_2$, —$C_{0-4}$ alkyl-CONHOH, $CHOHCH_2CO_2R$, $CHOHCH_2CONHR^c$, $CHOHCH_2C(NH)NH_2$, $CH_2CHOHCO_2R$, $CH_2CHOHCONHR^c$, $CH_2CHOHC(NH)NH_2$, CH=$CHCO_2R$, CH=CHCONHQ, CH=CHC(NH)$NH_2$, —$C_{1-4}$ alkyl-$SO_3R$, and —$C_{1-4}$ alkyl-$SO_2NHR^c$;

$R^c$ is selected from H, —$C_{1-4}$ alkyl-$CONHR^d$, $CHOHCH_2CONHR^d$, $CH_2CHOHCONHR^d$, and —$C_{1-4}$ alkyl-$SO_2NHR^d$;

$R^d$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$; and, each phenyl or benzyl group is independently optionally substituted with 1-2 groups selected from $CF_3$, halogen, $C_{1-4}$ alkyl, —CN, $CONR_2$, $NO_2$, $NR_2$, OR, $NHSO_2CH_3$, and SONHR.

[7] In another aspect, the present invention provides novel compounds of formula $III_A$ or a stereoisomer or pharmaceutically acceptable salt thereof:

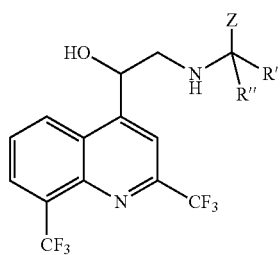

$III_A$ wherein:

R at each occurrence is independently selected from H and $C_{1-4}$ alkyl;

R' is selected from H, $C_{1-4}$ alkyl, $C_{3-6}$-cycloalkyl, $C_{1-4}$ hydroxyalkyl, phenyl, benzyl, —$C_{0-4}$ alkyl-$CO_2R$, —$C_{0-4}$ alkyl-$CONHR^a$, —$C_{0-4}$ alkyl-CONHOH, and —$C_{0-4}$ alkyl-C(NH)$NH_2$;

$R^a$ is selected from H and —$C_{1-4}$ alkyl-$CONHR^b$;

$R^b$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$;

R" is selected from H and $C_{1-4}$ alkyl;

alternatively, R' and R" together form a $C_{3-6}$ cycloalkyl group;

Z is selected from H, $C_{1-4}$ alkyl, $C_{1-4}$ hydroxyalkyl, $C_{2-4}$ alkenyl, $C_{2-4}$ alkynyl, phenyl, phenyl-$C_{1-6}$ alkyl-, —$C_{0-4}$ alkyl-$CO_2R$, —$C_{0-4}$ alkyl-$CONHR^c$, —$C_{0-4}$ alkyl-$C(NH)NH_2$, —$C_{0-4}$ alkyl-CONHOH, $CHOHCH_2CO_2R$, $CHOHCH_2CONHR^c$, $CHOHCH_2C(NH)NH_2$, $CH_2CHOHCO_2R$, $CH_2CHOHCONHR^c$, $CH_2CHOHC(NH)NH_2$, CH=$CHCO_2R$, CH=CHCONHQ, CH=CHC(NH)$NH_2$, —$C_{1-4}$ alkyl-$SO_3R$, and —$C_{1-4}$ alkyl-$SO_2NHR^c$;

$R^c$ is selected from H, —$C_{1-4}$ alkyl-$CONHR^d$, $CHOHCH_2CONHR^d$, $CH_2CHOHCONHR^d$, and —$C_{1-4}$ alkyl-$SO_2NHR^d$;

$R^d$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$;

each phenyl or benzyl group is independently optionally substituted with 1-2 groups selected from $CF_3$, halogen, $C_{1-4}$ alkyl, —CN, $CONR_2$, $NO_2$, $NR_2$, OR, $NHSO_2CH_3$, and SONHR.

[8] In another aspect, the present invention provides novel compounds of formula IV or a stereoisomer or pharmaceutically acceptable salt thereof:

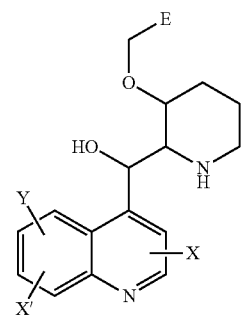

IV wherein:

E is selected from —$C_{1-4}$ alkyl-NHA', —$C_{0-4}$ alkyl-CONHA', —$C_{0-4}$ alkyl-CONHOH, —$C_{0-4}$ alkyl-$CO_2R$, —$C_{0-4}$ alkyl-PO(OR)$_2$, —$C_{0-4}$ alkyl-$SO_2OR$, —$C_{0-4}$ alkyl-$SO_2NH_2$, and —$C_{1-4}$ alkyl-(NH)$NH_2$;

A' is selected from H and CR'R"Z;

R at each occurrence is independently selected from H and $C_{1-4}$ alkyl;

R' is selected from H, $C_{1-4}$ alkyl, $C_{3-6}$-cycloalkyl, $C_{1-4}$ hydroxyalkyl, phenyl, benzyl, —$C_{0-4}$ alkyl-$CO_2R$, —$C_{0-4}$ alkyl-$CONHR^a$, —$C_{0-4}$ alkyl-CONHOH, and —$C_{0-4}$ alkyl-C(NH)$NH_2$;

$R^a$ is selected from H and —$C_{1-4}$ alkyl-$CONHR^b$;

$R^b$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$;

R" is selected from H and $C_{1-4}$ alkyl;

alternatively, R' and R" together form a $C_{3-6}$ cycloalkyl group;

X is selected from H, halo, —CN, O—$C_{1-4}$ alkyl, and $CF_3$, and phenyl;

X' is selected from H, halo, —CN, O—$C_{1-4}$ alkyl, and $CF_3$;

Y is selected from H, halo, —CN, O—$C_{1-4}$ alkyl, and $CF_3$;

Z is selected from H, $C_{1-4}$ alkyl, $C_{1-4}$ hydroxyalkyl, $C_{2-4}$ alkenyl, $C_{2-4}$ alkynyl, phenyl, phenyl-$C_{1-6}$ alkyl-, —$C_{0-4}$ alkyl-$CO_2R$, —$C_{0-4}$ alkyl-$CONHR^c$, —$C_{0-4}$ alkyl-$C(NH)NH_2$, —$C_{0-4}$ alkyl-CONHOH, $CHOHCH_2CO_2R$, $CHOHCH_2CONHR^c$, $CHOHCH_2C(NH)NH_2$, $CH_2CHOHCO_2R$, $CH_2CHOHCONHR^c$, $CH_2CHOHC(NH)NH_2$, CH=$CHCO_2R$, CH=CHCONHQ, CH=CHC(NH)$NH_2$, —$C_{1-4}$ alkyl-$SO_3R$, and —$C_{1-4}$ alkyl-$SO_2NHR^c$;

$R^c$ is selected from H, —$C_{1-4}$ alkyl-$CONHR^d$, $CHOHCH_2CONHR^d$, $CH_2CHOHCONHR^d$, and —$C_{1-4}$ alkyl-$SO_2NHR^d$;

$R^d$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$;

each phenyl or benzyl group is independently optionally substituted with 1-2 groups selected from $CF_3$, halogen, $C_{1-4}$ alkyl, —CN, $CONR_2$, $NO_2$, $NR_2$, OR, $NHSO_2CH_3$, and SONHR.

[9] In another aspect, the present invention provides novel compounds of formula IV$_A$ or a stereoisomer or pharmaceutically acceptable salt thereof:

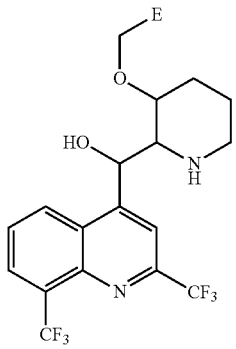

IV$_A$ wherein:

A' is selected from H and CR'R"Z;

E is selected from —C$_{1-4}$ alkyl-NHA', —C$_{1-4}$ alkyl-CONHA', —C$_{0-4}$ alkyl-CONHOH, —C$_{0-4}$ alkyl-CO$_2$R, —C$_{0-4}$ alkyl-PO(OR)$_2$, —C$_{0-4}$ alkyl-SO$_2$OR, —C$_{0-4}$ alkyl-SO$_2$NH$_2$, and —C$_{0-4}$ alkyl-(NH)NH$_2$;

R at each occurrence is independently selected from H and C$_{1-4}$ alkyl;

R' is selected from H, C$_{1-4}$ alkyl, C$_{3-6}$-cycloalkyl, C$_{1-4}$ hydroxyalkyl, phenyl, benzyl, —C$_{0-4}$ alkyl-CO$_2$R, —C$_{0-4}$ alkyl-CONHR$^a$, —C$_{0-4}$ alkyl-CONHOH, and —C$_{0-4}$ alkyl-C(NH)NH$_2$;

R$^a$ is selected from H and —C$_{1-4}$ alkyl-CONHR$^b$;

R$^b$ is selected from C$_{1-4}$ alkyl, C$_{1-4}$ hydroxyalkyl, C$_{3-4}$ alkenyl, C$_{3-4}$ alkynyl, phenyl, phenyl-C$_{1-6}$ alkyl-, and —C$_{1-4}$ alkyl-CONH$_2$;

R" is selected from H and C$_{1-4}$ alkyl;

alternatively, R' and R" together form a C$_{3-6}$ cycloalkyl group;

Z is selected from H, C$_{1-4}$ alkyl, C$_{1-4}$ hydroxyalkyl, C$_{2-4}$ alkenyl, C$_{2-4}$ alkynyl, phenyl, phenyl-C$_{1-6}$ alkyl-, —C$_{0-4}$ alkyl-CO$_2$R, —C$_{0-4}$ alkyl-CONHR$^c$, —C$_{0-4}$ alkyl-C(NH)NH$_2$, —C$_{0-4}$ alkyl-CONHOH, CHOHCH$_2$CO$_2$R, CHOHCH$_2$CONHR$^c$, CHOHCH$_2$C(NH)NH$_2$, CH$_2$CHOHCO$_2$R, CH$_2$CHOHCONHR$^c$, CH$_2$CHOHC(NH)NH$_2$, CH=CHCO$_2$R, CH=CHCONHQ, CH=CHC(NH)NH$_2$, —C$_{1-4}$ alkyl-SO$_3$R, and —C$_{1-4}$ alkyl-SO$_2$NHR$^c$;

R$^c$ is selected from H, —C$_{1-4}$ alkyl-CONHR$^d$, CHOHCH$_2$CONHR$^d$, CH$_2$CHOHCONHR$^d$, and —C$_{1-4}$ alkyl-SO$_2$NHR$^d$;

R$^d$ is selected from C$_{1-4}$ alkyl, C$_{1-4}$ hydroxyalkyl, C$_{3-4}$ alkenyl, C$_{3-4}$ alkynyl, phenyl, phenyl-C$_{1-6}$ alkyl-, and —C$_{1-4}$ alkyl-CONH$_2$; and, each phenyl or benzyl group is independently optionally substituted with 1-2 groups selected from CF$_3$, halogen, C$_{1-4}$ alkyl, —CN, CONR$_2$, NO$_2$, NR$_2$, OR, NHSO$_2$CH$_3$, and SONHR.

[10] In another aspect, the present invention provides novel compounds of formula V or a stereoisomer or pharmaceutically acceptable salt thereof:

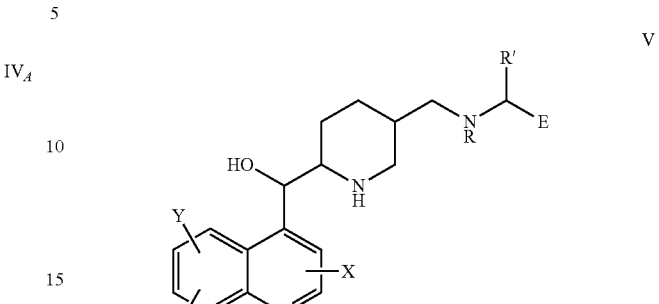

V wherein:

E is selected from —C$_{1-4}$ alkyl-NHA', —C$_{0-4}$ alkyl-CONHA', —C$_{0-4}$ alkyl-CONHOH, —C$_{0-4}$ alkyl-CO$_2$R, —C$_{0-4}$ alkyl-PO(OR)$_2$, —C$_{0-4}$ alkyl-SO$_2$OR, —C$_{0-4}$ alkyl-SO$_2$NH$_2$, and —C$_{0-4}$ alkyl-(NH)NH$_2$;

A' is selected from H and CR'R"Z;

R at each occurrence is independently selected from H and C$_{1-4}$ alkyl;

R' is selected from H, C$_{1-4}$ alkyl, C$_{3-6}$-cycloalkyl, C$_{1-4}$ hydroxyalkyl, phenyl, benzyl, —C$_{0-4}$ alkyl-CO$_2$R, —C$_{0-4}$ alkyl-CONHR$^a$, —C$_{0-4}$ alkyl-CONHOH, and —C$_{0-4}$ alkyl-C(NH)NH$_2$;

R$^a$ is selected from H and —C$_{1-4}$ alkyl-CONHR$^b$;

R$^b$ is selected from C$_{1-4}$ alkyl, C$_{1-4}$ hydroxyalkyl, C$_{3-4}$ alkenyl, C$_{3-4}$ alkynyl, phenyl, phenyl-C$_{1-6}$ alkyl-, and —C$_{1-4}$ alkyl-CONH$_2$;

R" is selected from H and C$_{1-4}$ alkyl;

alternatively, R' and R" together form a C$_{3-6}$ cycloalkyl group;

X is selected from H, halo, —CN, O—C$_{1-4}$ alkyl, and CF$_3$, and phenyl, wherein the phenyl is substituted with 0-1 X';

X' is selected from H, halo, —CN, O—C$_{1-4}$ alkyl, and CF$_3$;

Y is selected from H, halo, —CN, O—C$_{1-4}$ alkyl, and CF$_3$; and,

Z is selected from H, C$_{1-4}$ alkyl, C$_{1-4}$ hydroxyalkyl, C$_{2-4}$ alkenyl, C$_{2-4}$ alkynyl, phenyl, phenyl-C$_{1-6}$ alkyl-, —C$_{0-4}$ alkyl-CO$_2$R, —C$_{0-4}$ alkyl-CONHR$^c$, —C$_{0-4}$ alkyl-C(NH)NH$_2$, —C$_{0-4}$ alkyl-CONHOH, CHOHCH$_2$CO$_2$R, CHOHCH$_2$CONHR$^c$, CHOHCH$_2$C(NH)NH$_2$, CH$_2$CHOHCO$_2$R, CH$_2$CHOHCONHR$^c$, CH$_2$CHOHC(NH)NH$_2$, CH=CHCO$_2$R, CH=CHCONHQ, CH=CHC(NH)NH$_2$, —C$_{1-4}$ alkyl-SO$_3$R, and —C$_{1-4}$ alkyl-SO$_2$NHR$^c$;

R$^c$ is selected from H, —C$_{1-4}$ alkyl-CONHR$^d$, CHOHCH$_2$CONHR$^d$, CH$_2$CHOHCONHR$^d$, and —C$_{1-4}$ alkyl-SO$_2$NHR$^d$;

R$^d$ is selected from C$_{1-4}$ alkyl, C$_{1-4}$ hydroxyalkyl, C$_{3-4}$ alkenyl, C$_{3-4}$ alkynyl, phenyl, phenyl-C$_{1-6}$ alkyl-, and —C$_{1-4}$ alkyl-CONH$_2$;

each phenyl or benzyl group is independently optionally substituted with 1-2 groups selected from CF$_3$, halogen, C$_{1-4}$ alkyl, —CN, CONR$_2$, NO$_2$, NR$_2$, OR, NHSO$_2$CH$_3$, and SONHR.

[11] In another aspect, the present invention provides novel compounds of formula $V_A$ or a stereoisomer or pharmaceutically acceptable salt thereof:

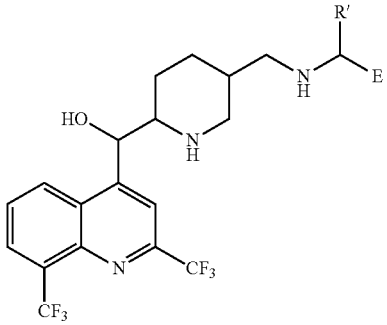

$V_A$ wherein:

A' is selected from H and CR'R"Z;

E is selected from —$C_{1-4}$ alkyl-NHA', —$C_{1-4}$ alkyl-CONHA', —$C_{0-4}$ alkyl-CONHOH, —$C_{0-4}$ alkyl-$CO_2R$, —$C_{0-4}$ alkyl-PO(OR)$_2$, —$C_{0-4}$ alkyl-$SO_2OR$, —$C_{0-4}$ alkyl-$SO_2NH_2$, and —$C_{0-4}$ alkyl-(NH)$NH_2$;

R at each occurrence is independently selected from H and $C_{1-4}$ alkyl;

R' is selected from H, $C_{1-4}$ alkyl, $C_{3-6}$-cycloalkyl, $C_{1-4}$ hydroxyalkyl, phenyl, benzyl, —$C_{0-4}$ alkyl-$CO_2R$, —$C_{0-4}$ alkyl-CONHR$^a$, —$C_{0-4}$ alkyl-CONHOH, and —$C_{0-4}$ alkyl-C(NH)$NH_2$;

R$^a$ is selected from H and —$C_{1-4}$ alkyl-CONHR$^b$;

R$^b$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$;

R" is selected from H and $C_{1-4}$ alkyl;

alternatively, R' and R" together form a $C_{3-6}$ cycloalkyl group;

Z is selected from H, $C_{1-4}$ alkyl, $C_{1-4}$ hydroxyalkyl, $C_{2-4}$ alkenyl, $C_{2-4}$ alkynyl, phenyl, phenyl-$C_{1-6}$ alkyl-, —$C_{0-4}$ alkyl-$CO_2R$, —$C_{0-4}$ alkyl-CONHR$^c$, —$C_{0-4}$ alkyl-C(NH)$NH_2$, —$C_{0-4}$ alkyl-CONHOH, CHOHCH$_2$$CO_2R$, CHOHCH$_2$CONHR$^c$, CHOHCH$_2$C(NH)$NH_2$, CH$_2$CHOHCO$_2$R, CH$_2$CHOHCONHR$^c$, CH$_2$CHOHC(NH)$NH_2$, CH=CHCO$_2$R, CH=CHCONHQ, CH=CHC(NH)$NH_2$, —$C_{1-4}$ alkyl-$SO_3R$, and —$C_{1-4}$ alkyl-$SO_2NHR^c$;

R$^c$ is selected from H, —$C_{1-4}$ alkyl-CONHR$^d$, CHOHCH$_2$CONHR$^d$, CH$_2$CHOHCONHR$^d$, and —$C_{1-4}$ alkyl-$SO_2NHR^d$;

R$^d$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$; and, each phenyl or benzyl group is independently optionally substituted with 1-2 groups selected from $CF_3$, halogen, $C_{1-4}$ alkyl, —CN, CONR$_2$, $NO_2$, $NR_2$, OR, $NHSO_2CH_3$, and SONHR.

[12] In another aspect, the present invention provides novel compounds of formula VI or a stereoisomer or pharmaceutically acceptable salt thereof:

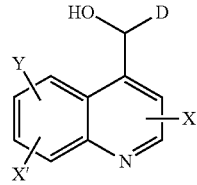

VI wherein:

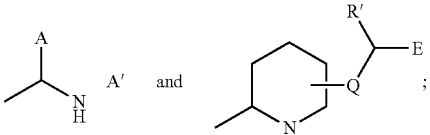

D is selected from

A is selected from H, $C_{1-4}$ alkyl, (CH2)$_n$CONHA', (CH$_2$)$_n$CONHOH, and (CH$_2$)$_n$$CO_2R$;

n is selected from 0, 1, 2, 3, and 4;

A' is selected from H and CR'R"Z;

Q is selected from O, NR, and CH$_2$NR;

R at each occurrence is independently selected from H and $C_{1-4}$ alkyl;

R' is selected from H, $C_{1-4}$ alkyl, $C_{3-6}$-cycloalkyl, $C_{1-4}$ hydroxyalkyl, phenyl, benzyl, —$C_{0-4}$ alkyl-$CO_2R$, —$C_{0-4}$ alkyl-CONHOH, —$C_{0-4}$ alkyl-CONHR$^a$, —$C_{0-4}$ alkyl-C(NH)$NH_2$;

R$^a$ is selected from H and —$C_{1-4}$ alkyl-CONHR$^b$;

R$^b$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$;

R" is selected from H, $C_{1-4}$ alkyl or together with R' forms a $C_3$-$C_6$ cycloalkyl group;

E is selected from —$C_{1-4}$ alkyl-NHA', —$C_{0-4}$ alkyl-CONHA', —$C_{0-4}$ alkyl-CONHOH, —$C_{0-4}$ alkyl-$CO_2R$, —$C_{0-4}$ alkyl-PO(OR)$_2$, —$C_{0-4}$ alkyl-$SO_2OR$, —$C_{0-4}$ alkyl-$SO_2NH_2$, and —$C_{0-4}$ alkyl-(NH)$NH_2$;

X is phenyl substituted with B;

X' is selected from H, halo, —CN, O—$C_{1-4}$ alkyl, and $CF_3$;

Y is selected from H, halo, —CN, O—$C_{1-4}$ alkyl, and $CF_3$;

B is selected from —$C_{1-4}$ alkyl-tetrazole, —$C_{0-4}$ alkyl-$CO_2R$, —$C_{0-4}$ alkyl-CONR$_2$, —$C_{1-4}$ alkyl-CN, O—$C_{1-4}$ alkyl-tetrazole, O—$C_{1-4}$ alkyl-$CO_2R$, O—$C_{1-4}$ alkyl-CON(R)$_2$, O—$C_{3-6}$ alkenyl-$CO_2R$, O—$C_{1-4}$ alkyl-PO(OR)$_2$, NR—$C_{3-4}$ alkenyl, NRSO$_2$CH$_3$, NR—$C_{1-4}$ alkyl-$CO_2R$, NR—$C_{1-4}$ alkyl-CON(R)$_2$, NR—$C_{3-4}$ alkenyl-$CO_2R$, NR—$C_{1-4}$ alkyl-PO(OR)$_2$, NR—$C_{1-4}$ alkyl-$SO_2OR$, NR—$C_{1-4}$ alkyl-tetrazole, SO$_2$NRCH$_3$, OCH$_2$CH(R)CONR$^c$H$_2$CO$_2$R, CH$_2$-aryl, O—$C_{1-4}$ alkyl-PO(OR)$_2$, O—$C_{1-4}$ alkyl-$SO_2OR$, OCH$_2$—$C_{0-4}$ alkyl-N$^+$(CH$_3$)$_3$A$^-$, O—$C_{0-4}$ alkyl-biphenyl, O—$C_{0-4}$ alkyl-biphenyl-$C_{1-4}$ alkyl-$CO_2R$, O—$C_{0-4}$ alkyl-biphenyl-$C_{1-4}$ alkyl-tetrazole, O—$C_{0-4}$ alkyl-biphenyl-$C_{1-4}$ alkyl-CN, O—$C_{0-4}$ alkyl-biphenyl-$C_{1-4}$ alkyl-CON(R)$_2$, NR—$C_{0-4}$ alkyl-biphenyl, NR—$C_{0-4}$ alkyl-biphenyl-$C_{1-4}$ alkyl-$CO_2R$, NR—$C_{0-4}$ alkyl-biphenyl-$C_{1-4}$ alkyl-tetrazole, NR—$C_{0-4}$ alkyl-biphenyl-$C_{1-4}$ alkyl-CN, NR—$C_{0-4}$ alkyl-biphenyl-$C_{1-4}$ alkyl-CON(R)$_2$, O—$C_{0-4}$ alkyl-aryl, O—$C_{0-4}$ alkyl-heteroaryl, NR—$C_{0-4}$ alkyl-aryl, NR—$C_{0-4}$ alkyl-heteroaryl, O—$C_{0-4}$ alkyl-aryl-$C_{1-4}$ alkyl-$CO_2R$, O—$C_{0-4}$ alkyl-aryl-$C_{2-6}$ alkenyl-$CO_2R$, O—$C_{0-4}$ alkyl-aryl-$C_{1-4}$ alkyl-tetrazole, O—$C_{0-4}$ alkyl-aryl-$C_{1-4}$ alkyl-CN, O—$C_{0-4}$ alkyl-aryl-$C_{1-4}$ alkyl-CON(R)$_2$, O—$C_{0-4}$ alkyl-aryl-$C_{1-4}$ alkyl-PO(OR)$_2$, O—$C_{0-4}$ alkyl-aryl-O—$C_{1-4}$ alkyl-$CO_2R$, O—$C_{0-4}$ alkyl-aryl-O—$C_{3-6}$ alkenyl-$CO_2R$, O—$C_{0-4}$ alkyl-aryllO—$C_{1-4}$ alkyl-tetrazole, O—$C_{0-4}$ alkyl-aryllO—$C_{1-4}$ alkyl-CN, O—$C_{0-4}$ alkyl-aryl-$C_{1-4}$ alkyl-CON(R)$_2$, O—$C_{0-4}$ alkyl-aryllO—$C_{1-4}$ alkyl-PO(OR)$_2$, O—$C_{0-4}$ alkyl-aryl-NR—$C_{1-4}$ alkyl-$CO_2R$, O—$C_{0-4}$ alkyl-aryl-NRC$_{3-6}$ alkenyl-$CO_2R$, O—$C_{0-4}$ alkyl-aryl-NR—$C_{1-4}$ alkyl-tetrazole, O—$C_{0-4}$ alkyl-aryl-NR—$C_{1-4}$ alkyl-CN, O—$C_{0-4}$ alkyl-aryl-NR—$C_{1-4}$ alkyl-CON(R)$_2$, O—$C_{0-4}$ alkyl-aryl-NR—$C_{1-4}$ alkyl-PO(OR)$_2$, NR—$C_{0-4}$ alkyl-aryl-$C_{1-4}$ alkyl-$CO_2R$, NR—$C_{0-4}$ alkyl-aryl-$C_{2-6}$ alkenyl-$CO_2R$, NR—$C_{0-4}$ alkyl-aryl-$C_{1-4}$ alkyl-tetrazole, NR—$C_{0-4}$ alkyl-aryl-$C_{1-4}$ alkyl-CN, NR—$C_{0-4}$ alkyl-aryl-$C_{1-4}$ alkyl-CON(R)$_2$, NR—$C_{0-4}$ alkyl-aryl-$C_{1-4}$ alkyl-PO(OR)$_2$, NR—$C_{0-4}$ alkyl-aryl-NR—$C_{1-4}$ alkyl-CO$_2$R, NR—$C_{0-4}$ alkyl-aryl-NR—$C_{3-6}$ alkenyl-CO$_2$R, NR—$C_{0-4}$ alkyl-aryl-NR—$C_{1-4}$ alkyl-tetrazole, NR—$C_{0-4}$ alkyl-aryl-NR—$C_{1-4}$ alkyl-CN, NR—$C_{0-4}$ alkyl-aryl-NR—$C_{1-4}$ alkyl-CON(R)$_2$, NR—$C_{0-4}$ alkyl-aryl-NR—$C_{1-4}$ alkyl-PO(OR)$_2$, NR—$C_{0-4}$ alkyl-arylIO—$C_{1-4}$ alkyl-CO$_2$R, NR—$C_{0-4}$ alkyl-aryl-O—$C_{3-6}$ alkenyl-CO$_2$R, NR—$C_{0-4}$ alkyl-aryl-O—$C_{1-4}$ alkyl-tetrazole, NR—$C_{0-4}$ alkyl-arylIO—$C_{1-4}$ alkyl-CN, NR—$C_{0-4}$ alkyl-aryl-O—$C_{1-4}$ alkyl-CON(R)$_2$, NR—$C_{0-4}$ alkyl-arylIO—$C_{1-4}$ alkyl-PO(OR)$_2$, O—$C_{0-4}$ alkyl-heteroaryl-$C_{1-4}$ alkyl-CO$_2$R, O—$C_{0-4}$ alkyl-heteroaryl-$C_{2-6}$ alkenyl-CO$_2$R, O—$C_{0-4}$ alkyl-heteroaryl-$C_{1-4}$ alkyl-tetrazole, O—$C_{0-4}$ alkyl-heteroaryl-$C_{1-4}$ alkyl-CN, O—$C_{0-4}$ alkyl-heteroaryl-$C_{1-4}$ alkyl-CON(R)$_2$, O—$C_{0-4}$ alkyl-heteroaryl-$C_{1-4}$ alkyl-PO(OR)$_2$, O—$C_{0-4}$ alkyl-heteroaryl-O—$C_{1-4}$ alkyl-CO$_2$R, O—$C_{0-4}$ alkyl-heteroaryl-O—$C_{3-6}$ alkenyl-CO$_2$R, O—$C_{0-4}$ alkyl-heteroarylIO—$C_{1-4}$ alkyl-tetrazole, O—$C_{0-4}$ alkyl-heteroarylIO—$C_{1-4}$ alkyl-CN, O—$C_{0-4}$ alkyl-heteroarylIO—$C_{1-4}$ alkyl-CON(R)$_2$, O—$C_{0-4}$ alkyl-heteroarylIO—$C_{1-4}$ alkyl-PO(OR)$_2$, O—$C_{0-4}$ alkyl-heteroaryl-NR—$C_{1-4}$ alkyl-CO$_2$R, O—$C_{0-4}$ alkyl-heteroaryl-NR—$C_{3-6}$ alkenyl-CO$_2$R, O—$C_{0-4}$ alkyl-heteroaryl-NR—$C_{1-4}$ alkyl-tetrazole, O—$C_{0-4}$ alkyl-heteroaryl-NR—$C_{1-4}$ alkyl-CN, O—$C_{0-4}$ alkyl-heteroaryl-NR—$C_{1-4}$ alkyl-CON(R)$_2$, O—$C_{0-4}$ alkyl-heteroaryl-NR—$C_{1-4}$ alkyl-PO(OR)$_2$, NR—$C_{0-4}$ alkyl-heteroaryl-$C_{1-4}$ alkyl-CO$_2$R, NR—$C_{0-4}$ alkyl-heteroaryl-$C_{2-6}$ alkenyl-CO$_2$R, NR—$C_{0-4}$ alkyl-heteroaryl-$C_{1-4}$ alkyl-tetrazole, NR—$C_{0-4}$ alkyl-heteroaryl-$C_{1-4}$ alkyl-CN, NR—$C_{0-4}$ alkyl-heteroaryl-$C_{1-4}$ alkyl-CON(R)$_2$, NR—$C_{0-4}$ alkyl-heteroaryl-$C_{1-4}$ alkyl-PO(OR)$_2$, NR—$C_{0-4}$ alkyl-heteroaryl-NR—$C_{1-4}$ alkyl-CO$_2$R, NR—$C_{0-4}$ alkyl-heteroaryl-NR—$C_{3-6}$ alkenyl-CO$_2$R, NR—$C_{0-4}$ alkyl-heteroaryl-NR—$C_{1-4}$ alkyl-tetrazole, NR—$C_{0-4}$ alkyl-heteroaryl-NR—$C_{1-4}$ alkyl-CN, NR—$C_{0-4}$ alkyl-heteroaryl-NR—$C_{1-4}$ alkyl-CON(R)$_2$, NR—$C_{0-4}$ alkyl-heteroaryl-NR—$C_{1-4}$ alkyl-PO(OR)$_2$, NR—$C_{0-4}$ alkyl-heteroaryl-O—$C_{1-4}$ alkyl-CO$_2$R, NR—$C_{0-4}$ alkyl-heteroaryl-O—$C_{3-6}$ alkenyl-CO$_2$R, NR—$C_{0-4}$ alkyl-heteroaryl-O—$C_{1-4}$ alkyl-tetrazole, NR—$C_{0-4}$ alkyl-heteroaryl-O—$C_{1-4}$ alkyl-CN, NR—$C_{0-4}$ alkyl-heteroaryl-O—$C_{1-4}$ alkyl-CON(R)$_2$, NR—$C_{0-4}$ alkyl-heteroarylIO—$C_{1-4}$ alkyl-PO(OR)$_2$, where heteroaryl is a 5-12 membered ring system consisting of carbon atoms and from $_{1-4}$ heteroatoms selected from N, O, and S, and wherein aryl and heteroaryl are substituted with 1-2 R and tetrazole is substituted with 0-1 R;

Z is selected from H, $C_{1-4}$ alkyl, $C_{1-4}$ hydroxyalkyl, $C_{2-4}$ alkenyl, $C_{2-4}$ alkynyl, phenyl, phenyl-$C_{1-6}$ alkyl-, —$C_{0-4}$ alkyl-CO$_2$R, —$C_{0-4}$ alkyl-CONHR$^c$, —$C_{0-4}$ alkyl-CONHOH, —$C_{0-4}$ alkyl-C(NH)NH$_2$, CHOHCH$_2$CO$_2$R, CHOHCH$_2$CONHR$^c$, CHOHCH$_2$C(NH)NHR$^c$, CH$_2$CHOHCO$_2$R, CH$_2$CHOHCONHR$^c$, CH$_2$CHOHC(NH)NH$_2$, CH=CHCO$_2$R, CH=CHCONHQ, CH=CHC(NH)NH$_2$, —$C_{1-4}$ alkyl-SO$_3$R, and —$C_{1-4}$ alkyl-SO$_2$NHR$^c$;

R$^c$ is selected from H, —$C_{1-4}$ alkyl-CONHR$^d$, CHOHCH$_2$CONHR$^d$, CH$_2$CHOHCONHR$^d$, and —$C_{1-4}$ alkyl-SO$_2$NHR$^d$;

R$^d$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-CONH$_2$; and, wherein each aryl, heteroaryl, phenyl, or benzyl group is independently optionally substituted with 1-2 groups selected from CF$_3$, halogen, $C_{1-4}$ alkyl, —CN, CONR$_2$, NO$_2$, NR$_2$, OR, NHSO$_2$CH$_3$, and SO$_2$NHR.

In another aspect, the present invention provides novel compounds of formula VI$_A$ or a stereoisomer or pharmaceutically acceptable salt thereof:

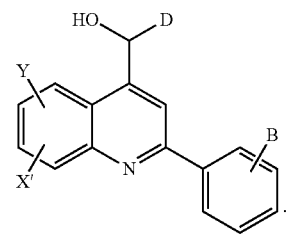

In another aspect, n is 0. In another aspect, n is 1. In another aspect, n is 2. In another aspect, n is 3. In another aspect, n is 4.

In another aspect, A' is H. In another aspect, A' is CR'R"Z;

In another aspect, R' and R" together form a $C_{3-6}$ cycloalkyl group;

In another aspect, R' is selected from $C_{3-6}$ cycloalkyl, $C_{1-4}$ hydroxyalkyl, phenyl, benzyl, —$C_{0-4}$ alkyl-CO$_2$R, —$C_{0-4}$ alkyl-CONHR$^a$, —$C_{0-4}$ alkyl-CONHOH, and —$C_{0-4}$ alkyl-C(NH)NH$_2$;

In another aspect, R$^a$ is H. In another aspect, R$^a$ is —$C_{1-4}$ alkyl-CONHR$^b$.

In another aspect, Z is selected from —$C_{0-4}$ alkyl-CO$_2$R, —$C_{0-4}$ alkyl-CONHR$^c$, —$C_{0-4}$ alkyl-CONHOH, —$C_{0-4}$ alkyl-C(NH)NH$_2$, CHOHCH$_2$CO$_2$R, CHOHCH$_2$CONHR$^c$, CHOHCH$_2$C(NH)NH$_2$, CH$_2$CHOHCO$_2$R, CH$_2$CHOHCONHR$^c$, CH$_2$CHOHC(NH)NH$_2$, CH=CHCO$_2$R, CH=CHCONHQ, CH=CHC(NH)NH$_2$, —$C_{1-4}$ alkyl-SO$_3$R, and —$C_{1-4}$ alkyl-SO$_2$NHR$^c$;

In another aspect, R$^c$ is selected from —$C_{1-4}$ alkyl-CONHR$^d$, CHOHCH$_2$CONHR$^d$, CH$_2$CHOHCONHR$^d$, and —$C_{1-4}$ alkyl-SO$_2$NHR$^d$;

In another aspect, the present invention provides novel pharmaceutical compositions, comprising: a pharmaceutically acceptable carrier and a therapeutically effective amount of a compound of the present invention or a pharmaceutically acceptable salt form thereof.

In another aspect, the present invention provides a novel method for treating for the treatment of malaria, tuberculosis, or other infectious diseases, and a combination thereof. In an example, the disease is mediated by pathogens/parasites residing in tissue such as blood and liver.

In another aspect, the present invention provides a novel method of attenuating the activity of parasites/pathogens in a patient, comprising: administering a compound or composition of the present invention.

In another aspect, the present invention provides a novel method of treating an infectious disease, (e.g., malaria, tuberculosis,) characterized by an inappropriate occupation of the parasite or pathogen, comprising: administering to a patient in need thereof a compound or composition of the present invention.

In another aspect, the present invention provides a novel method for treating an infectious disease, comprising: administering to a patient in need thereof a therapeutically effective amount of a compound of the present invention or a pharmaceutically acceptable salt form thereof, wherein the infectious disease is selected from malaria, tuberculosis, or other infectious diseases, and a combination thereof.

In another aspect, the malaria is selected from the group: *Plasmodium falciparum*, *Plasmodium malariae*, *Plasmodium ovale*, *Plasmodium Vivax*, and *Plasmodium knowlesi*.

In another aspect, the *mycobacterium tuberculosis* may be pulmonary or extrapulmonary.

In another aspect, the present invention provides a compound of the present invention for use in therapy.

In another aspect, the present invention provides the use of the present invention for the manufacture of a medicament for the treatment of malaria, tuberculosis, or other infectious diseases, and a combination thereof.

The present invention may be embodied in other specific forms without departing from the spirit or essential attributes thereof. This invention encompasses all combinations of aspects of the invention noted herein. It is understood that any and all aspects of the present invention may be taken in conjunction with any other aspect or aspects to describe additional aspects. It is also to be understood that each individual element of the aspects is intended to be taken individually as its own independent aspect. Furthermore, any element of an aspect is meant to be combined with any and all other elements from any aspect to describe an additional aspect.

DEFINITIONS

The examples provided in the definitions present in this application are non-inclusive unless otherwise stated. They include but are not limited to the recited examples.

An infectious disease is a clinically evident disease resulting from the presence of pathogenic microbial agents, including pathogenic viruses, pathogenic bacteria, fungi, protozoa, multicellular parasites, and aberrant proteins known as prions.

The compounds herein described may have asymmetric centers, geometric centers (e.g., double bond), or both. All chiral, diastereomeric, racemic forms and all geometric isomeric forms of a structure are intended, unless the specific stereochemistry or isomeric form is specifically indicated. Compounds of the present invention containing an asymmetrically substituted atom may be isolated in optically active or racemic forms. It is well known in the art how to prepare optically active forms, such as by resolution of racemic forms, by synthesis from optically active starting materials, or through use of chiral auxiliaries. Geometric isomers of olefins, C=N double bonds, or other types of double bonds may be present in the compounds described herein, and all such stable isomers are included in the present invention. Specifically, cis and trans geometric isomers of the compounds of the present invention may also exist and may be isolated as a mixture of isomers or as separated isomeric forms. All processes used to prepare compounds of the present invention and intermediates made therein are considered to be part of the present invention. All tautomers of shown or described compounds are also considered to be part of the present invention.

"Alkyl" and "alkylene" includes both branched and straight-chain saturated aliphatic hydrocarbon groups having the specified number of carbon atoms. For example, $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, and s-pentyl.

"Alkenyl" includes the specified number of hydrocarbon atoms in either straight or branched configuration with one or more unsaturated carbon-carbon bonds that may occur in any stable point along the chain, such as ethenyl and propenyl. For example, $C_{2-6}$ alkenyl includes $C_2$, $C_3$, $C_4$, $C_5$, and $C_6$ alkenyl groups.

"Alkynyl" includes the specified number of hydrocarbon atoms in either straight or branched configuration with one or more triple carbon-carbon bonds that may occur in any stable point along the chain, such as ethynyl and propynyl. For example, $C_{2-6}$ Alkynyl includes $C_2$, $C_3$, $C_4$, $C_5$, and $C_6$ alkynyl groups.

"Cycloalkyl" includes the specified number of hydrocarbon atoms in a saturated ring, such as cyclopropyl, cyclobutyl, cyclopentyl, cyclohexyl, cycloheptyl, and cyclooctyl. For example, $C_{3-8}$ cycloalkyl includes $C_3$, $C_4$, $C_5$, $C_6$, $C_7$, and $C_8$ cycloalkyl groups. Cycloalkyl also includes bicycloalkyl and tricycloalkyl, both of which include fused and bridged rings (e.g., norbornane and adamantane).

"Carbocycle" includes the specified number of carbon atoms in a cycloalkyl ring or a partially unsaturated cycloalkyl ring (e.g., cyclohexene and cyclopentadiene).

"Cyclic amine" is a hydrocarbon ring wherein one carbon atom of the ring has been replaced by a nitrogen atom. The cyclic amine can be unsaturated, partially saturated, or fully saturated. The cyclic amine can also be bicyclic, tricyclic, and polycyclic. Examples of cyclic amine include pyrrolidine and piperidine.

"Halo" or "halogen" refers to F, Cl, bromo, and iodo.

"Acyl" refers to an alkyl group terminated by a carbonyl (C=O) group. The acyl moiety is attached via the carbonyl group.

"Counterion" is used to represent a small, negatively charged species, such as chloride, bromide, hydroxide, acetate, and sulfate.

The group "$C_6H_4$" represents a phenylene.

"Lactone" refers to a ring containing a carboxyl group ($CO_2$).

"Lactam" refers to a ring containing an amido group (C(O)N).

"Aryl" refers to any stable 6, 7, 8, 9, 10, 11, 12, or 13 membered monocyclic, bicyclic, or tricyclic ring, wherein at least one ring, if more than one is present, is aromatic. Examples of aryl include fluorenyl, phenyl, naphthyl, indanyl, and tetrahydronaphthyl.

"Heteroaryl" refers to any stable 5, 6, 7, 8, 9, 10, 11, or 12 membered monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable.

Examples of heteroaryl includes acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, pyranyl, pyrazinyl, pyrazolyl, pyridazinyl, pyridooxazole, pyridoimidazole, pyridothiazole, pyridinyl, pyridyl, pyrimidinyl, 2H-pyrrolyl, pyrrolyl, quinazolinyl, quinolinyl, 4H-quinolizinyl, quinoxalinyl, quinuclidinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"Heterocycle" refers to any stable 4, 5, 6, 7, 8, 9, 10, 11, or 12 membered, (unless the number of members is otherwise recited), monocyclic, bicyclic, or tricyclic heterocyclic ring that is saturated or partially unsaturated, and which consists of carbon atoms and 1, 2, 3, or 4 heteroatoms independently selected from the group consisting of N, O, and S. If the heterocycle is defined by the number of carbons atoms, then from 1, 2, 3, or 4 of the listed carbon atoms are replaced by a heteroatom. If the heterocycle is bicyclic or tricyclic, then at least one of the two or three rings must contain a heteroatom, though both or all three may each contain one or more heteroatoms. The N group may be N, NH, or N-substituent, depending on the chosen ring and if substituents are recited. The nitrogen and sulfur heteroatoms optionally may be oxidized (e.g., S, S(O), S(O)$_2$, and N—O). The heterocycle may be attached to its pendant group at any heteroatom or carbon atom that results in a stable structure. The heterocycles described herein may be substituted on carbon or on a nitrogen atom if the resulting compound is stable.

Examples of heterocycles include, but are not limited to, decahydroquinolinyl, imidazolidinyl, imidazolinyl, indolinyl, isatinoyl, methylenedioxyphenyl, morpholinyl, octahydroisoquinolinyl, oxazolidinyl, oxindolyl, piperazinyl, piperidinyl, piperidonyl, 4-piperidonyl, piperonyl, pyranyl, pyrazolidinyl, pyrazolinyl, pyrrolidinyl, pyrrolinyl, tetrahydrofuranyl, tetrahydroisoquinolinyl, tetrahydroquinolinyl, 1-aza-bicyclo[2.2.2]octane, 2,5-diaza-bicyclo[2.2.2]octane, and 2,5-diaza-bicyclo[2.2.1]heptane. Also included are fused ring and spiro compounds containing, for example, the above heterocycles.

"Mammal" covers warm blooded mammals that are typically under medical care (e.g., humans and domesticated animals). Examples of mammals include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are useful. Lists of suitable salts are found in *Remington's Pharmaceutical Sciences,* 18th ed., Mack Publishing Company, Easton, Pa., 1990, p 1445.

Drugs enter the CNS from the systemic circulation by crossing the blood-brain barrier (BBB). The BBB is a highly specialized 'gate-keeper' that protects the brain by preventing the entry of many potentially harmful substances into the CNS from the systemic circulation. Much is known about the BBB, and of the physical-chemical properties required for compounds transported across it.

Drugs that do not cross the BBB into the CNS or that are readily eliminated through transport mechanisms [J Clin Invest. 97, 2517 (1996)] are known in the literature and have low CNS activity due to their inability to develop brain levels necessary for pharmacological action. The BBB has at least one mechanism to remove drugs prior to their accumulation in the CNS. P-Glycoproteins (P-gp) localized in plasma membrane of the BBB can influence the brain penetration and pharmacological activity of many drugs through translocation across membranes. The lack of accumulation into the brain by some drugs can be explained by their active removal from the brain by P-gp residing in the BBB. For example, the typical opioid drug loperamide, clinically used as an antidiarrheal, is actively removed from the brain by P-gp, thus explaining its lack of opiate-like CNS effects. Another example is domperidone, a dopamine receptor blocker that participates in the P-gp transport [J Clin Invest. 97, 2517 (1996)]. Whereas dopamine receptor blockers that cross the BBB can be used to treat schizophrenia, the readily-eliminated domperidone can be used to prevent emesis, without the likelihood of producing adverse CNS effects.

In addition to the above compounds, agents possessing structural characteristics that retard or prevent BBB penetration or contribute to participation in active elimination processes have been identified in various classes of therapeutics. These include antihistamines [Drug Metab. Dispos. 31, 312 (2003)], beta-adrenergic receptor antagonists (B-blockers) [Eur. J. Clin. Pharmacol. 28, Suppl: 21-3 (1985); Br. J. Clin. Pharmacol, 11 (6), 549-553 (1980], non-nucleoside reverse transcriptase inhibitors (NNRTIs) [J. Pharm Sci., 88(10) 950-954 (1999)], and opioid antagonists. This latter group has been tested in relation to their activity in the GI tract. These peripherally selective opioid antagonists are described in various US patents as being useful in the treatment of non-CNS pathologies in mammals, in particular those of the GI tract [see U.S. Pat. No. 5,260,542; U.S. Pat. No. 5,434,171; U.S. Pat. No. 5,159,081; and U.S. Pat. No. 5,270,238].

Other types of non-brain penetrant compounds can be prepared through the creation of a charge within the molecule. Thus, the addition of a methyl group to the tertiary amine functionality of the drugs scopolamine or atropine, unlike the parent molecules, prevents their passage across the BBB through the presence of a positive charge. However, the new molecules (methyl-scopolamine and methyl-atropine) retain their full anticholinergic pharmacological properties. As such, these drugs can also be used to treat peripheral diseases, without the concern of adverse CNS effects. The quaternary ammonium compound methylnaltrexone is also used for the prevention and/or treatment of opioid and non-opioid induced side effects associated with opioid administration. A recent discussion of chemical modifications that can affect brain exposure can be found in J. Med. Chem. 49, 7559, 2006.

It would be beneficial for the compounds of the present invention to be peripherally restricted, i.e., have an inability or limited ability to cross the BBB, or be readily eliminated from the brain through active transport systems. It may be desirable for the compounds of the present invention to be peripherally restricted, which in turn will result in no or very limited CNS effects. Compounds that provide peripherally mediated anti-malarial, anti-tuberculosis or anti-bacterial properties should result in therapeutic agents with greater safety. It can be desirable that the compounds of the present invention, when administered in a therapeutically effective amount, have no or very limited CNS effects. It can also be desirable that the lack of CNS effects is a result of the compounds of the present invention having minimal brain concentrations when administered in therapeutically effective amounts. In this context, minimal brain concentrations means levels that are too low to be therapeutically effective for the treatment of a CNS indication or too low to cause significant or measurable deleterious or undesired side effects.

Melfoquine, (Compound AA, where X=2-$CF_3$, X'=8-$CF_3$, Y=H, D=2-piperidinyl) is a drug that crosses the BBB and is indicated for the treatment of malaria. In compound AA, at least one of A, A', D, R, R', E, and Z is suitably modified or replaced by a group capable of reducing or limiting the CNS (brain) levels of compound AA. This reduced or limited CNS activity occurs via at least one of A A, A' B, E, R', Z and Z' being a group that either limits compound AA's ability to cross the BBB relative to that of mefloquine or enables it to be actively removed from the brain at a rate greater than that of mefloquine. Examples of the amount of compound AA present in the brain can include (a) from 50, 55, 60, 65, 70, 75, 80, 85, 90, 91, 92, 93, 94, 95, 96, 97, 98, 99, to 100% lower than otenabant, (b) from 90, 91, 92, 93, 94, 95, 96, 97, 98, 99, to 100% lower than otenabant, and (c) from 98, 99, to 100% lower than mefloquine, when administered at the same dosage.

The compounds of the present invention are expected to be anti-malarial, anti-tuberculosis, anti-bacterial, or other anti-infective agents. The compounds of the present invention are expected to inhibit parasitic growth of *P. falciparum* as well as other *Plasmodium* species including *P. berghei, P. chabaudi, P. yoelii* and *P. vinckei* both in vitro and in vivo under the experimental conditions described by Fidock et al., Nature Reviews Drug Discovery, 2004, 3, 509-520.

Inhibition of parasitic growth in vitro can be determined by assessing the reduction of [$^3$H]-hypoxanthine uptake in human erythrocytes infected with *Plasmodium*. Briefly, Compounds are diluted in low hypoxanthine medium and incubated for 24-48 hrs with infected erythrocytes (0.5-4% parasitemia). [$^3$H]-hypoxanthine is added and incubated a further 24 hrs. Cells are then harvested on to glass fiber filters and the amount of [$^3$H]-hypoxanthine uptake into erythrocytes is determined by liquid scintillation counting. Effectiveness of compounds is determined by comparing the level of [$^3$H]-hypoxanthine in the presence of compound in relation to positive and negative controls from which % inhibition and $IC_{50}$s can be calculated (Fidock et al., Nature Reviews Drug Discovery, 2004, 3, 509-520). Other methods, including microscopic detection of Giemsa-stained slides, measurement of lactate dehydrogenase production and flow cytometry, can also be employed to evaluate the inhibition of parasitic growth in vitro (Noedl et al., Trends in Parasitology, 2003, 19, 175-181.

Efficacy of antimalarial compounds in vivo can be determined using the *P. berghei* rodent malaria 4 day suppressive test. Briefly, mice are infected with *P. berghei* and dosed with compound at 4, 24, 48 and 72 hrs post-infection. At 96 hrs post-infection, blood smears are prepared and stained with Giemsa. Parasitemia is determined either microscopically or by FACS. The difference between control and experimental groups is calculated and expressed as % reduction in parasitemia calculated (Fidock et al., Nature Reviews Drug Discovery, 2004, 3, 509-520).

The compounds of the present invention are expected to be anti-malarials, anti-tuberculosis agents or anti-infectives.

Formulations and Dosages

In the present invention, the compound(s) of the present invention can be administered in any convenient manner (e.g., enterally or parenterally). Examples of methods of administration include orally and transdermally. One skilled in this art is aware that the routes of administering the compounds of the present invention may vary significantly. In addition to other oral administrations, sustained release compositions may be favored. Other acceptable routes may include injections (e.g., intravenous, intramuscular, subcutaneous, and intraperitoneal); subdermal implants; and, buccal, sublingual, topical, rectal, vaginal, and intranasal administrations. Bioerodible, non-bioerodible, biodegradable, and non-biodegradable systems of administration may also be used. Examples of oral formulations include tablets, coated tablets, hard and soft gelatin capsules, solutions, emulsions, and suspensions.

If a solid composition in the form of tablets is prepared, the main active ingredient can be mixed with a pharmaceutical vehicle, examples of which include silica, starch, lactose, magnesium stearate, and talc. The tablets can be coated with sucrose or another appropriate substance or they can be treated so as to have a sustained or delayed activity and so as to release a predetermined amount of active ingredient continuously. Gelatin capsules can be obtained by mixing the active ingredient with a diluent and incorporating the resulting mixture into soft or hard gelatin capsules. A syrup or elixir can contain the active ingredient in conjunction with a sweetener, which is typically calorie-free, an antiseptic (e.g., methylparaben and/or propylparaben), a flavoring, and an appropriate color. Water-dispersible powders or granules can contain the active ingredient mixed with dispersants or wetting agents or with suspending agents such as polyvinylpyrrolidone, as well as with sweeteners or taste correctors. Rectal administration can be effected using suppositories, which are prepared with binders melting at the rectal temperature (e.g., cocoa butter and/or polyethylene glycols). Parenteral administration can be effected using aqueous suspensions, isotonic saline solutions, or injectable sterile solutions, which contain pharmacologically compatible dispersants and/or wetting agents (e.g., propylene glycol and/or polyethylene glycol). The active ingredient can also be formulated as microcapsules or microspheres, optionally with one or more carriers or additives. The active ingredient can also be presented in the form of a complex with a cyclodextrin, for example α-, β-, or γ-cyclodextrin, 2-hydroxypropyl-β-cyclodextrin, and/or methyl-β-cyclodextrin.

The dose of the compound of the present invention administered daily will vary on an individual basis and to some extent may be determined by the severity of the disease being treated (e.g., malaria or another infectious disease). The dose of the compound of the present invention will also vary depending on the compound administered. Examples of dosages of compounds of the present invention include from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 15, 20, 25, 30, 35, 40, 45, 50, 55, 60, 65, 70, 76, 80, 85, 90, 95, to 100 mg/kg of mammal body weight. The compound can be administered in a single dose or in a number of smaller doses over a period of time. The length of time during which the compound is administered varies on an individual basis, and can continue until the desired results are achieved (e.g., prevention or reduced symptomology of malaria or another infectious disease). Therapy could, therefore, last from 1 day to weeks, months, or even years depending upon the subject being treated, the desired results, and how quickly the subject responds to treatment in accordance with the present invention.

A possible example of a tablet of the present invention is as follows.

| Ingredient | mg/Tablet |
|---|---|
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

A possible example of a capsule of the present invention is as follows.

| Ingredient | mg/Tablet |
|---|---|
| Active ingredient | 50 |
| Crystalline lactose | 60 |
| Microcrystalline cellulose | 34 |
| Talc | 5 |
| Magnesium stearate | 1 |
| Capsule fill weight | 150 |

In the above capsule, the active ingredient has a suitable particle size. The crystalline lactose and the microcrystalline cellulose are homogeneously mixed with one another, sieved, and thereafter the talc and magnesium stearate are admixed. The final mixture is filled into hard gelatin capsules of suitable size.

A possible example of an injection solution of the present invention is as follows.

| Ingredient | mg/Tablet |
|---|---|
| Active substance | 1.0 mg |
| 1N HCl | 20.0 µl |
| acetic acid | 0.5 mg |
| NaCl | 8.0 mg |
| Phenol | 10.0 mg |
| 1N NaOH | q.s. ad pH 5 |
| $H_2O$ | q.s. ad 1 mL |

Synthesis

The compounds of the present invention can be prepared in a number of ways known to one skilled in the art of organic synthesis (e.g., *J Med Chem* 1968, 11, 267; *J Med Chem* 1968, 11, 273; *J Med Chem* 1971, 14, 926; Tet 1991, 47 7609; U.S. Pat. Nos. 6,500,955; and, 4,327,215). The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. In particular, suitable protecting groups for and amino groups (NH-PG) include acetyl, trifluoroacetyl, t-butoxycarbonyl (BOC), benzyloxycarbonyl (CBz), and 9-fluorenymethyleneoxycarbonyl (Fmoc). An authoritative account describing the many alternatives to the trained practitioner is Greene and Wuts (*Protective Groups In Organic Synthesis*, Wiley and Sons, 1991).

Scheme 1 shows the synthesis of modified mefloquinone analogs following a general route that utilizes well-established chemistry. Condensation of 2-trifluoromethylaniline with ethyl 4,4,4-trifluoracetoacetate in the presence of PPA according to previously published procedures (J Med Chem, 1971, 14, 926) should provide the quinolone (step a) that is readily converted to the bromide using $POBr_3$ (step b). Conversion of the bromide to the formyl compound (step c) may be achieved using n-butyl lithium in ether at –78 degrees C. followed by addition of DMF (ChemMedChem, 2006, 1 593). The reaction of this aldehyde with the Schiff's base of an amino ester, such as that of the glycine adduct formed with benzyl amine, in the presence of a base such as lithium diisopropyl amide may afford the beta-hydroxy-alpha-amino ester (step d). Catalytic reduction of this ester in a hydrogen atmosphere can yield the benzyl amine (step e). Hydrolysis of the ester with lithium hydroxide in aqueous THF solution should afford the acid and activation of the acid with isobutyl chloroformate in the presence of triethylamine followed by treatment with ammonia can yield the carboxamide (step f). Alternatively, the activated carboxylic acid may be treated with amino acid ester to give the ester adduct (step g). This ester may be converted to the carboxamide by treatment with anhydrous ammonia in methanol, or by the procedure previously described (step h).

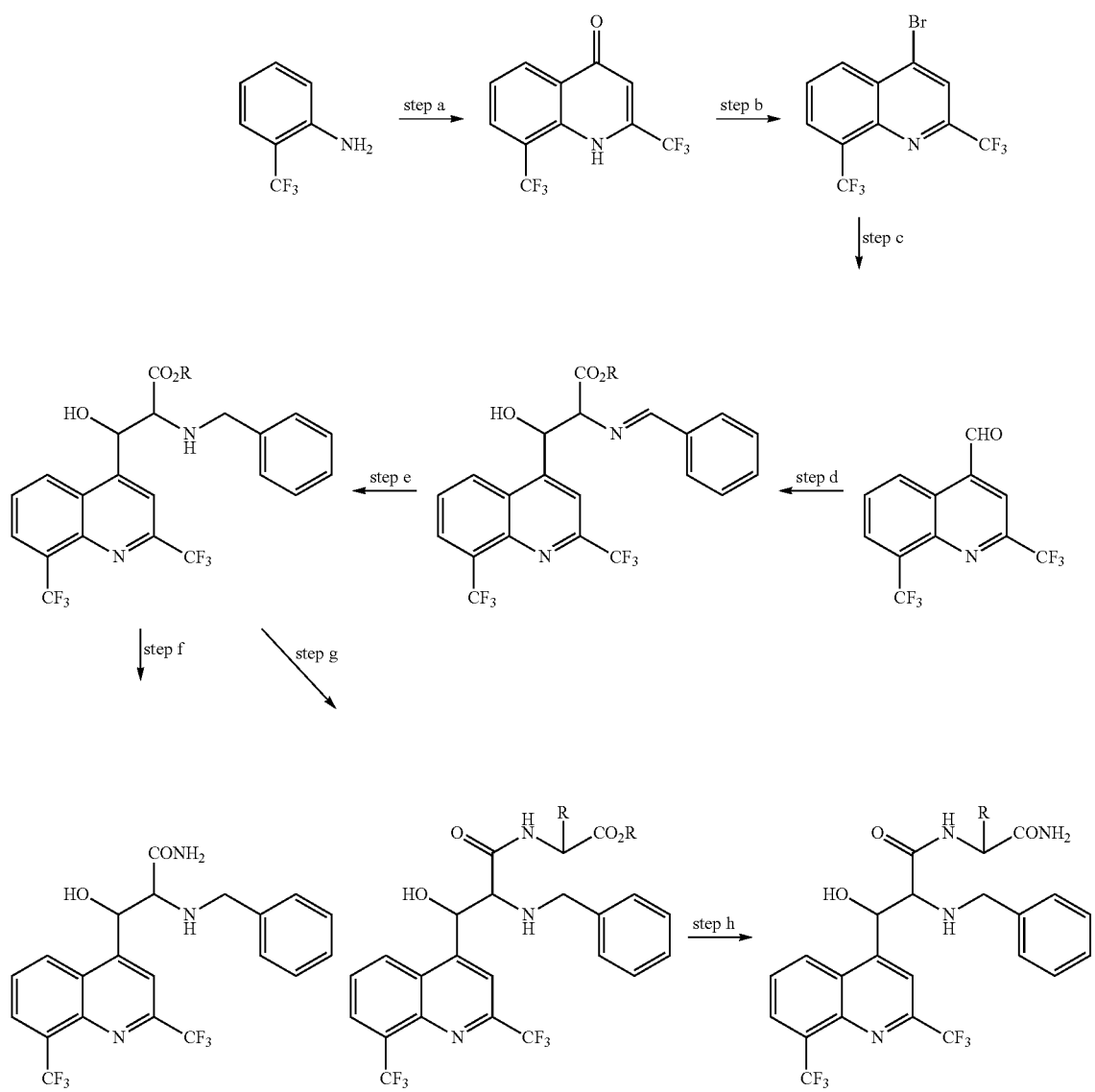

Scheme 1

Scheme 2 gives a synthesis of related mefloquine with variations on N-atoms of the quinloine pendant. The previously described aldehyde may be treated with ethyl nitroacetate in the presence of a base such as benzyltimethylammonium hydroxide in dioxane or anhydrous t-butanol under an atmosphere of nitrogen at about 40 degrees C. to produce the beta-hydroxy-alpha-nitroester (step a). Reduction of the nitro ester may be accomplished using zinc or iron in hydrochloric acid solution, or catalytic hydrogenation using platinum(IV) oxide ($PtO_2$) or Raney nickel (step b). Conversion of the ester to the carboxamide may be accomplished using anhydrous ammonia, or by hydrolysis of the ester with lithium hydroxide in aqueous THF solution to afford the acid and activation of the acid with isobutyl chloroformate in the presence of triethylamine followed by treatment with ammonia (step c). Alternatively, reductive amination of the amino group of the ester with acetaldehyde in the presence of sodium cyanoborohydride and acetic acid in methanol may afford the ethyamine (step d). This ethyamino ester can then be converted to carboxamide as described above (step e), or if treated with a primary amine such as 2-amino-1-propanol, may afford the n-substituted carboxamide (step f). Alternatively, this ester may be hydrolyzed with lithium hydroxide in aqueous THF solution to afford the acid, and activation of the acid with isobutyl chloroformate in the presence of triethylamine followed by treatment with an amino ester can produce the amino ester adduct (step g). Conversion of this ester to the carboxamide may be accomplished as previously described (step h).

Scheme 2

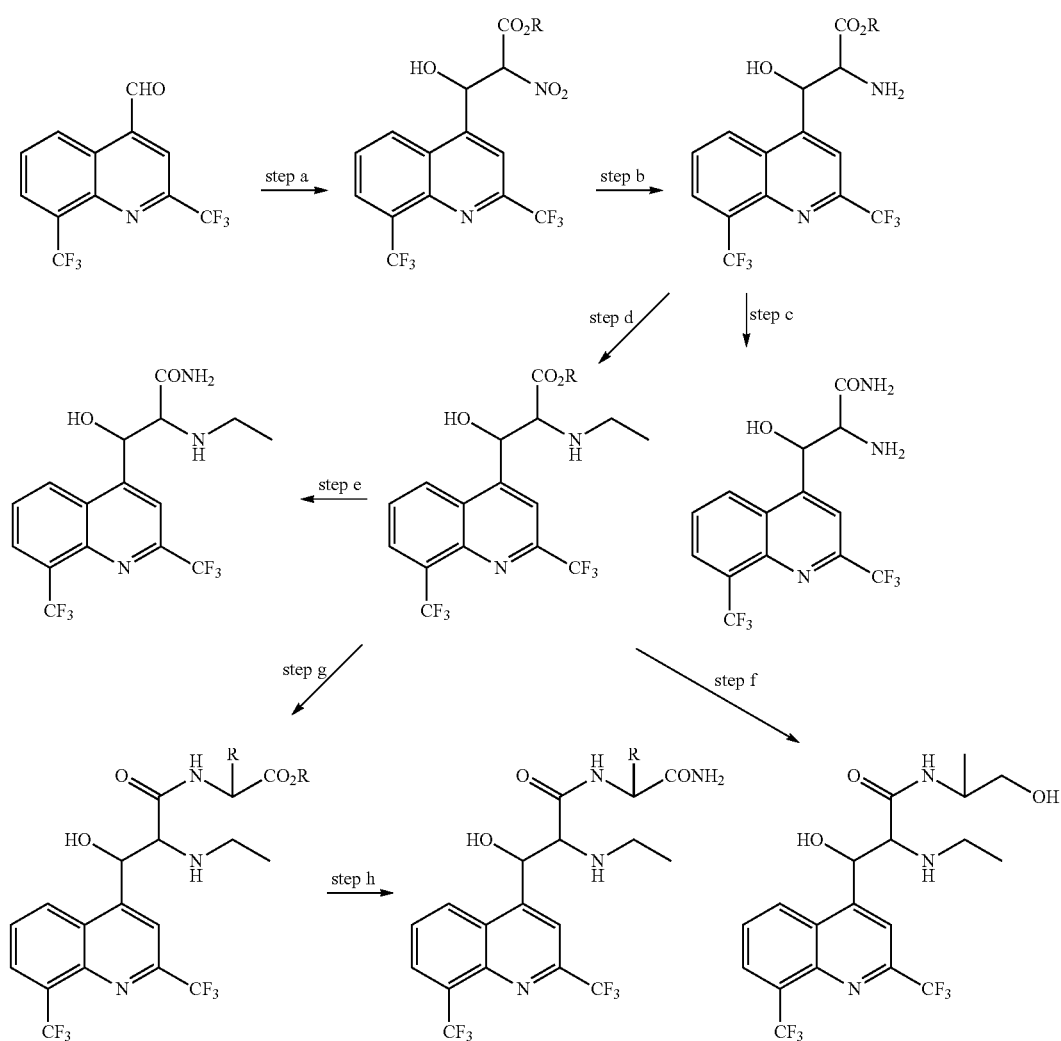

Scheme 3 shows further variations to the quinoline side-chain. N-t-BOC methyl sarcosine may be treated with sodium methoxide and ethyl formate in THF at about zero degrees to ambient temperature to afford the alpha-formyl adduct in its enolate form (U.S. Pat. No. 2,541,924) which upon further treatment with t-butyldimethylsilyl chloride in the presence of imidazole can yield the silylated-hydroxy-methylene adduct of the protected sarcosine ester. This intermediate may be treated with lithium salt of the previously described quinoline bromide in the presence of copper salts to produce after acidic hydrolysis, the hydroxy ester (step a). Conversion of the ester to the carboxamide may be accomplished as previously described (step b), and removal of the protecting group using TFA in methylene chloride solution may afford the N-methyamino-hydroxy-carboxamide (step c). Alternatively, the protected-amino hydroxy ester may be reacted with an amino acid ester under the standard peptide coupling conditions to produce the ester adduct (step d). Further conversion of the ester to the acid, and removal of the protecting group can yield the carboxamide (step e).

Scheme 3

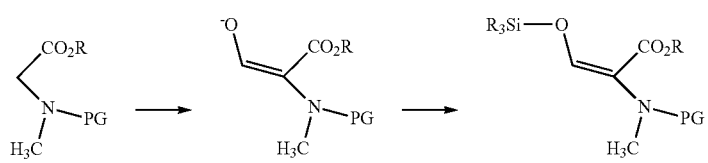

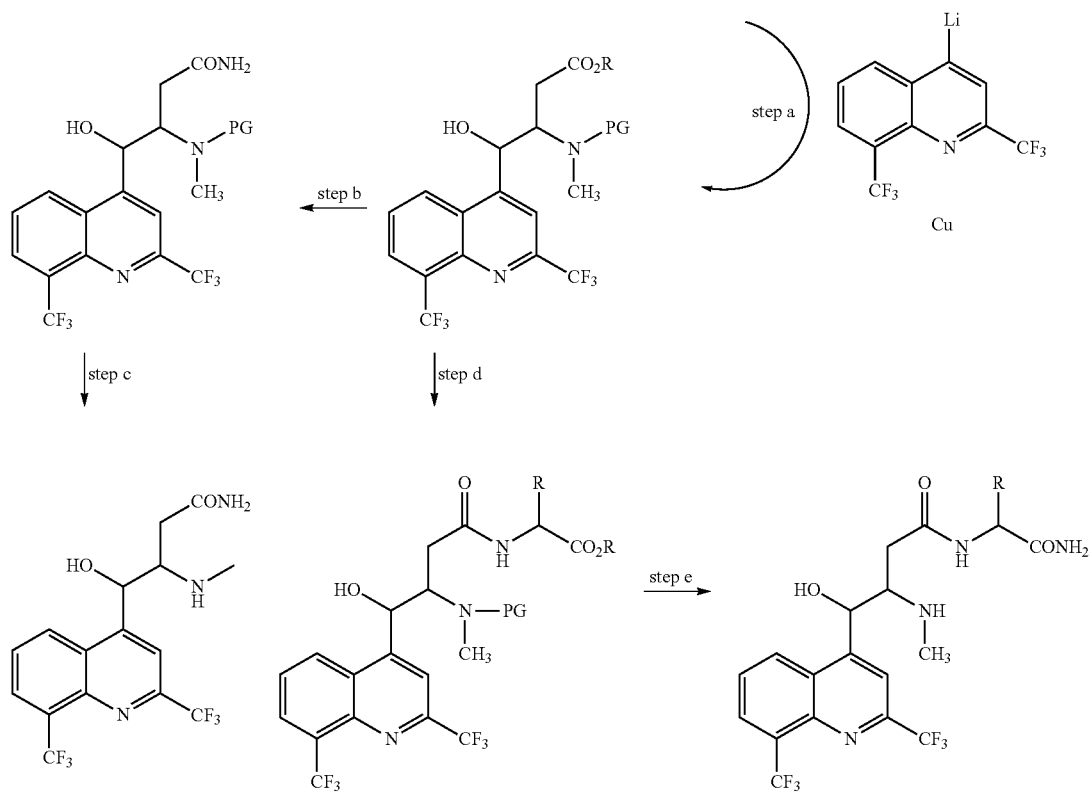

Scheme 4 shows a method of preparing seco-piperidine compounds with hydrophilic functional groups on the alkyl chains. The lithium salt of the bis-trifluoromethylnaphthaline, prepared from the bromide as previously described, may be treated with gaseous carbon dioxide to produce the carboxylic acid [J Med Chem, 14, 926 (1971)]. Conversion of the carboxylic acid to the Weinreb amide may be accomplished using DCCD (J Org Chem, 2001, 66, 2534) or triphosgene [Letters in Organic Chemistry, 2007, 4, 20) and methoxyamine hydrochloride (step b). The amide can then be converted to the methyl ketone using methyl Grignard reagent (Tetrahedron Lett, 1981, 22, 3815) (step c). The methyl ketone may be treated with seleneium dioxide in aqueous dioxane at about reflux to produce the quinolylglyoxal derivative (step d). Reductive amination of the glyoxal with amino acid esters using sodium cyanoborohydride in the presence of acetic acid can produce the amino ester (step e). Conversion of the ester to the carboxamide may be carried out as previously described and subsequent reduction of the ketone with sodium borohydride should give the beta-hydroxyethylamino carboxamide (step f).

Scheme 4

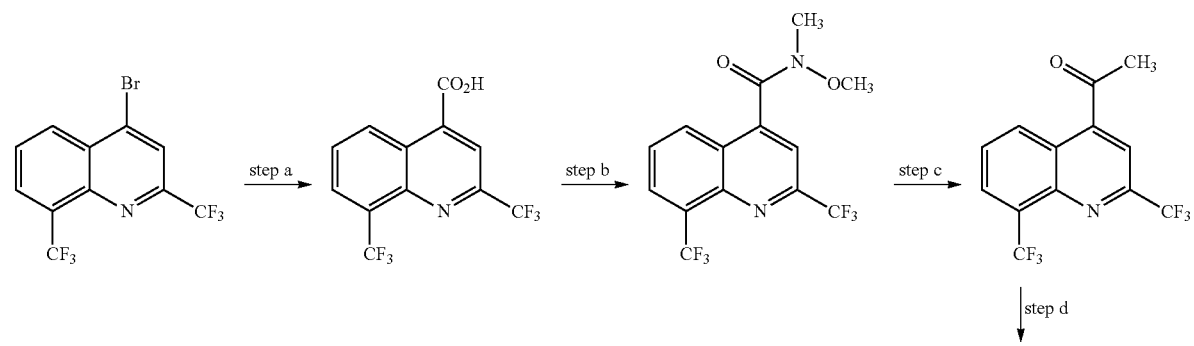

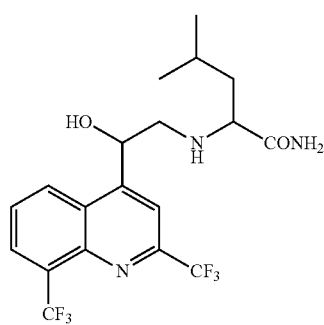
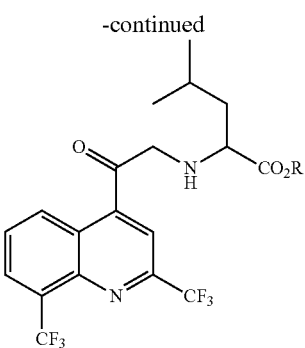
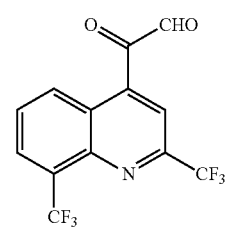

Scheme 5 shows the synthesis of mefloquine analogs with functionalized pendants on the piperidine ring. The Grignard of the previously describe bromoquinoline may be treated with the diethylketal protected O-acetaldehyde adduct of 3-hydroxy-2-pyridinecarboxaldehyde, which may be produced by treatment of the hydroxypyridine carboxaldehyde with bromoacetaldehyde diethyl acetal in acetonile in the presence of potassium carbonate at elevated temperature, to afford the hydroxymethylpyridine derivative (step a). Hydrolysis of the ketal under acidic conditions can produce the aldehyde (step b), and reductive amination of the aldehyde with an amino acid ester such as glycine methyl ester using sodium cyanoborohydride in the presence of acetic acid should yield the amino ester ether (step c). Direct conversion of the ester to the carboxamide may be accomplished using anhydrous ammonia in alcohol, or by hydrolysis of the ester to the carboxylic acid using lithium hydroxide in aqueous THF and coupling of the acid with ammonia or amine as described previously (step d). Alternatively, the quinolinyl Grignard may be reacted with a protected 3-hydroxy-2-pyridine carboxaldehyde, such as that protected with a trimethysilyl group, to provide the hydroxymethylpyridinol adduct (step e). Removal of the protecting may be accomplished using aqueous acid conditions (step f), and subsequent alkylation of the hydroxypyridine with ethyl bromoacetate in acetonitrile in the presence of potassium carbonate at elevated temperature should afford the ester derivative (step g). Conversion of the ester to the carboxamides may be accomplished as previously described (step h).

Scheme 5

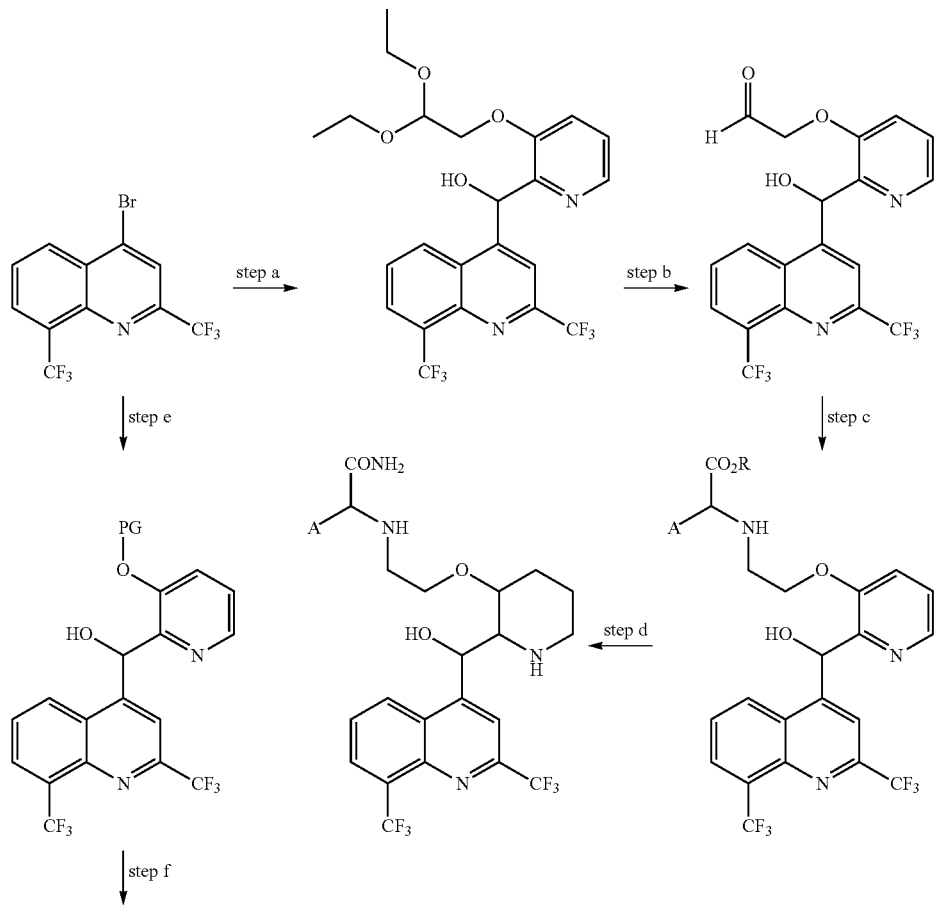

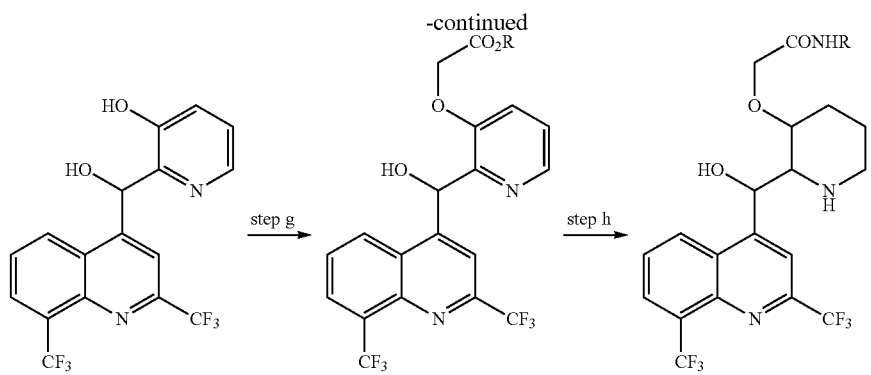

Scheme 6 shows the synthesis of additional mefloquine analogs with functionalized pendants on the piperidine ring. If 2-bromo-nicotinic acid is initially treated with sodium hydride in a solvent such as ether or THF at zero to −40 degrees C., and the mixture of the resultant salt is then reacted with n-BuLi at −40- to −70 degrees C., the 2-lithionicotinate salt can form. Addition of the quinolinyl aldehyde to a mixture of the lithionicotinate at low temperature can provide after warming and subsequent treatment with dilute acid the nocotinate adduct (step a). Coupling of this acid with anhydrous ammonia after treatment with isobuytyl chloroformate (IBCF) in methylene chloride in the presence of N-methylmorpholine at about zero degrees to ambient temperature, can give the carboxamide (step b). Hydrogenation of the pyridine ring may be accomplished using a catalyst, such as platinum oxide in ethanol, under a hydrogen atmosphere in the presence of hydrogen chloride (J Med Chem, 1968, 11, 267) to afford the piperidine adduct (step c). Alternatively, the pyridine carboxylic acid may be coupled with an amino acid ester, such as that of alanine, in the presence of HATU (2-(1H-7-azabenzotriazol-1-yl)-1,1,3,3-tetramethyl uronium hexafluorophosphate methanaminium) and DIPEA in methylene chloride, to yield the ester (step d). Hydrogenolysis of the pyridine ring, as previously described, may afford the piperidine (step e), and conversion of the ester to the carboxamide with anhydrous ammonia in ethanol cam provide the carboxamide (step f).

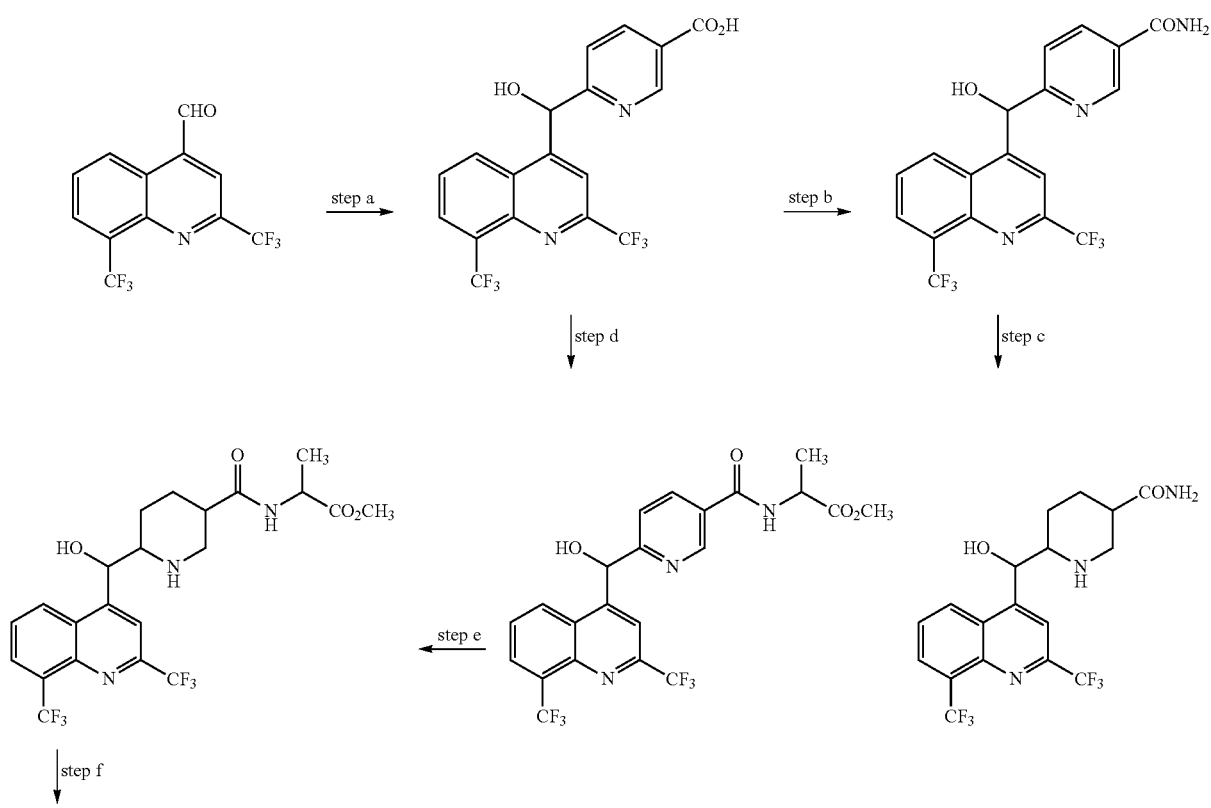

Scheme 6

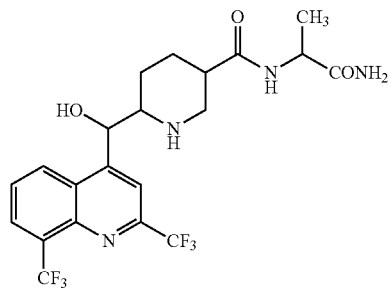

Scheme 7 shows the synthesis of mefloquine analogs with N-functionalized aminomethyl pendants on the piperidine ring. If the isoquinolinylcarboxaldehyde is treated with ethylene ketal of 6-lithiopyridine-3-carboxaldehyde, generated from the corresponding bromo-ketal and n-BuLi at low temperatures, the carbinol can result (step a). Hydrolysis of the ketal under acidic aqueous conditions should provide the carboxaldehyde (step b), and reductive amination with amino acid esters, such as that of glycine, using triacetoxyborohydride in the presence of acetic acid should afford the appended ester (step c). Reduction of the pyridine ring, as previously described, can give the piperidine ester (step d), and further treatment with anhydrous ammonia in alcohol should afford the carboxamide (step e).

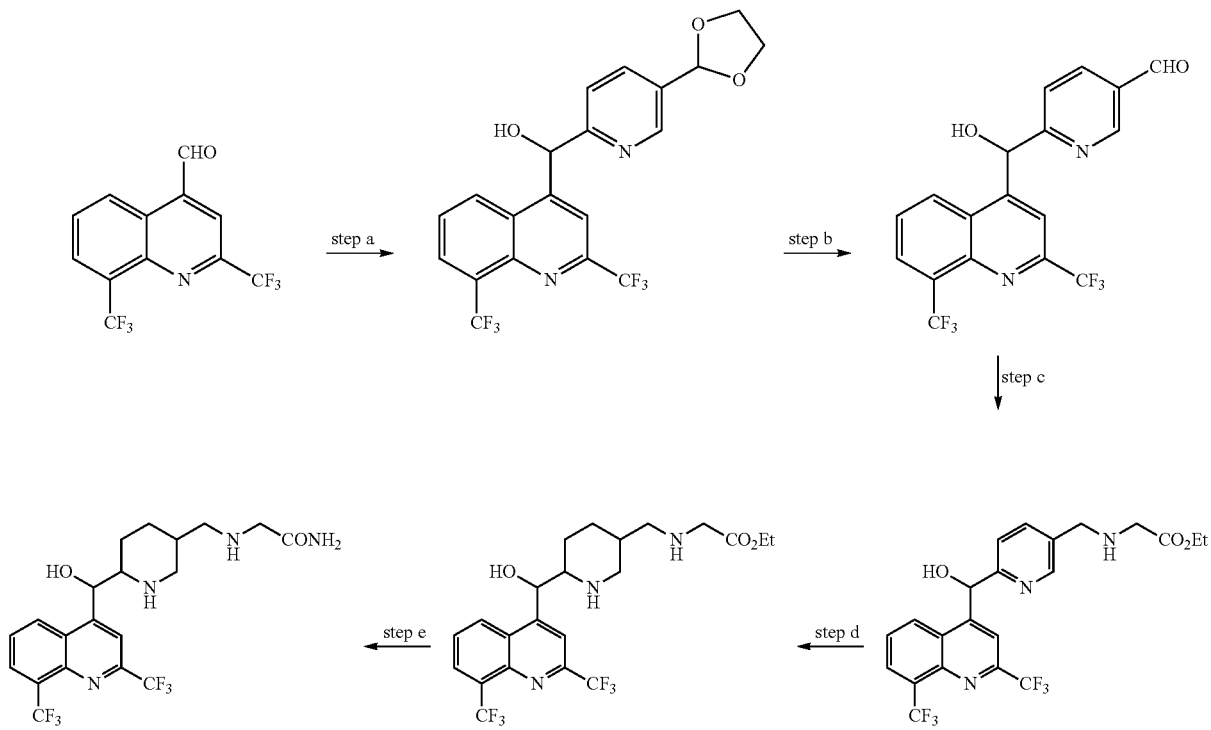

Scheme 8 shows another method of preparing seco-piperidine compounds with hydrophilic functional groups on the alkyl chains. If the isoquinolinylcarboxaldehyde is treated with cyanide anion under acidic conditions, the cyanohydrin may be produced (step a). Reduction of the nitrile using lithium aluminum hydride or with hydrogen in the presence of a catalyst such as palladium or platinum oxide can produce the amino alcohol (step b). Reductive amination of the carboxaldehyde with glyoxylic acid using sodium cyanoborohydride in the presence of acidic can yield the hydroxyethylamino ester, R=H (step c). Conversion of the ester to the amide may be achieved through aminolysis with ammonia (step d). Hydrolysis to the carboxylic acid using lithium hydroxide in aqueous THF solution (step e), followed by condensation with amino acid esters can yield the ester adduct (step 0 and aminolysis of this ester can also afford the carboxamide (step g).

lished chemistry. Condensation of 2-trifluoromethylaniline with an appropriately protected benzoylacetoacetate in the presence of PPA according to previously published procedures (J Med Chem, 1971, 14, 926) should provide the quinolone (step a) that is readily converted to the bromide using $POBr_3$ (step b). Conversion of the bromide to the formyl compound (step c) may be achieved using n-butyl lithium in ether at −78 degrees C. followed by addition of DMF (ChemMedChem, 2006, 1 593). Addition of 2-lithiopyridine at low temperature to the corresponding aldehyde should give the carbinol (step d). Removal of the oxygen protecting group gives the corresponding phenol (step e) that may be selectively alkylated with a variety of groups, using chemistry known to one skilled in the art, that are specifically targeted at reducing the compound's ability to cross the blood brain

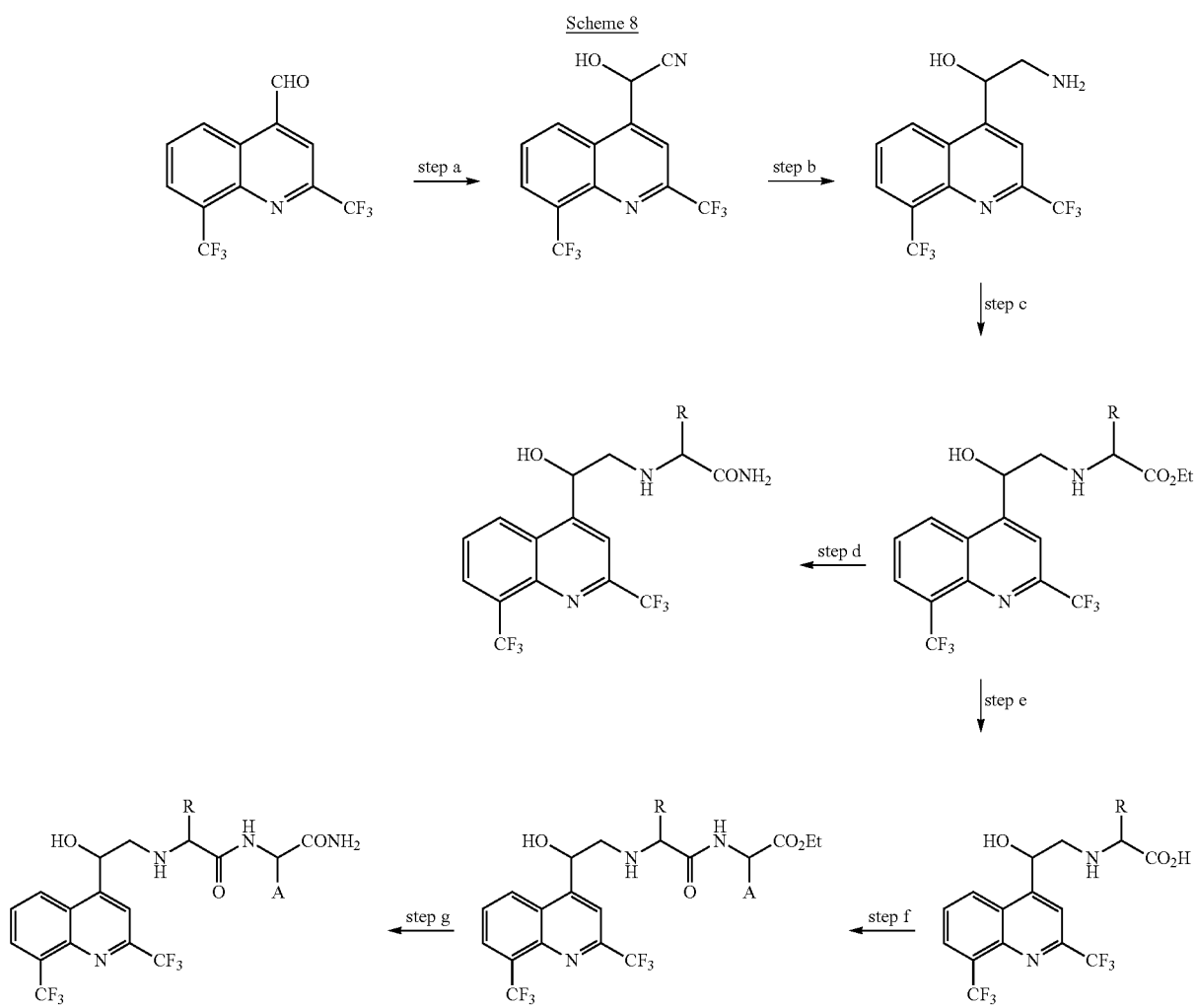

Scheme 8

Scheme 9 shows another method for the synthesis of modified mefloquinone analogs at the C-2 position of the quinoline moiety following a general route that utilizes well-established barrier as described in aspect 11. Catalytic hydrogenation using standard hydrogenation conditions should give rise to the corresponding piperidine (step f).

Scheme 9

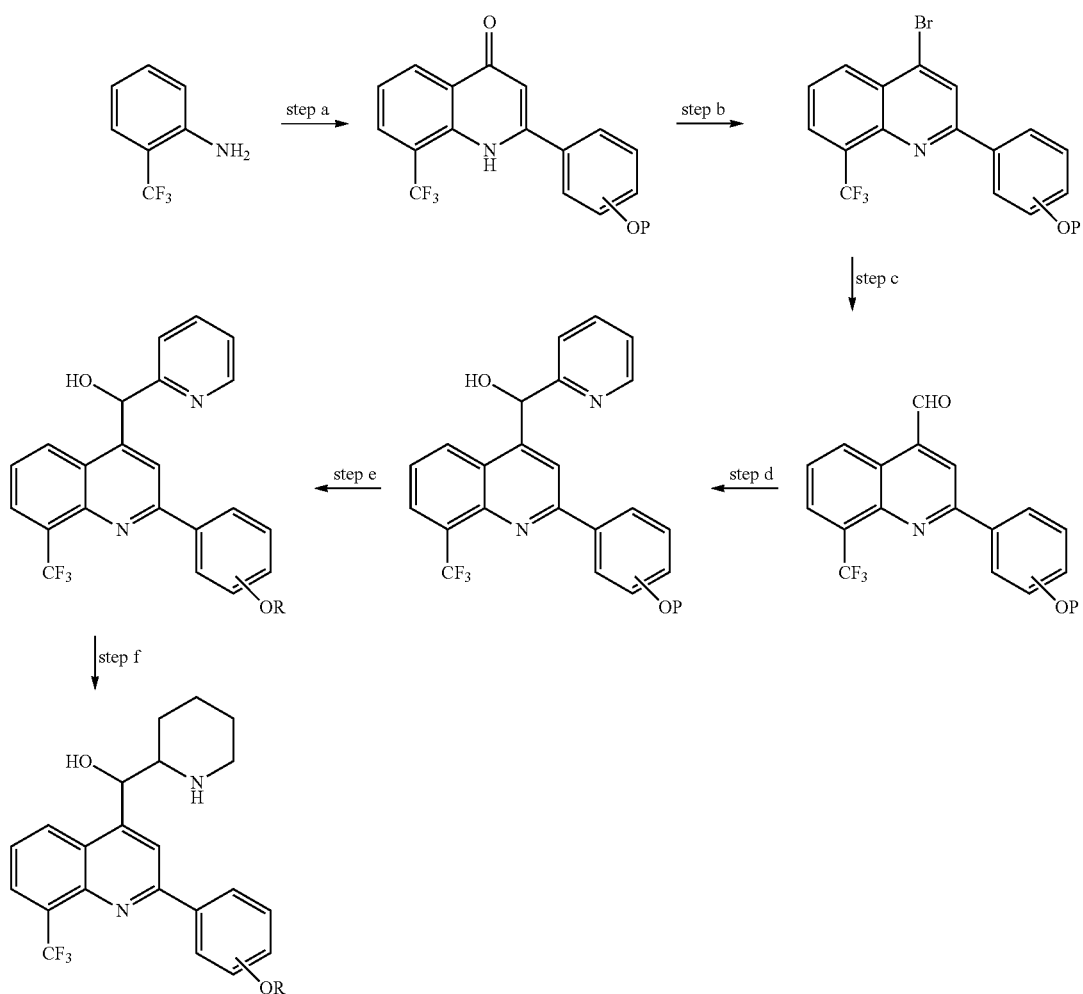

Scheme 10 shows another method for the synthesis of modified mefloquinone analogs at the C-2 position of the quinoline moiety following a general route that utilizes well established chemistry. Condensation of 2-trifluoromethylaniline with an appropriately protected benzoylacetoacetate in the presence of PPA according to previously published procedures (J Med Chem, 1971, 14, 926) should provide the quinolone (step a) that is readily converted to the bromide using $POBr_3$ (step b). Conversion of the bromide to the formyl compound (step c) may be achieved using n-butyl lithium in ether at −78 degrees C. followed by addition of DMF (ChemMedChem, 2006, 1 593). Addition of 2-lithiopyridine at low temperature to the corresponding aldehyde should give the carbinol (step d). Removal of the nitrogen protecting group gives the corresponding aniline (step e) that may be selectively modified with a variety of groups, using chemistry known to one skilled in the art, that are specifically targeted at reducing the compound's ability to cross the blood brain barrier as described in aspect 11. Catalytic hydrogenation using standard hydrogenation conditions should give rise to the corresponding piperidine (step f).

Scheme 10

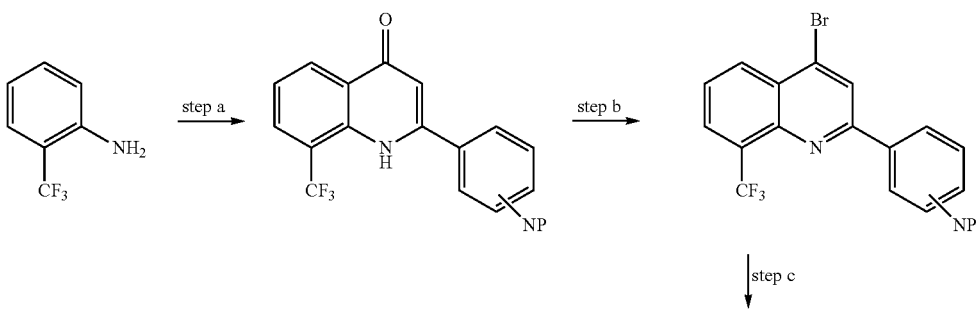

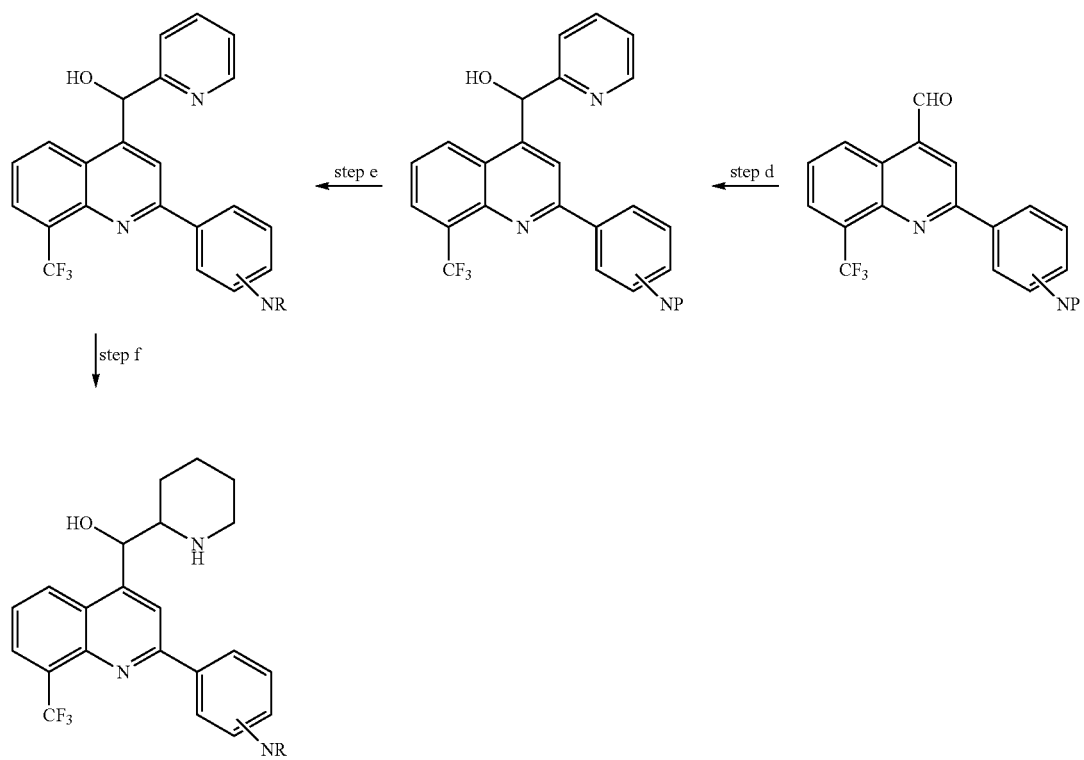

Scheme 11 shows another method for the synthesis of modified mefloquinone analogs at the C-2 position of the quinoline moiety following a general route that utilizes well established chemistry. The starting point for this synthetic scheme is the suitably protected analine intermediate previously described. The aniline protecting group is removed (step a) and the free amine is converted to a nitrile using the well known Sandmeyer reaction (T. Sandmeyer, Ber. 17 1633, 2650 1884). The benzonitrile is a very versatile intermediate and may be selectively converted into a variety of groups (step b), using chemistry known to one skilled in the art, that are specifically targeted at reducing the compound's ability to cross the blood brain barrier as described in aspect 11. Catalytic hydrogenation using standard hydrogenation conditions should give rise to the corresponding piperidine (step c).

Scheme 11

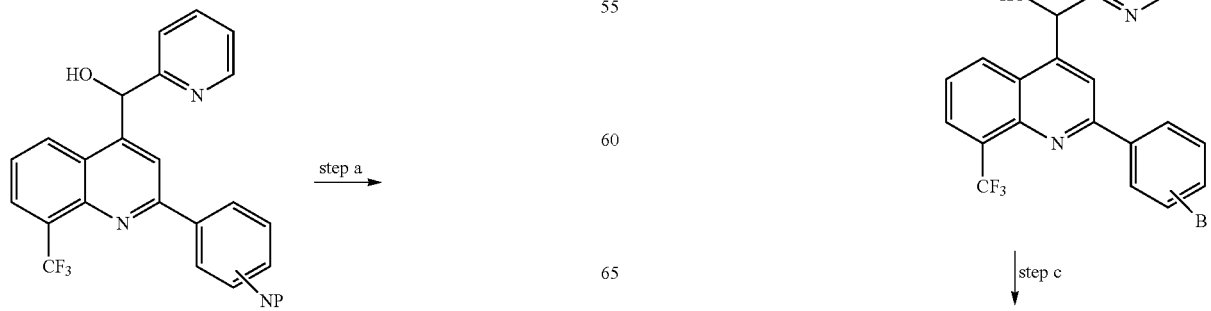

-continued

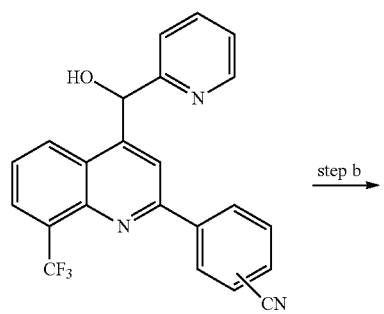

-continued

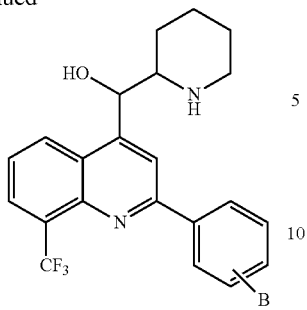

One stereoisomer of a compound of the present invention may be a more potent cannabinoid receptor antagonist than its counterpart(s). Thus, stereoisomers are included in the present invention. When required, separation of the racemic material may be achieved by HPLC using a chiral column or by a resolution using a resolving agent such as described in Wilen, S. H. *Tables of Resolving Agents and Optical Resolutions* 1972, 308 or using enantiomerically pure acids and bases. A chiral compound of the present invention may also be directly synthesized using a chiral catalyst or a chiral ligand, e.g., Jacobsen, E. *Acc. Chem. Res.* 2000, 33, $42_{1-4}31$ or using other enantio- and diastereo-selective reactions and reagents known to one skilled in the art of asymmetric synthesis.

Other features of the invention will become apparent in the course of the following descriptions of exemplary aspects that are given for illustration of the invention and are not intended to be limiting thereof.

EXAMPLES

Tables 1-7 show representative examples of the compounds of the present invention. Each example in each table represents an individual species of the present invention.

TABLE 1

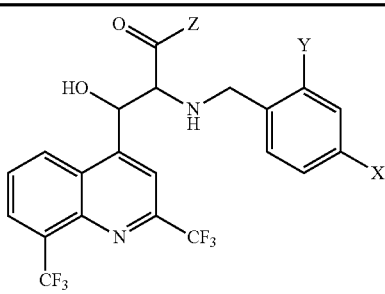

| Number | Z | X | Y |
|---|---|---|---|
| 1 | OEt | H | H |
| 2 | OH | H | H |
| 3 | NH$_2$ | H | H |
| 4 | NHOH | H | H |
| 5 | OEt | F | H |
| 6 | OH | F | H |
| 7 | NH$_2$ | F | H |
| 8 | NHOH | F | H |
| 9 | OEt | Cl | H |
| 10 | OH | Cl | H |
| 11 | NH$_2$ | Cl | H |
| 12 | NHOH | Cl | H |
| 13 | OEt | CH$_3$ | H |
| 14 | OH | CH$_3$ | H |
| 15 | NH$_2$ | CH$_3$ | H |

TABLE 1-continued

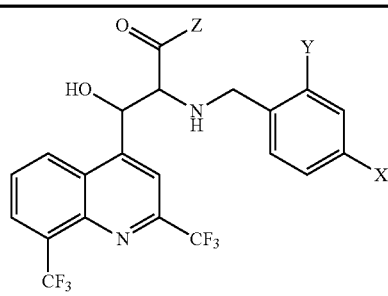

| Number | Z | X | Y |
|---|---|---|---|
| 16 | NHOH | CH$_3$ | H |
| 17 | OEt | OCH$_3$ | H |
| 18 | OH | OCH$_3$ | H |
| 19 | NH$_2$ | OCH$_3$ | H |
| 20 | NHOH | OCH$_3$ | H |
| 21 | OEt | H | Cl |
| 22 | OH | H | Cl |
| 23 | NH$_2$ | H | Cl |
| 24 | NHOH | H | Cl |
| 25 | OEt | F | Cl |
| 26 | OH | F | Cl |
| 27 | NH$_2$ | F | Cl |
| 28 | NHOH | F | Cl |
| 29 | OEt | Cl | Cl |
| 30 | OH | Cl | Cl |
| 31 | NH$_2$ | Cl | Cl |
| 32 | NHOH | Cl | Cl |
| 33 | OEt | CH$_3$ | Cl |
| 34 | OH | CH$_3$ | Cl |
| 35 | NH$_2$ | CH$_3$ | Cl |
| 36 | NHOH | CH$_3$ | Cl |
| 37 | CH(CH$_3$)CO$_2$Et | OCH$_3$ | Cl |
| 38 | CH(CH$_3$)CO$_2$H | OCH$_3$ | Cl |
| 39 | CH(CH$_3$)CONH$_2$ | OCH$_3$ | Cl |
| 40 | CH(CH$_3$)CONHOH | OCH$_3$ | Cl |

TABLE 2

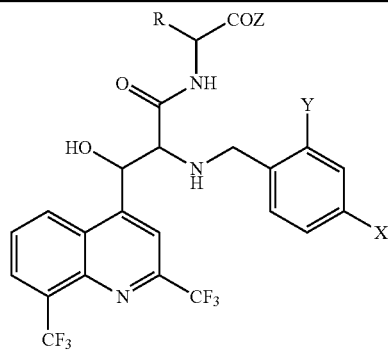

| Number | R | Z | X | Y |
|---|---|---|---|---|
| 1 | H | OEt | H | H |
| 2 | H | OH | H | H |
| 3 | H | NH$_2$ | H | H |
| 4 | H | NHOH | H | H |
| 5 | H | OEt | F | H |
| 6 | H | OH | F | H |
| 7 | H | NH$_2$ | F | H |
| 8 | H | NHOH | F | H |
| 9 | H | OEt | Cl | H |
| 10 | H | OH | Cl | H |
| 11 | H | NH$_2$ | Cl | H |
| 12 | H | NHOH | Cl | H |
| 13 | H | OEt | CH$_3$ | H |
| 14 | H | OH | CH$_3$ | H |

TABLE 2-continued

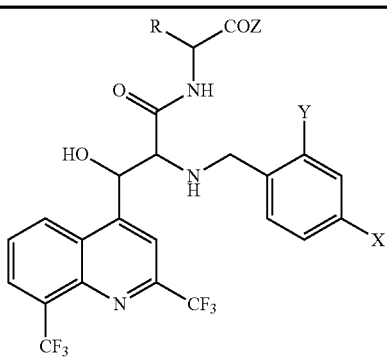

| Number | R | Z | X | Y |
|---|---|---|---|---|
| 15 | H | NH$_2$ | CH$_3$ | H |
| 16 | H | NHOH | CH$_3$ | H |
| 17 | H | OEt | OCH$_3$ | H |
| 18 | H | OH | OCH$_3$ | H |
| 19 | H | NH$_2$ | OCH$_3$ | H |
| 20 | H | NHOH | OCH$_3$ | H |
| 21 | H | OEt | H | Cl |
| 22 | H | OH | H | Cl |
| 23 | H | NH$_2$ | H | Cl |
| 24 | H | NHOH | H | Cl |
| 25 | H | OEt | F | Cl |
| 26 | H | OH | F | Cl |
| 27 | H | NH$_2$ | F | Cl |
| 28 | H | NHOH | F | Cl |
| 29 | H | OEt | Cl | Cl |
| 30 | H | OH | Cl | Cl |
| 31 | H | NH$_2$ | Cl | Cl |
| 32 | H | NHOH | Cl | Cl |
| 33 | H | OEt | CH$_3$ | Cl |
| 34 | H | OH | CH$_3$ | Cl |
| 35 | H | NH$_2$ | CH$_3$ | Cl |
| 36 | H | NHOH | CH$_3$ | Cl |
| 37 | H | OEt | OCH$_3$ | Cl |
| 38 | H | OH | OCH$_3$ | Cl |
| 39 | H | NH$_2$ | OCH$_3$ | Cl |
| 40 | H | NHOH | OCH$_3$ | Cl |
| 41 | CH$_3$ | OEt | H | H |
| 42 | CH$_3$ | OH | H | H |
| 43 | CH$_3$ | NH$_2$ | H | H |
| 44 | CH$_3$ | NHOH | H | H |
| 45 | CH$_3$ | OEt | F | H |
| 46 | CH$_3$ | OH | F | H |
| 47 | CH$_3$ | NH$_2$ | F | H |
| 48 | CH$_3$ | NHOH | F | H |
| 49 | CH$_3$ | OEt | Cl | H |
| 50 | CH$_3$ | OH | Cl | H |
| 51 | CH$_3$ | NH$_2$ | Cl | H |
| 52 | CH$_3$ | NHOH | Cl | H |
| 53 | CH$_3$ | OEt | CH$_3$ | H |
| 54 | CH$_3$ | OH | CH$_3$ | H |
| 55 | CH$_3$ | NH$_2$ | CH$_3$ | H |
| 56 | CH$_3$ | NHOH | CH$_3$ | H |
| 57 | CH$_3$ | OEt | OCH$_3$ | H |
| 58 | CH$_3$ | OH | OCH$_3$ | H |
| 59 | CH$_3$ | NH$_2$ | OCH$_3$ | H |
| 60 | CH$_3$ | NHOH | OCH$_3$ | H |
| 61 | CH$_3$ | OEt | H | Cl |
| 62 | CH$_3$ | OH | H | Cl |
| 63 | CH$_3$ | NH$_2$ | H | Cl |
| 64 | CH$_3$ | NHOH | H | Cl |
| 65 | CH$_3$ | OEt | F | Cl |
| 66 | CH$_3$ | OH | F | Cl |
| 67 | CH$_3$ | NH$_2$ | F | Cl |
| 68 | CH$_3$ | NHOH | F | Cl |
| 69 | CH$_3$ | OEt | Cl | Cl |
| 70 | CH$_3$ | OH | Cl | Cl |
| 71 | CH$_3$ | NH$_2$ | Cl | Cl |
| 72 | CH$_3$ | NHOH | Cl | Cl |
| 73 | CH$_3$ | OEt | CH$_3$ | Cl |
| 74 | CH$_3$ | OH | CH$_3$ | Cl |

TABLE 2-continued

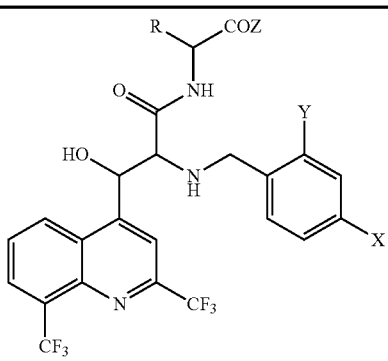

| Number | R | Z | X | Y |
|---|---|---|---|---|
| 75 | CH$_3$ | NH$_2$ | CH$_3$ | Cl |
| 76 | CH$_3$ | NHOH | CH$_3$ | Cl |
| 77 | CH$_3$ | OEt | OCH$_3$ | Cl |
| 78 | CH$_3$ | OH | OCH$_3$ | Cl |
| 79 | CH$_3$ | NH$_2$ | OCH$_3$ | Cl |
| 80 | CH$_3$ | NHOH | OCH$_3$ | Cl |

TABLE 3

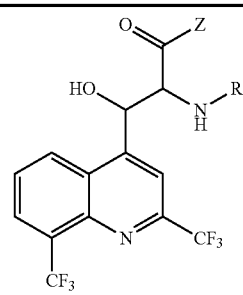

| Number | Z | R |
|---|---|---|
| 1 | OEt | H |
| 2 | OH | H |
| 3 | NH$_2$ | H |
| 4 | NHOH | H |
| 5 | NHCHCH$_3$CH$_2$OH | H |
| 6 | OEt | CH$_3$ |
| 7 | OH | CH$_3$ |
| 8 | NH$_2$ | CH$_3$ |
| 9 | NHOH | CH$_3$ |
| 10 | NHCHCH$_3$CH$_2$OH | CH$_3$ |
| 11 | OEt | CH$_2$CH$_3$ |
| 12 | OH | CH$_2$CH$_3$ |
| 13 | NH$_2$ | CH$_2$CH$_3$ |
| 14 | NHOH | CH$_2$CH$_3$ |
| 15 | NHCHCH$_3$CH$_2$OH | CH$_2$CH$_3$ |
| 16 | OEt | CH(CH$_3$)$_2$ |
| 17 | OH | CH(CH$_3$)$_2$ |
| 18 | NH$_2$ | CH(CH$_3$)$_2$ |
| 19 | NHOH | CH(CH$_3$)$_2$ |
| 20 | NHCHCH$_3$CH$_2$OH | CH(CH$_3$)$_2$ |
| 21 | OEt | cyclohexyl |
| 22 | OH | cyclohexyl |
| 23 | NH$_2$ | cyclohexyl |
| 24 | NHOH | cyclohexyl |
| 25 | NHCHCH$_3$CH$_2$OH | cyclohexyl |
| 26 | OEt | cyclopentyl |
| 27 | OH | cyclopentyl |
| 28 | NH$_2$ | cyclopentyl |
| 29 | NHOH | cyclopentyl |
| 30 | NHCHCH$_3$CH$_2$OH | cyclopentyl |
| 31 | NHCH$_2$CO$_2$Et | H |
| 32 | NHCH$_2$CO$_2$H$_2$ | H |
| 33 | NHCH$_2$CONH$_2$ | H |

TABLE 3-continued

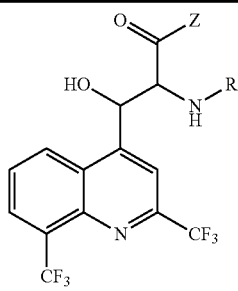

| Number | Z | R |
|---|---|---|
| 34 | NHCH$_2$CONHOH | H |
| 35 | NHCH$_2$CONHCHCH$_3$CH$_2$OH | H |
| 36 | NHCH$_2$CO$_2$Et | CH$_3$ |
| 37 | NHCH$_2$CO$_2$H$_2$ | CH$_3$ |
| 38 | NHCH$_2$CONH$_2$ | CH$_3$ |
| 39 | NHCH$_2$CONHOH | CH$_3$ |
| 40 | NHCH$_2$CONHCHCH$_3$CH$_2$OH | CH$_3$ |
| 41 | NHCH$_2$CO$_2$Et | CH$_2$CH$_3$ |
| 42 | NHCH$_2$CO$_2$H$_2$ | CH$_2$CH$_3$ |
| 43 | NHCH$_2$CONH$_2$ | CH$_2$CH$_3$ |
| 44 | NHCH$_2$CONHOH | CH$_2$CH$_3$ |
| 45 | NHCH$_2$CONHCHCH$_3$CH$_2$OH | CH$_2$CH$_3$ |
| 46 | NHCH$_2$CO$_2$Et | CH(CH$_3$)$_2$ |
| 47 | NHCH$_2$CO$_2$H$_2$ | CH(CH$_3$)$_2$ |
| 48 | NHCH$_2$CONH$_2$ | CH(CH$_3$)$_2$ |
| 49 | NHCH$_2$CONHOH | CH(CH$_3$)$_2$ |
| 50 | NHCH$_2$CONHCHCH$_3$CH$_2$OH | CH(CH$_3$)$_2$ |
| 51 | NHCH$_2$CO$_2$Et | cyclohexyl |
| 52 | NHCH$_2$CO$_2$H$_2$ | cyclohexyl |
| 53 | NHCH$_2$CONH$_2$ | cyclohexyl |
| 54 | NHCH$_2$CONHOH | cyclohexyl |
| 55 | NHCH$_2$CONHCHCH$_3$CH$_2$OH | cyclohexyl |
| 56 | NHCH$_2$CO$_2$Et | cyclopentyl |
| 57 | NHCH$_2$CO$_2$H$_2$ | cyclopentyl |
| 58 | NHCH$_2$CONH$_2$ | cyclopentyl |
| 59 | NHCH$_2$CONHOH | cyclopentyl |
| 60 | NHCH$_2$CONHCHCH$_3$CH$_2$OH | cyclopentyl |

TABLE 4

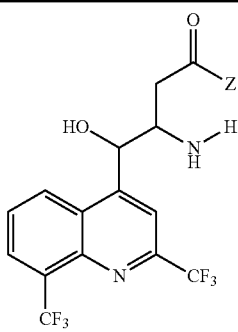

| Number | Z | R |
|---|---|---|
| 1 | OEt | H |
| 2 | OH | H |
| 3 | NH$_2$ | H |
| 4 | NHOH | H |
| 5 | NHCHCH$_3$CH$_2$OH | H |
| 6 | OEt | CH$_3$ |
| 7 | OH | CH$_3$ |
| 8 | NH$_2$ | CH$_3$ |
| 9 | NHOH | CH$_3$ |
| 10 | NHCHCH$_3$CH$_2$OH | CH$_3$ |
| 11 | OEt | CH$_2$CH$_3$ |
| 12 | OH | CH$_2$CH$_3$ |
| 13 | NH$_2$ | CH$_2$CH$_3$ |

TABLE 4-continued

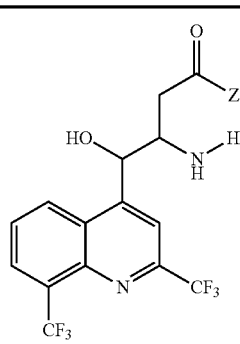

| Number | Z | R |
|---|---|---|
| 14 | NHOH | CH$_2$CH$_3$ |
| 15 | NHCHCH$_3$CH$_2$OH | CH$_2$CH$_3$ |
| 16 | OEt | CH(CH$_3$)$_2$ |
| 17 | OH | CH(CH$_3$)$_2$ |
| 18 | NH$_2$ | CH(CH$_3$)$_2$ |
| 19 | NHOH | CH(CH$_3$)$_2$ |
| 20 | NHCHCH$_3$CH$_2$OH | CH(CH$_3$)$_2$ |
| 21 | OEt | Cyclohexyl |
| 22 | OH | Cyclohexyl |
| 23 | NH$_2$ | Cyclohexyl |
| 24 | NHOH | Cyclohexyl |
| 25 | NHCHCH$_3$CH$_2$OH | Cyclohexyl |
| 26 | OEt | Cyclopentyl |
| 27 | OH | Cyclopentyl |
| 28 | NH$_2$ | Cyclopentyl |
| 29 | NHOH | Cyclopentyl |
| 30 | NHCHCH$_3$CH$_2$OH | Cyclopentyl |
| 31 | NHCH$_2$CO$_2$Et | H |
| 32 | NHCH$_2$CO$_2$H$_2$ | H |
| 33 | NHCH$_2$CONH$_2$ | H |
| 34 | NHCH$_2$CONHOH | H |
| 35 | NHCH$_2$CONHCHCH$_3$CH$_2$OH | H |
| 36 | NHCH$_2$CO$_2$Et | CH$_3$ |
| 37 | NHCH$_2$CO$_2$H$_2$ | CH$_3$ |
| 38 | NHCH$_2$CONH$_2$ | CH$_3$ |
| 39 | NHCH$_2$CONHOH | CH$_3$ |
| 40 | NHCH$_2$CONHCHCH$_3$CH$_2$OH | CH$_3$ |
| 41 | NHCH$_2$CO$_2$Et | CH$_2$CH$_3$ |
| 42 | NHCH$_2$CO$_2$H$_2$ | CH$_2$CH$_3$ |
| 43 | NHCH$_2$CONH$_2$ | CH$_2$CH$_3$ |
| 44 | NHCH$_2$CONHOH | CH$_2$CH$_3$ |
| 45 | NHCH$_2$CONHCHCH$_3$CH$_2$OH | CH$_2$CH$_3$ |
| 46 | NHCH$_2$CO$_2$Et | CH(CH$_3$)$_2$ |
| 47 | NHCH$_2$CO$_2$H$_2$ | CH(CH$_3$)$_2$ |
| 48 | NHCH$_2$CONH$_2$ | CH(CH$_3$)$_2$ |
| 49 | NHCH$_2$CONHOH | CH(CH$_3$)$_2$ |
| 50 | NHCH$_2$CONHCHCH$_3$CH$_2$OH | CH(CH$_3$)$_2$ |
| 51 | NHCH$_2$CO$_2$Et | Cyclohexyl |
| 52 | NHCH$_2$CO$_2$H$_2$ | Cyclohexyl |
| 53 | NHCH$_2$CONH$_2$ | Cyclohexyl |
| 54 | NHCH$_2$CONHOH | Cyclohexyl |
| 55 | NHCH$_2$CONHCHCH$_3$CH$_2$OH | Cyclohexyl |
| 56 | NHCH$_2$CO$_2$Et | Cyclopentyl |
| 57 | NHCH$_2$CO$_2$H$_2$ | Cyclopentyl |
| 58 | NHCH$_2$CONH$_2$ | Cyclopentyl |
| 59 | NHCH$_2$CONHOH | Cyclopentyl |
| 60 | NHCH$_2$CONHCHCH$_3$CH$_2$OH | Cyclopentyl |

TABLE 5

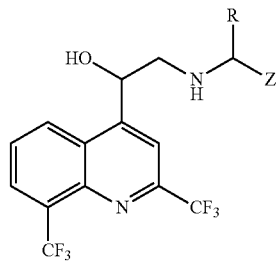

| Number | Z | R |
|---|---|---|
| 1 | CO$_2$Et | H |
| 2 | CO$_2$H | H |
| 3 | CONH$_2$ | H |
| 4 | CONHOH | H |
| 5 | CONHCHCH$_3$CH$_2$OH | H |
| 6 | CO$_2$Et | CH$_3$ |
| 7 | CO$_2$H | CH$_3$ |
| 8 | CONH$_2$ | CH$_3$ |
| 9 | CONHOH | CH$_3$ |
| 10 | CONHCHCH$_3$CH$_2$OH | CH$_3$ |
| 11 | CO$_2$Et | CH$_2$CH$_3$ |
| 12 | CO$_2$H | CH$_2$CH$_3$ |
| 13 | CONH$_2$ | CH$_2$CH$_3$ |
| 14 | CONHOH | CH$_2$CH$_3$ |
| 15 | CONHCHCH$_3$CH$_2$OH | CH$_2$CH$_3$ |
| 16 | CO$_2$Et | CH(CH$_3$)$_2$ |
| 17 | CO$_2$H | CH(CH$_3$)$_2$ |
| 18 | CONH$_2$ | CH(CH$_3$)$_2$ |
| 19 | CONHOH | CH(CH$_3$)$_2$ |
| 20 | CONHCHCH$_3$CH$_2$OH | CH(CH$_3$)$_2$ |
| 21 | CO$_2$Et | CH$_2$CH(CH$_3$)$_2$ |
| 22 | CO$_2$H | CH$_2$CH(CH$_3$)$_2$ |
| 23 | CONH$_2$ | CH$_2$CH(CH$_3$)$_2$ |
| 24 | CONHOH | CH$_2$CH(CH$_3$)$_2$ |
| 25 | CONHCHCH$_3$CH$_2$OH | CH$_2$CH(CH$_3$)$_2$ |
| 26 | CO$_2$Et | cyclohexyl |
| 27 | CO$_2$H | cyclohexyl |
| 28 | CONH$_2$ | cyclohexyl |
| 29 | CONHOH | cyclohexyl |
| 30 | CONHCHCH$_3$CH$_2$OH | cyclohexyl |
| 31 | CO$_2$Et | CHOH(CH$_3$)$_2$ |
| 32 | CO$_2$H | CHOH(CH$_3$)$_2$ |
| 33 | CONH$_2$ | CHOH(CH$_3$)$_2$ |
| 34 | CONHOH | CHOH(CH$_3$)$_2$ |
| 35 | CONHCHCH$_3$CH$_2$OH | CHOH(CH$_3$)$_2$ |
| 36 | CONHCH$_2$CO$_2$Et | H |
| 37 | CONHCH$_2$CO$_2$H | H |
| 38 | CONHCH$_2$CONH$_2$ | H |
| 39 | CONHCH$_2$CONHOH | H |
| 40 | CONHCH$_2$CONHCHCH$_3$CH$_2$OH | H |
| 41 | CONHCH$_2$CO$_2$Et | CH$_3$ |
| 42 | CONHCH$_2$CO$_2$H | CH$_3$ |
| 43 | CONHCH$_2$CONH$_2$ | CH$_3$ |
| 44 | CONHCH$_2$CONHOH | CH$_3$ |
| 45 | CONHCH$_2$CONHCHCH$_3$CH$_2$OH | CH$_3$ |
| 46 | CONHCH$_2$CO$_2$Et | CH$_2$CH$_3$ |
| 47 | CONHCH$_2$CO$_2$H | CH$_2$CH$_3$ |
| 48 | CONHCH$_2$CONH$_2$ | CH$_2$CH$_3$ |
| 49 | CONHCH$_2$CONHOH | CH$_2$CH$_3$ |
| 50 | CONHCH$_2$CONHCHCH$_3$CH$_2$OH | CH$_2$CH$_3$ |
| 51 | CONHCH$_2$CO$_2$Et | CH(CH$_3$)$_2$ |
| 52 | CONHCH$_2$CO$_2$H | CH(CH$_3$)$_2$ |
| 53 | CONHCH$_2$CONH$_2$ | CH(CH$_3$)$_2$ |
| 54 | CONHCH$_2$CONHOH | CH(CH$_3$)$_2$ |
| 55 | CONHCH$_2$CONHCHCH$_3$CH$_2$OH | CH(CH$_3$)$_2$ |
| 56 | CONHCH$_2$CO$_2$Et | cyclohexyl |
| 57 | CONHCH$_2$CO$_2$H | cyclohexyl |
| 58 | CONHCH$_2$CONH$_2$ | cyclohexyl |
| 59 | CONHCH$_2$CONHOH | cyclohexyl |
| 60 | CONHCH$_2$CONHCHCH$_3$CH$_2$OH | cyclohexyl |
| 61 | CONHCH$_2$CO$_2$Et | CHOH(CH$_3$)$_2$ |
| 62 | CONHCH$_2$CO$_2$H | CHOH(CH$_3$)$_2$ |
| 63 | CONHCH$_2$CONH$_2$ | CHOH(CH$_3$)$_2$ |
| 64 | CONHCH$_2$CONHOH | CHOH(CH$_3$)$_2$ |

TABLE 5-continued

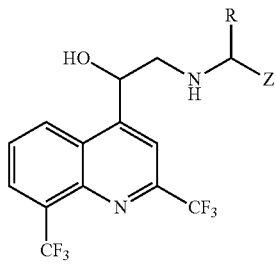

| Number | Z | R |
|---|---|---|
| 65 | CONHCH$_2$CONHCHCH$_3$CH$_2$OH | CHOH(CH$_3$)$_2$ |
| 66 | H | CH$_2$CH$_2$CO$_2$Et |
| 67 | H | CH$_2$CH$_2$CO$_2$H |
| 68 | H | CH$_2$CH$_2$CONH$_2$ |
| 69 | H | CH$_2$CH$_2$CONHOH |
| 70 | H | CH$_2$CH$_2$CONHCH$_2$CH$_2$OH |
| 71 | H | CH$_2$CHOHCO$_2$Et |
| 72 | H | CH$_2$CHOHCO$_2$H |
| 73 | H | CH$_2$CHOHCONH$_2$ |
| 74 | H | CH$_2$CHOHCONHOH |
| 75 | H | CH$_2$CHOHCONHCH$_2$CH$_2$OH |
| 76 | H | CHOHCH$_2$CO$_2$Et |
| 77 | H | CHOHCH$_2$CO$_2$H |
| 78 | H | CHOHCH$_2$CONH$_2$ |
| 79 | H | CHOHCH$_2$CONHOH |
| 80 | H | CHOHCH$_2$CONHCH$_2$CH$_2$OH |
| 81 | H | CH═CHCO$_2$Et |
| 82 | H | CH═CHCO$_2$H |
| 83 | H | CH═CHCONH$_2$ |
| 84 | H | CH═CHCONHOH |
| 85 | H | CH═CHCONHCH$_2$CH$_2$OH |
| 86 | CH$_3$ | CH$_2$CO$_2$Et |
| 87 | CH$_3$ | CH$_2$CO$_2$H |
| 88 | CH$_3$ | CH$_2$CONH$_2$ |
| 89 | CH$_3$ | CH$_2$CONHOH |
| 90 | CH$_3$ | CH$_2$CONHCH$_2$CH$_2$OH |

TABLE 6

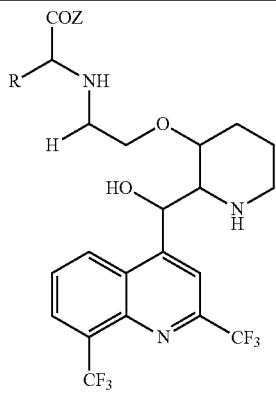

| Number | Z | R |
|---|---|---|
| 1 | OEt | H |
| 2 | OH | H |
| 3 | NH$_2$ | H |
| 4 | NHOH | H |
| 5 | NHCHCH$_3$CH$_2$OH | H |
| 6 | OEt | CH$_3$ |
| 7 | OH | CH$_3$ |
| 8 | NH$_2$ | CH$_3$ |
| 9 | NHOH | CH$_3$ |
| 10 | NHCHCH$_3$CH$_2$OH | CH$_3$ |
| 11 | OEt | CH$_2$CH$_3$ |
| 12 | OH | CH$_2$CH$_3$ |

TABLE 6-continued

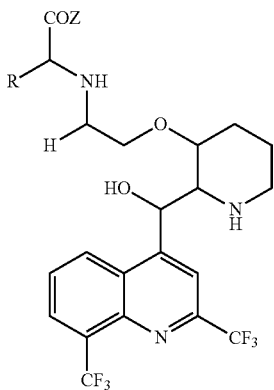

| Number | Z | R |
|---|---|---|
| 13 | NH$_2$ | CH$_2$CH$_3$ |
| 14 | NHOH | CH$_2$CH$_3$ |
| 15 | NHCHCH$_3$CH$_2$OH | CH$_2$CH$_3$ |
| 16 | OEt | CH(CH$_3$)$_2$ |
| 17 | OH | CH(CH$_3$)$_2$ |
| 18 | NH$_2$ | CH(CH$_3$)$_2$ |
| 19 | NHOH | CH(CH$_3$)$_2$ |
| 20 | NHCHCH$_3$CH$_2$OH | CH(CH$_3$)$_2$ |
| 21 | OEt | CH$_2$CH(CH$_3$)$_2$ |
| 22 | OH | CH$_2$CH(CH$_3$)$_2$ |
| 23 | NH$_2$ | CH$_2$CH(CH$_3$)$_2$ |
| 24 | NHOH | CH$_2$CH(CH$_3$)$_2$ |
| 25 | NHCHCH$_3$CH$_2$OH | CH$_2$CH(CH$_3$)$_2$ |
| 26 | OEt | cyclohexyl |
| 27 | OH | cyclohexyl |
| 28 | NH$_2$ | cyclohexyl |
| 29 | NHOH | cyclohexyl |
| 30 | NHCHCH$_3$CH$_2$OH | cyclohexyl |
| 31 | OEt | CHOH(CH$_3$)$_2$ |
| 32 | OH | CHOH(CH$_3$)$_2$ |
| 33 | NH$_2$ | CHOH(CH$_3$)$_2$ |
| 34 | NHOH | CHOH(CH$_3$)$_2$ |
| 35 | NHCHCH$_3$CH$_2$OH | CHOH(CH$_3$)$_2$ |
| 36 | NHCH$_2$CO$_2$Et | H |
| 37 | NHCH$_2$CO$_2$H | H |
| 38 | NHCH$_2$CONH$_2$ | H |
| 39 | NHCH$_2$CONHOH | H |
| 40 | NHCH$_2$CONHCHCH$_3$CH$_2$OH | H |
| 41 | NHCH$_2$CO$_2$Et | CH$_3$ |
| 42 | NHCH$_2$CO$_2$H | CH$_3$ |
| 43 | NHCH$_2$CONH$_2$ | CH$_3$ |
| 44 | NHCH$_2$CONHOH | CH$_3$ |
| 45 | NHCH$_2$CONHCHCH$_3$CH$_2$OH | CH$_3$ |
| 46 | NHCH$_2$CO$_2$Et | CH$_2$CH$_3$ |
| 47 | NHCH$_2$CO$_2$H | CH$_2$CH$_3$ |
| 48 | NHCH$_2$CONH | CH$_2$CH$_3$ |
| 49 | NHCH$_2$CONHOH | CH$_2$CH$_3$ |
| 50 | NHCH$_2$CONHCHCH$_3$CH$_2$OH | CH$_2$CH$_3$ |
| 51 | NHCH$_2$CO$_2$Et | CH(CH$_3$)$_2$ |
| 52 | NHCH$_2$CO$_2$H | CH(CH$_3$)$_2$ |
| 53 | NHCH$_2$CONH$_2$ | CH(CH$_3$)$_2$ |
| 54 | NHCH$_2$CONHOH | CH(CH$_3$)$_2$ |
| 55 | NHCH$_2$CONHCHCH$_3$CH$_2$OH | CH(CH$_3$)$_2$ |
| 56 | NHCH$_2$CO$_2$Et | cyclohexyl |
| 57 | NHCH$_2$CO$_2$H | cyclohexyl |
| 58 | NHCH$_2$CONH$_2$ | cyclohexyl |
| 59 | NHCH$_2$CONHOH | cyclohexyl |
| 60 | NHCH$_2$CONHCHCH$_3$CH$_2$OH | cyclohexyl |
| 61 | NHCH$_2$CO$_2$Et | CHOH(CH$_3$)$_2$ |
| 62 | NHCH$_2$CO$_2$H | CHOH(CH$_3$)$_2$ |
| 63 | NHCH$_2$CONH$_2$ | CHOH(CH$_3$)$_2$ |
| 64 | NHCH$_2$CONHOH | CHOH(CH$_3$)$_2$ |
| 65 | NHCH$_2$CONHCHCH$_3$CH$_2$OH | CHOH(CH$_3$)$_2$ |

TABLE 7

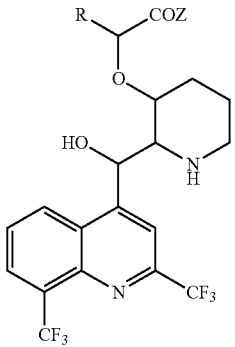

| Number | Z | R |
|---|---|---|
| 1 | OEt | H |
| 2 | OH | H |
| 3 | NH$_2$ | H |
| 4 | NHOH | H |
| 5 | NHCHCH$_3$CH$_2$OH | H |
| 6 | OEt | CH$_3$ |
| 7 | OH | CH$_3$ |
| 8 | NH$_2$ | CH$_3$ |
| 9 | NHOH | CH$_3$ |
| 10 | NHCHCH$_3$CH$_2$OH | CH$_3$ |
| 11 | OEt | C$_6$H$_5$ |
| 12 | OH | C$_6$H$_5$ |
| 13 | NH$_2$ | C$_6$H$_5$ |
| 14 | NHOH | C$_6$H$_5$ |
| 15 | NHCHCH$_3$CH$_2$OH | C$_6$H$_5$ |
| 16 | NHCH$_2$CO$_2$Et | H |
| 17 | NHCH$_2$CO$_2$H | H |
| 18 | NHCH$_2$CONH$_2$ | H |
| 19 | NHCH$_2$CONHOH | H |
| 20 | NHCH$_2$CONHCHCH$_3$CH$_2$OH | H |
| 21 | NHCH$_2$CO$_2$Et | CH$_3$ |
| 22 | NHCH$_2$CO$_2$H | CH$_3$ |
| 23 | NHCH$_2$CONH$_2$ | CH$_3$ |
| 24 | NHCH$_2$CONHOH | CH$_3$ |
| 25 | NHCH$_2$CONHCHCH$_3$CH$_2$OH | CH$_3$ |
| 26 | NHCH$_2$CO$_2$Et | C$_6$H$_5$ |
| 27 | NHCH$_2$CO$_2$H | C$_6$H$_5$ |
| 28 | NHCH$_2$CONH | C$_6$H$_5$ |
| 29 | NHCH$_2$CONHOH | C$_6$H$_5$ |
| 30 | NHCH$_2$CONHCHCH$_3$CH$_2$OH | C$_6$H$_5$ |

TABLE 8

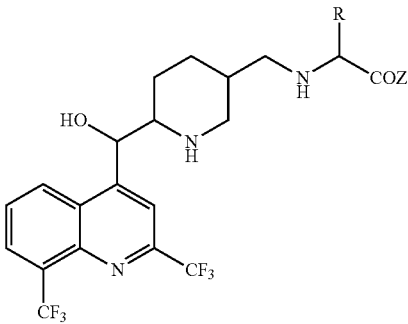

| Number | Z | R |
|---|---|---|
| 1 | OEt | H |
| 2 | OH | H |
| 3 | NH$_2$ | H |
| 4 | NHOH | H |
| 5 | NHCHCH$_3$CH$_2$OH | H |
| 6 | OEt | CH$_3$ |
| 7 | OH | CH$_3$ |

TABLE 8-continued

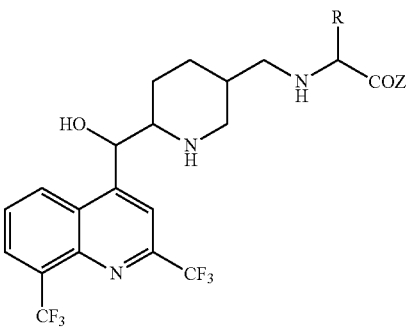

| Number | Z | R |
|---|---|---|
| 8 | NH$_2$ | CH$_3$ |
| 9 | NHOH | CH$_3$ |
| 10 | NHCHCH$_3$CH$_2$OH | CH$_3$ |
| 11 | OEt | CH$_2$OH |
| 12 | OH | CH$_2$OH |
| 13 | NH$_2$ | CH$_2$OH |
| 14 | NHOH | CH$_2$OH |
| 15 | NHCHCH$_3$CH$_2$OH | CH$_2$OH |
| 16 | NHCH$_2$CO$_2$Et | H |
| 17 | NHCH$_2$CO$_2$H | H |
| 18 | NHCH$_2$CONH$_2$ | H |
| 19 | NHCH$_2$CONHOH | H |
| 20 | NHCH$_2$CONHCHCH$_3$CH$_2$OH | H |
| 21 | NHCH$_2$CO$_2$Et | CH$_3$ |
| 22 | NHCH$_2$CO$_2$H | CH$_3$ |
| 23 | NHCH$_2$CONH$_2$ | CH$_3$ |
| 24 | NHCH$_2$CONHOH | CH$_3$ |
| 25 | NHCH$_2$CONHCHCH$_3$CH$_2$OH | CH$_3$ |
| 26 | NHCH$_2$CO$_2$Et | CH$_2$OH |
| 27 | NHCH$_2$CO$_2$H | CH$_2$OH |
| 28 | NHCH$_2$CONH | CH$_2$OH |
| 29 | NHCH$_2$CONHOH | CH$_2$OH |
| 30 | NHCH$_2$CONHCHCH$_3$CH$_2$OH | CH$_2$OH |

TABLE 9

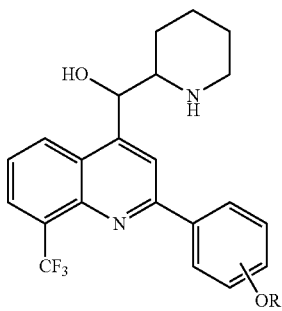

| Number | R |
|---|---|
| 1 | H |
| 2 | CH$_2$CONH$_2$ |
| 3 | CH$_2$CONR$_2$ |
| 4 | —C$_{0-4}$ alkyl-CO$_2$R |
| 5 | CH$_2$CH$_2$CONRCH$_2$CO$_2$R |
| 6 | —C$_{0-4}$ alkyl-PO(OR)$_2$ |
| 7 | —C$_{0-4}$ alkyl-SO$_2$OR |
| 8 | CH$_2$—C$_{0-4}$ alkyl-N$^+$(CH$_3$)$_3$V$^-$ |
| 9 | (CH$_2$CH$_2$O)$_q$R$^4$ |
| 10 | —C$_{0-4}$ alkyl-_tetrazole |
| 11 | —C$_{0-4}$ alkyl-SO$_2$OR |
| 12 | —C$_{0-4}$ alkyl--heteroaryl |

TABLE 10

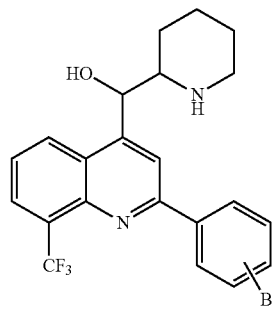

| Number | B |
|---|---|
| 1 | NH$_2$ |
| 2 | NRSO$_2$CH$_3$ |
| 3 | NR—C$_{1-4}$ alkyl-CO$_2$R |
| 4 | NR—C$_{1-4}$ alkyl-CON(R)$_2$ |
| 5 | NR—C$_{0-4}$ alkyl-PO(OR)$_2$ |
| 6 | NR—C$_{0-4}$ alkyl-SO$_2$OR,NR—C$_{0-4}$ alkyl--tetrazole |
| 7 | NR—C$_{0-4}$ alkyl--biphenyl--C$_{1-4}$ alkyl-CO$_2$R |
| 8 | NR—C$_{0-4}$ alkyl--biphenyl--C$_{1-4}$ alkyl-CON(R)$_2$ |
| 9 | NR—C$_{0-4}$ alkyl--heteroaryl |
| 10 | NR—C$_{0-4}$ alkyl--aryl-C$_{1-4}$ alkyl-CON(R)$_2$ |
| 11 | NR—C$_{0-4}$ alkyl--aryl—C$_{0-4}$ alkyl-CON(R)$_2$ |
| 12 | NR—C$_{0-4}$ alkyl--heteroaryl-C$_{1-4}$ alkyl-CO$_2$R |
| 13 | NR—C$_{0-4}$ alkyl--heteroaryl-C$_{1-4}$ alkyl-CON(R)$_2$ |
| 14 | NR—C$_{0-4}$ alkyl--heteroaryl-NR—C$_{0-4}$ alkyl-CON(R)$_2$ |
| 15 | tetrazole |
| 16 | heteroaryl |
| 17 | SO$_2$NRCH$_3$ |
| 18 | —C$_{1-4}$ alkyl--tetrazole |
| 19 | —C$_{1-4}$ alkyl-CO$_2$R |
| 20 | —C$_{1-4}$ alkyl-CONR$_2$ |

TABLE 11

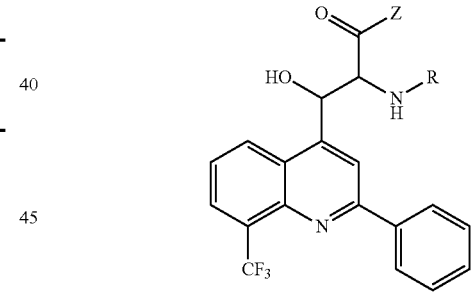

| Number | Z | R |
|---|---|---|
| 1 | OEt | H |
| 2 | OH | H |
| 3 | NH$_2$ | H |
| 4 | NHOH | H |
| 5 | NHCHCH$_3$CH$_2$OH | H |
| 6 | OEt | CH$_3$ |
| 7 | OH | CH$_3$ |
| 8 | NH$_2$ | CH$_3$ |
| 9 | NHOH | CH$_3$ |
| 10 | NHCHCH$_3$CH$_2$OH | CH$_3$ |
| 11 | OEt | CH$_2$CH$_3$ |
| 12 | OH | CH$_2$CH$_3$ |
| 13 | NH$_2$ | CH$_2$CH$_3$ |
| 14 | NHOH | CH$_2$CH$_3$ |
| 15 | NHCHCH$_3$CH$_2$OH | CH$_2$CH$_3$ |
| 16 | OEt | CH(CH$_3$)$_2$ |
| 17 | OH | CH(CH$_3$)$_2$ |
| 18 | NH$_2$ | CH(CH$_3$)$_2$ |
| 19 | NHOH | CH(CH$_3$)$_2$ |
| 20 | NHCHCH$_3$CH$_2$OH | CH(CH$_3$)$_2$ |

TABLE 11-continued

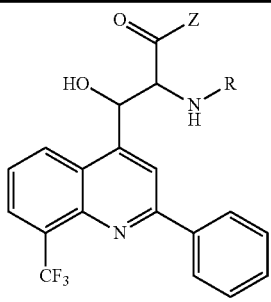

| Number | Z | R |
|---|---|---|
| 21 | OEt | cyclohexyl |
| 22 | OH | cyclohexyl |
| 23 | $NH_2$ | cyclohexyl |
| 24 | NHOH | cyclohexyl |
| 25 | $NHCHCH_3CH_2OH$ | cyclohexyl |
| 26 | OEt | cyclopentyl |
| 27 | OH | cyclopentyl |
| 28 | $NH_2$ | cyclopentyl |
| 29 | NHOH | cyclopentyl |
| 30 | $NHCHCH_3CH_2OH$ | cyclopentyl |
| 31 | $NHCH_2CO_2Et$ | H |
| 32 | $NHCH_2CO_2H$ | H |
| 33 | $NHCH_2CONH_2$ | H |
| 34 | $NHCH_2CONHOH$ | H |
| 35 | $NHCH_2CONHCHCH_3CH_2OH$ | H |
| 36 | $NHCH_2CO_2Et$ | $CH_3$ |
| 37 | $NHCH_2CO_2H$ | $CH_3$ |
| 38 | $NHCH_2CONH_2$ | $CH_3$ |
| 39 | $NHCH_2CONHOH$ | $CH_3$ |
| 40 | $NHCH_2CONHCHCH_3CH_2OH$ | $CH_3$ |
| 41 | $NHCH_2CO_2Et$ | $CH_2CH_3$ |
| 42 | $NHCH_2CO_2H$ | $CH_2CH_3$ |
| 43 | $NHCH_2CONH_2$ | $CH_2CH_3$ |
| 44 | $NHCH_2CONHOH$ | $CH_2CH_3$ |
| 45 | $NHCH_2CONHCHCH_3CH_2OH$ | $CH_2CH_3$ |
| 46 | $NHCH_2CO_2Et$ | $CH(CH_3)_2$ |
| 47 | $NHCH_2CO_2H$ | $CH(CH_3)_2$ |
| 48 | $NHCH_2CONH_2$ | $CH(CH_3)_2$ |
| 49 | $NHCH_2CONHOH$ | $CH(CH_3)_2$ |
| 50 | $NHCH_2CONHCHCH_3CH_2OH$ | $CH(CH_3)_2$ |
| 51 | $NHCH_2CO_2Et$ | cyclohexyl |
| 52 | $NHCH_2CO_2H$ | cyclohexyl |
| 53 | $NHCH_2CONH_2$ | cyclohexyl |
| 54 | $NHCH_2CONHOH$ | cyclohexyl |
| 55 | $NHCH_2CONHCHCH_3CH_2OH$ | cyclohexyl |
| 56 | $NHCH_2CO_2Et$ | cyclopentyl |
| 57 | $NHCH_2CO_2H$ | cyclopentyl |
| 58 | $NHCH_2CONH_2$ | cyclopentyl |
| 59 | $NHCH_2CONHOH$ | cyclopentyl |
| 60 | $NHCH_2CONHCHCH_3CH_2OH$ | cyclopentyl |

TABLE 12

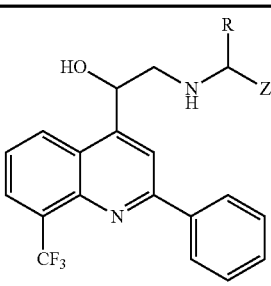

| Number | Z | R |
|---|---|---|
| 1 | $CO_2Et$ | H |
| 2 | $CO_2H$ | H |

TABLE 12-continued

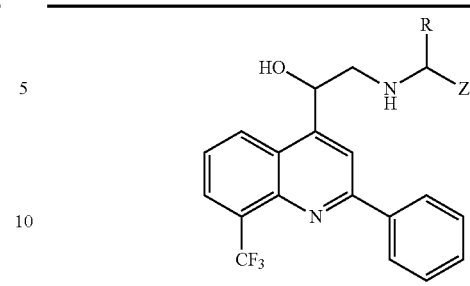

| Number | Z | R |
|---|---|---|
| 3 | $CONH_2$ | H |
| 4 | CONHOH | H |
| 5 | $CONHCHCH_3CH_2OH$ | H |
| 6 | $CO_2Et$ | $CH_3$ |
| 7 | $CO_2H$ | $CH_3$ |
| 8 | $CONH_2$ | $CH_3$ |
| 9 | CONHOH | $CH_3$ |
| 10 | $CONHCHCH_3CH_2OH$ | $CH_3$ |
| 11 | $CO_2Et$ | $CH_2CH_3$ |
| 12 | $CO_2H$ | $CH_2CH_3$ |
| 13 | $CONH_2$ | $CH_2CH_3$ |
| 14 | CONHOH | $CH_2CH_3$ |
| 15 | $CONHCHCH_3CH_2OH$ | $CH_2CH_3$ |
| 16 | $CO_2Et$ | $CH(CH_3)_2$ |
| 17 | $CO_2H$ | $CH(CH_3)_2$ |
| 18 | $CONH_2$ | $CH(CH_3)_2$ |
| 19 | CONHOH | $CH(CH_3)_2$ |
| 20 | $CONHCHCH_3CH_2OH$ | $CH(CH_3)_2$ |
| 21 | $CO_2Et$ | $CH_2CH(CH_3)_2$ |
| 22 | $CO_2H$ | $CH_2CH(CH_3)_2$ |
| 23 | $CONH_2$ | $CH_2CH(CH_3)_2$ |
| 24 | CONHOH | $CH_2CH(CH_3)_2$ |
| 25 | $CONHCHCH_3CH_2OH$ | $CH_2CH(CH_3)_2$ |
| 26 | $CO_2Et$ | cyclohexyl |
| 27 | $CO_2H$ | cyclohexyl |
| 28 | $CONH_2$ | cyclohexyl |
| 29 | CONHOH | cyclohexyl |
| 30 | $CONHCHCH_3CH_2OH$ | cyclohexyl |
| 31 | $CO_2Et$ | $CHOH(CH_3)_2$ |
| 32 | $CO_2H$ | $CHOH(CH_3)_2$ |
| 33 | $CONH_2$ | $CHOH(CH_3)_2$ |
| 34 | CONHOH | $CHOH(CH_3)_2$ |
| 35 | $CONHCHCH_3CH_2OH$ | $CHOH(CH_3)_2$ |
| 36 | $CONHCH_2CO_2Et$ | H |
| 37 | $CONHCH_2CO_2H$ | H |
| 38 | $CONHCH_2CONH_2$ | H |
| 39 | $CONHCH_2CONHOH$ | H |
| 40 | $CONHCH_2CONHCHCH_3CH_2OH$ | H |
| 41 | $CONHCH_2CO_2Et$ | $CH_3$ |
| 42 | $CONHCH_2CO_2H$ | $CH_3$ |
| 43 | $CONHCH_2CONH_2$ | $CH_3$ |
| 44 | $CONHCH_2CONHOH$ | $CH_3$ |
| 45 | $CONHCH_2CONHCHCH_3CH_2OH$ | $CH_3$ |
| 46 | $CONHCH_2CO_2Et$ | $CH_2CH_3$ |
| 47 | $CONHCH_2CO_2H$ | $CH_2CH_3$ |
| 48 | $CONHCH_2CONH_2$ | $CH_2CH_3$ |
| 49 | $CONHCH_2CONHOH$ | $CH_2CH_3$ |
| 50 | $CONHCH_2CONHCHCH_3CH_2OH$ | $CH_2CH_3$ |
| 51 | $CONHCH_2CO_2Et$ | $CH(CH_3)_2$ |
| 52 | $CONHCH_2CO_2H$ | $CH(CH_3)_2$ |
| 53 | $CONHCH_2CONH_2$ | $CH(CH_3)_2$ |
| 54 | $CONHCH_2CONHOH$ | $CH(CH_3)_2$ |
| 55 | $CONHCH_2CONHCHCH_3CH_2OH$ | $CH(CH_3)_2$ |
| 56 | $CONHCH_2CO_2Et$ | cyclohexyl |
| 57 | $CONHCH_2CO_2H$ | cyclohexyl |
| 58 | $CONHCH_2CONH_2$ | cyclohexyl |
| 59 | $CONHCH_2CONHOH$ | cyclohexyl |
| 60 | $CONHCH_2CONHCHCH_3CH_2OH$ | cyclohexyl |
| 61 | $CONHCH_2CO_2Et$ | $CHOH(CH_3)_2$ |
| 62 | $CONHCH_2CO_2H$ | $CHOH(CH_3)_2$ |
| 63 | $CONHCH_2CONH_2$ | $CHOH(CH_3)_2$ |
| 64 | $CONHCH_2CONHOH$ | $CHOH(CH_3)_2$ |
| 65 | $CONHCH_2CONHCHCH_3CH_2OH$ | $CHOH(CH_3)_2$ |
| 66 | H | $CH_2CH_2CO_2Et$ |

TABLE 12-continued

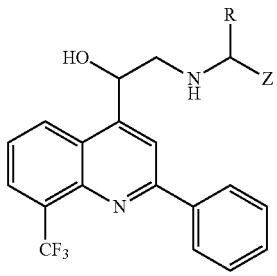

| Number | Z | R |
|---|---|---|
| 67 | H | $CH_2CH_2CO_2H$ |
| 68 | H | $CH_2CH_2CONH_2$ |
| 69 | H | $CH_2CH_2CONHOH$ |
| 70 | H | $CH_2CH_2CONHCH_2CH_2OH$ |
| 71 | H | $CH_2CHOHCO_2Et$ |
| 72 | H | $CH_2CHOHCO_2H$ |
| 73 | H | $CH_2CHOHCONH_2$ |
| 74 | H | $CH_2CHOHCONHOH$ |
| 75 | H | $CH_2CHOHCONHCH_2CH_2OH$ |
| 76 | H | $CHOHCH_2CO_2Et$ |
| 77 | H | $CHOHCH_2CO_2H$ |
| 78 | H | $CHOHCH_2CONH_2$ |
| 79 | H | $CHOHCH_2CONHOH$ |
| 80 | H | $CHOHCH_2CONHCH_2CH_2OH$ |
| 81 | H | $CH{=}CHCO_2Et$ |
| 82 | H | $CH{=}CHCO_2H$ |
| 83 | H | $CH{=}CHCONH_2$ |
| 84 | H | $CH{=}CHCONHOH$ |
| 85 | H | $CH{=}CHCONHCH_2CH_2OH$ |
| 86 | $CH_3$ | $CH_2CO_2Et$ |
| 87 | $CH_3$ | $CH_2CO_2H$ |
| 88 | $CH_3$ | $CH_2CONH_2$ |
| 89 | $CH_3$ | $CH_2CONHOH$ |
| 90 | $CH_3$ | $CH_2CONHCH_2CH_2OH$ |

Numerous modifications and variations of the present invention are possible in light of the above teachings. It is therefore to be understood that within the scope of the appended claims, the invention may be practiced otherwise that as specifically described herein.

What is claimed is:

1. A compound of formula A or a stereoisomer or pharmaceutically acceptable salt thereof:

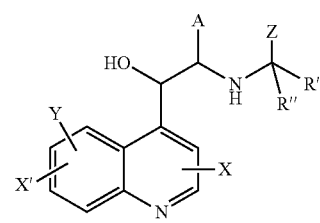

A wherein:
A is selected from $(CH_2)_nCONHA'$ and $(CH_2)_nCONHOH$;
n is selected from 0, 1, 2, 3, and 4;
A' is selected from H and $CR'R''Z$;
R at each occurrence is independently selected from H and $C_{1-4}$ alkyl;
R' is selected from H, $C_{1-4}$ alkyl, $C_{3-6}$-cycloalkyl, $C_{1-4}$ hydroxyalkyl, phenyl, benzyl, —$C_{0-4}$ alkyl-$CO_2R$, —$C_{0-4}$ alkyl-$CONHR^a$, —$C_{0-4}$ alkyl-CONHOH, and —$C_{0-4}$ alkyl-$C(NH)NH_2$;
$R^a$ is selected from H and —$C_{1-4}$ alkyl-$CONHR^b$;
$R^b$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$;
R" is selected from H and $C_{1-4}$ alkyl;
alternatively, R' and R" together form a $C_{3-6}$ cycloalkyl group;
X is selected from H, halo, —CN, O—$C_{1-4}$ alkyl, $C_{2-4}$ alkenyl, $CF_3$, and phenyl;
X' is selected from H, halo, —CN, O—$C_{1-4}$ alkyl, $C_{2-4}$ alkenyl, and $CF_3$;
Y is selected from H, halo, —CN, O—$C_{1-4}$ alkyl, $C_{2-4}$ alkenyl, and $CF_3$;
Z is selected from H, $C_{1-4}$ alkyl, $C_{1-4}$ hydroxyalkyl, $C_{2-4}$ alkenyl, $C_{2-4}$ alkynyl, phenyl, phenyl-$C_{1-6}$ alkyl-, —$C_{0-4}$ alkyl-$CO_2R$, —$C_{0-4}$ alkyl-$CONHR^c$, —$C_{0-4}$ alkyl-CONHOH, —$C_{0-4}$ alkyl-$C(NH)NH_2$, $CHOHCH_2CO_2R$, $CHOHCH_2CONHR^c$, $CHOHCH_2C(NH)NH_2$, $CH_2CHOHCO_2R$, $CH_2CHOHCONHR^c$, $CH_2CHOHC(NH)NH_2$, $CH{=}CHCO_2R$, $CH{=}CHCONHQ$, $CH{=}CHC(NH)NH_2$, —$C_{1-4}$ alkyl-$SO_3R$, and —$C_{1-4}$ alkyl-$SO_2NHR^c$;
$R^c$ is selected from H, —$C_{1-4}$ alkyl-$CONHR^d$, $CHOHCH_2CONHR^d$, $CH_2CHOHCONHR^d$, and —$C_{1-4}$ alkyl-$SO_2NHR^d$;
$R^d$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$; and,
each phenyl or benzyl group is independently optionally substituted with 1-2 groups selected from $CF_3$, halogen, $C_{1-4}$ alkyl, —CN, $CONR_2$, $NO_2$, $NR_2$, OR, $NHSO_2CH_3$, and SONHR;
provided that when A=H, then one of R' and Z is other than H, $C_{1-4}$ alkyl, $C_{2-4}$ alkenyl, $C_{2-4}$ alkynyl, $C_{3-6}$-cycloalkyl, $C_{1-4}$ hydroxyalkyl, phenyl, and phenyl-$C_{1-6}$ alkyl-.

2. A compound of claim 1, wherein the compound is of formula I or a stereoisomer or pharmaceutically acceptable salt thereof:

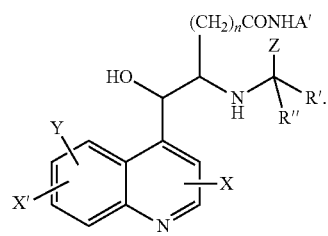

I

3. A compound of claim 2, wherein the compound is of formula $I_A$ or a stereoisomer or pharmaceutically acceptable salt thereof:

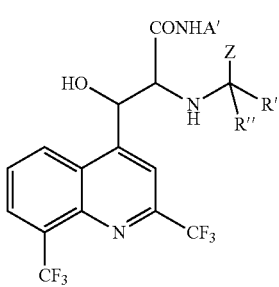

$I_A$ wherein:

A' is selected from H and CR'R"Z;

R at each occurrence is independently selected from H and $C_{1-4}$ alkyl;

R' is selected from H, $C_{1-4}$ alkyl, $C_{3-6}$-cycloalkyl, $C_{1-4}$ hydroxyalkyl, phenyl, benzyl, —$C_{0-4}$ alkyl-$CO_2R$, —$C_{0-4}$ alkyl-$CONHR^a$, —$C_{0-4}$ alkyl-CONHOH, and —$C_{0-4}$ alkyl-C(NH)$NH_2$;

$R^a$ is selected from H and —$C_{1-4}$ alkyl-$CONHR^b$;

$R^b$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$;

R" is selected from H and $C_{1-4}$ alkyl;

alternatively, R' and R" together form a $C_{3-6}$ cycloalkyl group;

Z is selected from H, $C_{1-4}$ alkyl, $C_{1-4}$ hydroxyalkyl, $C_{2-4}$ alkenyl, $C_{2-4}$ alkynyl, phenyl, phenyl-$C_{1-6}$ alkyl-, —$C_{0-4}$ alkyl-$CO_2R$, —$C_{0-4}$ alkyl-$CONHR^c$, —$C_{0-4}$ alkyl-C(NH)$NH_2$, —$C_{0-4}$ alkyl-CONHOH, $CHOHCH_2CO_2R$, $CHOHCH_2CONHR^c$, $CHOHCH_2C(NH)NH_2$, $CH_2CHOHCO_2R$, $CH_2CHOHCONHR^c$, $CH_2CHOHC(NH)NH_2$, CH=$CHCO_2R$, CH=CHCONHQ, CH=CHC(NH)$NH_2$, —$C_{1-4}$ alkyl-$SO_3R$, and —$C_{1-4}$ alkyl-$SO_2NHR^c$;

$R^c$ is selected from H, —$C_{1-4}$ alkyl-$CONHR^d$, $CHOHCH_2CONHR^d$, $CH_2CHOHCONHR^d$, and —$C_{1-4}$ alkyl-$SO_2NHR^d$;

$R^d$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$;

each phenyl or benzyl group is independently optionally substituted with 1-2 groups selected from $CF_3$, halogen, $C_{1-4}$ alkyl, —CN, $CONR_2$, $NO_2$, $NR_2$, OR, $NHSO_2CH_3$, and SONHR.

5. A pharmaceutical composition, comprising: a compound according to claim 1 and a pharmaceutically acceptable carrier.

6. A method of treating a disease, comprising: administering to a mammal in need thereof a therapeutically effective amount of a compound of according to claim 1, wherein the disease is selected from malaria, tuberculosis, and a combination thereof.

7. A method of treating malaria, tuberculosis, and combination thereof, comprising: administering to a mammal in need thereof a therapeutically effective amount of
 a. a first component that is a compound of according to claim 1, and
 b. a second component selected from a known anti-malarial or antibiotic.

8. A method of modulating the activity of malaria, tuberculosis in a patient, comprising: administering a compound or composition according to claim 1.

9. The method of claim 8, wherein the pathogens are in the peripheral circulatory system.

10. A compound of claim 1, wherein the compound is a compound of Table 1 or a stereoisomer or pharmaceutically acceptable salt thereof:

4. A compound of claim 2, wherein the compound is of formula $I_B$ or a stereoisomer or pharmaceutically acceptable salt thereof:

$I_B$ wherein:

A' is selected from H and CR'R"Z;

R at each occurrence is independently selected from H and $C_{1-4}$ alkyl;

R' is selected from H, $C_{1-4}$ alkyl, $C_{3-6}$-cycloalkyl, $C_{1-4}$ hydroxyalkyl, phenyl, benzyl, —$C_{0-4}$ alkyl-$CO_2R$, —$C_{0-4}$ alkyl-$CONHR^a$, —$C_{0-4}$ alkyl-CONHOH, and —$C_{0-4}$ alkyl-C(NH)$NH_2$;

$R^a$ is selected from H and —$C_{1-4}$ alkyl-$CONHR^b$;

$R^b$ is selected from $C_{1-4}$ alkyl, $C_{1-4}$ hydroxyalkyl, $C_{3-4}$ alkenyl, $C_{3-4}$ alkynyl, phenyl, phenyl-$C_{1-6}$ alkyl-, and —$C_{1-4}$ alkyl-$CONH_2$;

R" is selected from H and $C_{1-4}$ alkyl;

TABLE 1

| Number | Z | X | Y |
|---|---|---|---|
| 1. | $NH_2$ | H | H |
| 2. | NHOH | H | H |
| 3. | $NH_2$ | F | H |
| 4. | NHOH | F | H |
| 5. | $NH_2$ | Cl | H |
| 6. | NHOH | Cl | H |
| 7. | $NH_2$ | $CH_3$ | H |

TABLE 1-continued

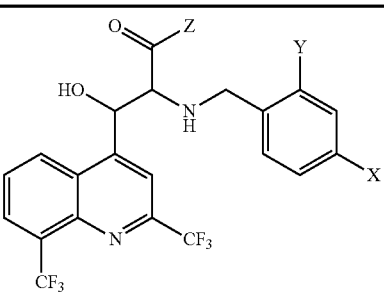

| Number | Z | X | Y |
|---|---|---|---|
| 8. | NHOH | CH$_3$ | H |
| 9. | NH$_2$ | OCH$_3$ | H |
| 10. | NHOH | OCH$_3$ | H |
| 11. | NH$_2$ | H | Cl |
| 12. | NHOH | H | Cl |
| 13. | NH$_2$ | F | Cl |
| 14. | NHOH | F | Cl |
| 15. | NH$_2$ | Cl | Cl |
| 16. | NHOH | Cl | Cl |
| 17. | NH$_2$ | CH$_3$ | Cl |
| 18. | NHOH | CH$_3$ | Cl |
| 19. | CH(CH$_3$)CONH$_2$ | OCH$_3$ | Cl |
| 20. | CH(CH$_3$)CONHOH | OCH$_3$ | Cl. |

11. A compound of claim 1, wherein the compound is a compound of Table 2 or a stereoisomer or pharmaceutically acceptable salt thereof:

TABLE 2

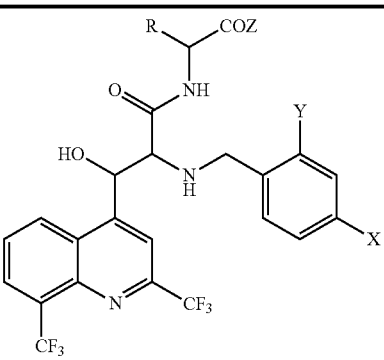

| Number | R | Z | X | Y |
|---|---|---|---|---|
| 1 | H | OEt | H | H |
| 2 | H | OH | H | H |
| 3 | H | NH$_2$ | H | H |
| 4 | H | NHOH | H | H |
| 5 | H | OEt | F | H |
| 6 | H | OH | F | H |
| 7 | H | NH$_2$ | F | H |
| 8 | H | NHOH | F | H |
| 9 | H | OEt | Cl | H |
| 10 | H | OH | Cl | H |
| 11 | H | NH$_2$ | Cl | H |
| 12 | H | NHOH | Cl | H |
| 13 | H | OEt | CH$_3$ | H |
| 14 | H | OH | CH$_3$ | H |
| 15 | H | NH$_2$ | CH$_3$ | H |
| 16 | H | NHOH | CH$_3$ | H |
| 17 | H | OEt | OCH$_3$ | H |
| 18 | H | OH | OCH$_3$ | H |
| 19 | H | NH$_2$ | OCH$_3$ | H |
| 20 | H | NHOH | OCH$_3$ | H |
| 21 | H | OEt | H | Cl |
| 22 | H | OH | H | Cl |

TABLE 2-continued

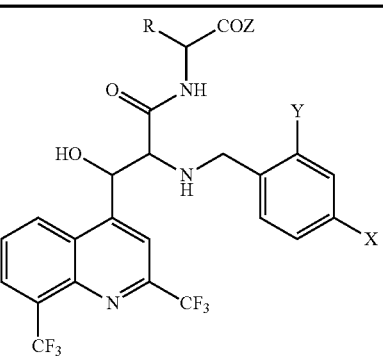

| Number | R | Z | X | Y |
|---|---|---|---|---|
| 23 | H | NH$_2$ | H | Cl |
| 24 | H | NHOH | H | Cl |
| 25 | H | OEt | F | Cl |
| 26 | H | OH | F | Cl |
| 27 | H | NH$_2$ | F | Cl |
| 28 | H | NHOH | F | Cl |
| 29 | H | OEt | Cl | Cl |
| 30 | H | OH | Cl | Cl |
| 31 | H | NH$_2$ | Cl | Cl |
| 32 | H | NHOH | Cl | Cl |
| 33 | H | OEt | CH$_3$ | Cl |
| 34 | H | OH | CH$_3$ | Cl |
| 35 | H | NH$_2$ | CH$_3$ | Cl |
| 36 | H | NHOH | CH$_3$ | Cl |
| 37 | H | OEt | OCH$_3$ | Cl |
| 38 | H | OH | OCH$_3$ | Cl |
| 39 | H | NH$_2$ | OCH$_3$ | Cl |
| 40 | H | NHOH | OCH$_3$ | Cl |
| 41 | CH$_3$ | OEt | H | H |
| 42 | CH$_3$ | OH | H | H |
| 43 | CH$_3$ | NH$_2$ | H | H |
| 44 | CH$_3$ | NHOH | H | H |
| 45 | CH$_3$ | OEt | F | H |
| 46 | CH$_3$ | OH | F | H |
| 47 | CH$_3$ | NH$_2$ | F | H |
| 48 | CH$_3$ | NHOH | F | H |
| 49 | CH$_3$ | OEt | Cl | H |
| 50 | CH$_3$ | OH | Cl | H |
| 51 | CH$_3$ | NH$_2$ | Cl | H |
| 52 | CH$_3$ | NHOH | Cl | H |
| 53 | CH$_3$ | OEt | CH$_3$ | H |
| 54 | CH$_3$ | OH | CH$_3$ | H |
| 55 | CH$_3$ | NH$_2$ | CH$_3$ | H |
| 56 | CH$_3$ | NHOH | CH$_3$ | H |
| 57 | CH$_3$ | OEt | OCH$_3$ | H |
| 58 | CH$_3$ | OH | OCH$_3$ | H |
| 59 | CH$_3$ | NH$_2$ | OCH$_3$ | H |
| 60 | CH$_3$ | NHOH | OCH$_3$ | H |
| 61 | CH$_3$ | OEt | H | Cl |
| 62 | CH$_3$ | OH | H | Cl |
| 63 | CH$_3$ | NH$_2$ | H | Cl |
| 64 | CH$_3$ | NHOH | H | Cl |
| 65 | CH$_3$ | OEt | F | Cl |
| 66 | CH$_3$ | OH | F | Cl |
| 67 | CH$_3$ | NH$_2$ | F | Cl |
| 68 | CH$_3$ | NHOH | F | Cl |
| 69 | CH$_3$ | OEt | Cl | Cl |
| 70 | CH$_3$ | OH | Cl | Cl |
| 71 | CH$_3$ | NH$_2$ | Cl | Cl |
| 72 | CH$_3$ | NHOH | Cl | Cl |
| 73 | CH$_3$ | OEt | CH$_3$ | Cl |
| 74 | CH$_3$ | OH | CH$_3$ | Cl |
| 75 | CH$_3$ | NH$_2$ | CH$_3$ | Cl |
| 76 | CH$_3$ | NHOH | CH$_3$ | Cl |
| 77 | CH$_3$ | OEt | OCH$_3$ | Cl |
| 78 | CH$_3$ | OH | OCH$_3$ | Cl |
| 79 | CH$_3$ | NH$_2$ | OCH$_3$ | Cl |
| 80 | CH$_3$ | NHOH | OCH$_3$ | Cl. |

12. A compound of claim 1, wherein the compound is a compound of Table 3 or a stereoisomer or pharmaceutically acceptable salt thereof:

TABLE 3

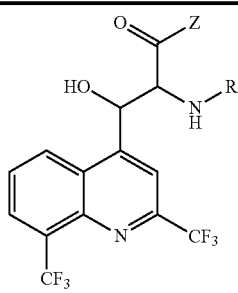

| Number | Z | R |
|---|---|---|
| 1. | NH$_2$ | H |
| 2. | NHOH | H |
| 3. | NHCHCH$_3$CH$_2$OH | H |
| 4. | NH$_2$ | CH$_3$ |
| 5. | NHOH | CH$_3$ |
| 6. | NHCHCH$_3$CH$_2$OH | CH$_3$ |
| 7. | NH$_2$ | CH$_2$CH$_3$ |
| 8. | NHOH | CH$_2$CH$_3$ |
| 9. | NHCHCH$_3$CH$_2$OH | CH$_2$CH$_3$ |
| 10. | NH$_2$ | CH(CH$_3$)$_2$ |
| 11. | NHOH | CH(CH$_3$)$_2$ |
| 12. | NHCHCH$_3$CH$_2$OH | CH(CH$_3$)$_2$ |
| 13. | NH$_2$ | cyclohexyl |
| 14. | NHOH | cyclohexyl |
| 15. | NHCHCH$_3$CH$_2$OH | cyclohexyl |
| 16. | NH$_2$ | cyclopentyl |
| 17. | NHOH | cyclopentyl |
| 18. | NHCHCH$_3$CH$_2$OH | cyclopentyl |
| 19. | NHCH$_2$CO$_2$Et | H |
| 20. | NHCH$_2$CO$_2$H$_2$ | H |
| 21. | NHCH$_2$CONH$_2$ | H |
| 22. | NHCH$_2$CONHOH | H |
| 23. | NHCH$_2$CONHCHCH$_3$CH$_2$OH | H |
| 24. | NHCH$_2$CO$_2$Et | CH$_3$ |
| 25. | NHCH$_2$CO$_2$H$_2$ | CH$_3$ |
| 26. | NHCH$_2$CONH$_2$ | CH$_3$ |
| 27. | NHCH$_2$CONHOH | CH$_3$ |
| 28. | NHCH$_2$CONHCHCH$_3$CH$_2$OH | CH$_3$ |
| 29. | NHCH$_2$CO$_2$Et | CH$_2$CH$_3$ |
| 30. | NHCH$_2$CO$_2$H$_2$ | CH$_2$CH$_3$ |
| 31. | NHCH$_2$CONH$_2$ | CH$_2$CH$_3$ |
| 32. | NHCH$_2$CONHOH | CH$_2$CH$_3$ |
| 33. | NHCH$_2$CONHCHCH$_3$CH$_2$OH | CH$_2$CH$_3$ |
| 34. | NHCH$_2$CO$_2$Et | CH(CH$_3$)$_2$ |

TABLE 3-continued

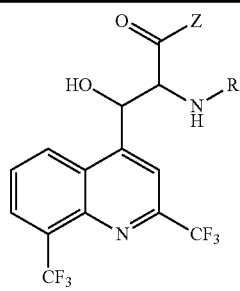

| Number | Z | R |
|---|---|---|
| 35. | NHCH$_2$CO$_2$H$_2$ | CH(CH$_3$)$_2$ |
| 36. | NHCH$_2$CONH$_2$ | CH(CH$_3$)$_2$ |
| 37. | NHCH$_2$CONHOH | CH(CH$_3$)$_2$ |
| 38. | NHCH$_2$CONHCHCH$_3$CH$_2$OH | CH(CH$_3$)$_2$ |
| 39. | NHCH$_2$CO$_2$Et | cyclohexyl |
| 40. | NHCH$_2$CO$_2$H$_2$ | cyclohexyl |
| 41. | NHCH$_2$CONH$_2$ | cyclohexyl |
| 42. | NHCH$_2$CONHOH | cyclohexyl |
| 43. | NHCH$_2$CONHCHCH$_3$CH$_2$OH | cyclohexyl |
| 44. | NHCH$_2$CO$_2$Et | cyclopentyl |
| 45. | NHCH$_2$CO$_2$H$_2$ | cyclopentyl |
| 46. | NHCH$_2$CONH$_2$ | cyclopentyl |
| 47. | NHCH$_2$CONHOH | cyclopentyl |
| 48. | NHCH$_2$CONHCHCH$_3$CH$_2$OH | cyclopentyl. |

13. A pharmaceutical composition, comprising: a compound according to claim 2 and a pharmaceutically acceptable carrier.

14. A pharmaceutical composition, comprising: a compound according to claim 3 and a pharmaceutically acceptable carrier.

15. A pharmaceutical composition, comprising: a compound according to claim 4 and a pharmaceutically acceptable carrier.

16. A pharmaceutical composition, comprising: a compound according to claim 10 and a pharmaceutically acceptable carrier.

17. A pharmaceutical composition, comprising: a compound according to claim 11 and a pharmaceutically acceptable carrier.

18. A pharmaceutical composition, comprising: a compound according to claim 12 and a pharmaceutically acceptable carrier.

* * * * *